(12) United States Patent
Korb et al.

(10) Patent No.: US 9,719,977 B2
(45) Date of Patent: Aug. 1, 2017

(54) METHODS AND SYSTEMS FOR TREATING MEIBOMIAN GLAND DYSFUNCTION USING RADIO-FREQUENCY ENERGY

(75) Inventors: Donald R. Korb, Boston, MA (US); Stephen M. Grenon, Durham, NC (US); Timothy R. Willis, Raleigh, NC (US); Benjamin Tyson Gravely, Raleigh, NC (US); Steven Bacich, Half Moon Bay, CA (US)

(73) Assignee: TearScience, Inc., Morrisville, NC (US)

( * ) Notice: Subject to any disclaimer, the term of this patent is extended or adjusted under 35 U.S.C. 154(b) by 1150 days.

(21) Appl. No.: 13/590,828

(22) Filed: Aug. 21, 2012

(65) Prior Publication Data

US 2013/0053733 A1 Feb. 28, 2013

Related U.S. Application Data

(60) Continuation of application No. PCT/US2012/044650, filed on Jun. 28, 2012, and a
(Continued)

(51) Int. Cl.
A61F 7/08 (2006.01)
A61F 9/00 (2006.01)
(Continued)

(52) U.S. Cl.
CPC ........... G01N 33/227 (2013.01); A61F 9/007 (2013.01); A61F 9/00718 (2013.01);
(Continued)

(58) Field of Classification Search
CPC ................... A61F 9/00718; A61F 2009/00885
See application file for complete search history.

(56) References Cited

U.S. PATENT DOCUMENTS 1,006,945 A 10/1911 Houston
1,924,315 A 8/1933 Hemphill et al.
(Continued)

FOREIGN PATENT DOCUMENTS

AU 2011302478 A1 3/2013
CA 2331257 A1 11/1999
(Continued)

OTHER PUBLICATIONS

No Author, "arGentis Licenses Third Treatment for Dry Eye Syndrome", Business Wire, May 12, 2008, accessed Jun. 4, 2008, 2 pages.
(Continued)

Primary Examiner — Kaitlyn Smith
(74) Attorney, Agent, or Firm — Withrow & Terranova, PLLC

(57) ABSTRACT

A method of treating meibomian gland dysfunction is disclosed. The method includes directing RF energy to an internal portion of a meibomian gland, selectively targeting an obstruction within a duct of the meibomian gland with the applied RF energy to melt, loosen, or soften the obstruction, and expressing the obstruction from the duct of the meibomian gland. An apparatus for treating meibomian gland dysfunction is also disclosed. The apparatus comprises at least one RF electrode configured to direct RF energy to an internal portion of a meibomian gland located in an eyelid of an eye, the at least one RF electrode further configured to selectively target an obstruction within a duct of the meibomian gland with the applied RF energy to melt, loosen, or soften the obstruction. The apparatus also comprises at least one expressor configured to express the obstruction from the duct of the meibomian gland.

18 Claims, 37 Drawing Sheets

Related U.S. Application Data continuation-in-part of application No. 11/434,033, filed on May 15, 2006, now Pat. No. 8,915,253, application No. 13/590,828, which is a continuation-in-part of application No. 11/931,398, filed on Oct. 31, 2007, now Pat. No. 9,060,843, which is a continuation of application No. 11/434,033, filed on May 15, 2006, now Pat. No. 8,915,253, application No. 13/590,828, which is a continuation-in-part of application No. 13/242,068, filed on Sep. 23, 2011, now Pat. No. 8,685,073, which is a continuation of application No. 12/281,183, filed on Nov. 13, 2008, now abandoned, which is a division of application No. 11/434,054, filed on May 15, 2006, now Pat. No. 8,083,787, application No. 13/590,828, which is a continuation-in-part of application No. 13/183,901, filed on Jul. 15, 2011, now Pat. No. 9,216,028, which is a continuation of application No. 11/541,418, filed on Sep. 29, 2006, now Pat. No. 7,981,145, application No. 13/590,828, which is a continuation-in-part of application No. 11/541,308, filed on Sep. 29, 2006, and a continuation-in-part of application No. 11/893,669, filed on Aug. 17, 2007, now Pat. No. 8,255,039, and a continuation-in-part of application No. 12/015,593, filed on Jan. 17, 2008, now abandoned.

(60) Provisional application No. 61/502,120, filed on Jun. 28, 2011, provisional application No. 60/700,233, filed on Jul. 18, 2005, provisional application No. 60/880,850, filed on Jan. 17, 2007.

(51) Int. Cl.
| | |
|---|---|
| G01N 33/22 | (2006.01) |
| A61N 1/40 | (2006.01) |
| A61F 9/007 | (2006.01) |
| A61H 7/00 | (2006.01) |
| A61H 9/00 | (2006.01) |
| A61H 23/02 | (2006.01) |
| A61B 5/00 | (2006.01) |
| A61B 18/12 | (2006.01) |
| A61B 18/04 | (2006.01) |
| A61F 7/00 | (2006.01) |
| A61H 39/08 | (2006.01) |
| A61H 15/00 | (2006.01) |
| A61N 7/00 | (2006.01) |

(52) U.S. Cl.
CPC .......... *A61H 7/003* (2013.01); *A61H 7/005* (2013.01); *A61H 9/0057* (2013.01); *A61H 9/0071* (2013.01); *A61H 9/0078* (2013.01); *A61H 23/0236* (2013.01); *A61H 23/0245* (2013.01); *A61H 23/0263* (2013.01); *A61N 1/403* (2013.01); *A61B 5/4836* (2013.01); *A61B 18/12* (2013.01); *A61B 2018/046* (2013.01); *A61B 2018/048* (2013.01); *A61B 2562/0247* (2013.01); *A61B 2562/0271* (2013.01); *A61F 2007/0004* (2013.01); *A61F 2007/0059* (2013.01); *A61H 39/086* (2013.01); *A61H 2015/0014* (2013.01); *A61H 2201/0176* (2013.01); *A61H 2201/0207* (2013.01); *A61H 2201/0214* (2013.01); *A61H 2201/5038* (2013.01); *A61H 2201/5043* (2013.01); *A61H 2205/024* (2013.01); *A61N 7/00* (2013.01); *Y10T 436/170769* (2015.01); *Y10T 436/173076* (2015.01); *Y10T 436/173845* (2015.01); *Y10T 436/178459* (2015.01); *Y10T 436/19* (2015.01); *Y10T 436/206664* (2015.01)

(56) References Cited

U.S. PATENT DOCUMENTS

| | | |
|---|---|---|
| 2,545,724 A | 3/1951 | Curtis |
| 2,891,252 A | 6/1959 | Lazo |
| 3,140,390 A | 7/1964 | Smith et al. |
| 3,333,586 A | 8/1967 | Bellis et al. |
| 3,404,678 A | 10/1968 | Von Ardenne |
| 3,415,299 A | 12/1968 | Hinman, Jr. et al. |
| 3,667,476 A | 6/1972 | Muller |
| 3,952,735 A | 4/1976 | Wirtschafter et al. |
| 4,069,084 A | 1/1978 | Mlodozeniec et al. |
| 4,131,115 A | 12/1978 | Peng |
| 4,261,364 A | 4/1981 | Haddad et al. |
| 4,387,707 A | 6/1983 | Polikoff |
| 4,778,457 A | 10/1988 | York |
| 4,883,454 A | 11/1989 | Hamburg |
| 4,914,088 A | 4/1990 | Glonek et al. |
| 4,918,818 A | 4/1990 | Hsieh |
| 4,955,377 A | 9/1990 | Lennox et al. |
| 4,958,632 A | 9/1990 | Duggan |
| 5,030,214 A | 7/1991 | Spector |
| 5,097,829 A | 3/1992 | Quisenberry |
| 5,151,100 A | 9/1992 | Abele et al. |
| 5,158,082 A | 10/1992 | Jones |
| 5,169,384 A | 12/1992 | Bosniak et al. |
| 5,213,097 A | 5/1993 | Zeindler |
| 5,251,627 A | 10/1993 | Morris |
| 5,283,063 A | 2/1994 | Freeman |
| 5,314,456 A | 5/1994 | Cohen |
| 5,327,886 A | 7/1994 | Chiu |
| 5,343,561 A | 9/1994 | Adamo |
| D352,106 S | 11/1994 | Fanney et al. |
| 5,368,582 A | 11/1994 | Bertera |
| 5,368,591 A | 11/1994 | Lennox et al. |
| 5,377,701 A | 1/1995 | Fang |
| 5,419,772 A | 5/1995 | Teitz et al. |
| 5,425,380 A | 6/1995 | Hudson et al. |
| 5,496,311 A | 3/1996 | Abele et al. |
| 5,601,548 A | 2/1997 | Smith et al. |
| 5,628,772 A | 5/1997 | Russell |
| 5,643,336 A | 7/1997 | Lopez-Claros |
| 5,700,238 A | 12/1997 | Hyson |
| 5,720,773 A | 2/1998 | Lopez-Claros |
| 5,782,857 A | 7/1998 | Machuron |
| 5,807,357 A | 9/1998 | Kang |
| 5,836,927 A | 11/1998 | Fried |
| 5,893,719 A | 4/1999 | Radow |
| 5,958,912 A | 9/1999 | Sullivan |
| 5,960,608 A | 10/1999 | Ohtonen |
| 5,964,723 A | 10/1999 | Augustine |
| 6,007,501 A | 12/1999 | Cabados et al. |
| 6,024,095 A | 2/2000 | Stanley, III |
| 6,107,289 A | 8/2000 | Sullivan |
| 6,110,292 A | 8/2000 | Jewett et al. |
| 6,112,900 A | 9/2000 | Adkins, Jr. |
| 6,113,561 A | 9/2000 | Augustine |
| 6,153,607 A | 11/2000 | Pflugfelder et al. |
| 6,155,995 A | 12/2000 | Lin |
| 6,181,970 B1 | 1/2001 | Kasevich |
| 6,193,740 B1 | 2/2001 | Rodriguez |
| 6,206,842 B1 | 3/2001 | Tu et al. |
| 6,213,966 B1 | 4/2001 | Augustine |
| 6,273,886 B1 | 8/2001 | Edwards et al. |
| 6,275,735 B1 | 8/2001 | Jarding et al. |
| 6,309,364 B1 | 10/2001 | Cathaud et al. |
| 6,312,397 B1 | 11/2001 | Gebhard |
| D456,079 S | 4/2002 | Fujii |
| 6,423,018 B1 | 7/2002 | Augustine |
| 6,425,888 B1 | 7/2002 | Embleton et al. |
| 6,438,398 B1 | 8/2002 | Pflugfelder et al. |
| 6,455,583 B1 | 9/2002 | Pflugfelder et al. |
| 6,482,203 B2 | 11/2002 | Paddock et al. |
| 6,490,488 B1 | 12/2002 | Rudie et al. |
| D472,637 S | 4/2003 | Cooper et al. |
| 6,544,257 B2 | 4/2003 | Nagase et al. |
| D477,084 S | 7/2003 | Menezes et al. |
| 6,641,264 B1 | 11/2003 | Schwebel |

(56) References Cited

U.S. PATENT DOCUMENTS

| | | |
|---|---|---|
| 6,648,904 B2 | 11/2003 | Altshuler et al. |
| 6,706,001 B2 | 3/2004 | Fresco |
| 6,780,176 B2 | 8/2004 | Hasegawa |
| 6,788,977 B2 | 9/2004 | Fenn et al. |
| 6,827,898 B1 | 12/2004 | Fausset et al. |
| 6,840,954 B2 | 1/2005 | Dietz et al. |
| 6,860,852 B2 | 3/2005 | Schonenberger et al. |
| 6,860,880 B2 | 3/2005 | Treat et al. |
| 6,874,884 B2 | 4/2005 | Schwebel |
| 6,882,885 B2 | 4/2005 | Levy, Jr. et al. |
| 6,886,933 B2 | 5/2005 | Schwebel |
| 6,908,195 B2 | 6/2005 | Fuller |
| 6,925,317 B1 | 8/2005 | Samuels et al. |
| 6,974,454 B2 | 12/2005 | Hooven |
| 7,001,379 B2 | 2/2006 | Behl et al. |
| 7,004,942 B2 | 2/2006 | Laird et al. |
| 7,036,928 B2 | 5/2006 | Schwebel |
| 7,060,061 B2 * | 6/2006 | Altshuler ............ A61B 18/203 606/2 |
| 7,069,084 B2 | 6/2006 | Yee |
| 7,108,694 B2 | 9/2006 | Miura et al. |
| 7,118,591 B2 | 10/2006 | Frank et al. |
| 7,122,013 B2 | 10/2006 | Liu |
| 7,122,047 B2 | 10/2006 | Grahn et al. |
| 7,123,968 B1 | 10/2006 | Casscells, III et al. |
| 7,211,070 B2 | 5/2007 | Soroudi |
| 7,229,468 B2 | 6/2007 | Wong et al. |
| 7,231,922 B2 * | 6/2007 | Davison ................ A61F 9/029 128/858 |
| D546,459 S | 7/2007 | Banryu |
| D552,736 S | 10/2007 | Yamaoka |
| D553,750 S | 10/2007 | Yamaoka |
| 7,316,657 B2 | 1/2008 | Kleinhenz et al. |
| 7,357,500 B2 | 4/2008 | Schwebel |
| 7,384,405 B2 | 6/2008 | Rhoades |
| 7,442,174 B2 | 10/2008 | Butler |
| 7,513,893 B2 | 4/2009 | Soroudi |
| 7,559,907 B2 | 7/2009 | Krempel et al. |
| 7,594,728 B2 | 9/2009 | Seal et al. |
| 7,637,878 B2 | 12/2009 | Lin |
| D612,941 S | 3/2010 | Youngquist et al. |
| D614,774 S | 4/2010 | Gausmann et al. |
| 7,712,899 B2 | 5/2010 | Tanassi et al. |
| 7,976,573 B2 * | 7/2011 | Korb ...................... A61F 7/12 128/898 |
| 7,981,145 B2 * | 7/2011 | Korb ...................... A61F 7/02 128/898 |
| 7,981,146 B2 * | 7/2011 | Korb ...................... A61F 7/12 128/898 |
| 7,981,147 B2 * | 7/2011 | Korb ...................... A61F 7/12 128/898 |
| 8,007,524 B2 * | 8/2011 | Korb ...................... A61F 7/12 128/898 |
| D645,565 S | 9/2011 | Smith et al. |
| 8,025,689 B2 * | 9/2011 | Korb .................. A61F 9/00772 128/898 |
| 8,083,787 B2 * | 12/2011 | Korb .................. A61F 9/00772 607/1 |
| 8,128,673 B2 | 3/2012 | Korb et al. |
| 8,128,674 B2 | 3/2012 | Korb et al. |
| 8,137,390 B2 | 3/2012 | Korb et al. |
| 8,187,310 B2 * | 5/2012 | Korb .................. A61F 9/00772 128/898 |
| 8,187,311 B2 | 5/2012 | Korb et al. |
| 8,262,715 B2 | 9/2012 | Wong et al. |
| 8,455,016 B2 | 6/2013 | Maskin |
| 8,617,229 B2 | 12/2013 | Korb et al. |
| 8,628,504 B2 | 1/2014 | Grenon et al. |
| 8,791,158 B2 | 7/2014 | Dalton et al. |
| 8,906,427 B2 | 12/2014 | Maskin |
| 8,915,253 B2 * | 12/2014 | Grenon ............... A61F 9/00772 128/898 |
| 8,950,405 B2 * | 2/2015 | Grenon .................. A61F 7/02 128/898 |
| 9,039,718 B2 | 5/2015 | Rynerson |
| 9,510,972 B2 | 12/2016 | Badawi |
| 2001/0041886 A1 | 11/2001 | Durkin et al. |
| 2002/0013572 A1 | 1/2002 | Berlin |
| 2002/0035345 A1 | 3/2002 | Beck |
| 2002/0099094 A1 | 7/2002 | Anderson |
| 2002/0111608 A1 | 8/2002 | Baerveldt et al. |
| 2002/0128696 A1 | 9/2002 | Pearl et al. |
| 2002/0156402 A1 | 10/2002 | Woog et al. |
| 2003/0050594 A1 | 3/2003 | Zamierowski |
| 2003/0056281 A1 | 3/2003 | Hasegawa |
| 2003/0065277 A1 | 4/2003 | Covington |
| 2003/0073987 A1 | 4/2003 | Sakurai et al. |
| 2003/0088241 A1 | 5/2003 | Hasegawa |
| 2003/0100936 A1 | 5/2003 | Altshuler et al. |
| 2003/0114426 A1 | 6/2003 | Pflugfelder et al. |
| 2003/0139790 A1 | 7/2003 | Ingle et al. |
| 2003/0195438 A1 | 10/2003 | Petillo |
| 2003/0211043 A1 | 11/2003 | Korb |
| 2003/0233135 A1 | 12/2003 | Yee |
| 2004/0064169 A1 | 4/2004 | Briscoe et al. |
| 2004/0064171 A1 | 4/2004 | Briscoe et al. |
| 2004/0076695 A1 | 4/2004 | Gilbard |
| 2004/0111138 A1 | 6/2004 | Bleam et al. |
| 2004/0153093 A1 | 8/2004 | Donovan |
| 2004/0199158 A1 | 10/2004 | Hood et al. |
| 2004/0237969 A1 | 12/2004 | Fuller |
| 2004/0249427 A1 | 12/2004 | Nabilsi |
| 2004/0260209 A1 | 12/2004 | Ella et al. |
| 2005/0022823 A1 | 2/2005 | Davison et al. |
| 2005/0119629 A1 | 6/2005 | Soroudi |
| 2005/0143798 A1 | 6/2005 | Bleam et al. |
| 2005/0187502 A1 | 8/2005 | Krempel et al. |
| 2005/0220742 A1 | 10/2005 | Breen |
| 2005/0234506 A1 | 10/2005 | Weser |
| 2006/0018953 A1 | 1/2006 | Guillon et al. |
| 2006/0030604 A1 | 2/2006 | Elsinger et al. |
| 2006/0055878 A1 | 3/2006 | Yee |
| 2006/0069420 A1 | 3/2006 | Rademacher et al. |
| 2006/0104914 A1 | 5/2006 | Soroudi |
| 2006/0135890 A1 | 6/2006 | Tsai |
| 2006/0136022 A1 | 6/2006 | Wong, Jr. et al. |
| 2006/0139569 A1 | 6/2006 | Schwebel |
| 2006/0154901 A1 | 7/2006 | Pflugfelder et al. |
| 2006/0157064 A1 | 7/2006 | Davison et al. |
| 2006/0183698 A1 | 8/2006 | Abelson |
| 2006/0212101 A1 | 9/2006 | Cheng |
| 2006/0233859 A1 | 10/2006 | Whitcup et al. |
| 2007/0016254 A1 | 1/2007 | Grenon et al. |
| 2007/0016256 A1 | 1/2007 | Korb et al. |
| 2007/0027411 A1 | 2/2007 | Ella et al. |
| 2007/0049913 A1 | 3/2007 | Grenon et al. |
| 2007/0060988 A1 | 3/2007 | Grenon et al. |
| 2007/0106349 A1 * | 5/2007 | Karni .................. A61B 18/042 607/101 |
| 2007/0129711 A1 * | 6/2007 | Altshuler ........... A45D 26/0061 606/9 |
| 2007/0173799 A1 | 7/2007 | Hsia |
| 2007/0203462 A1 | 8/2007 | Soroudi |
| 2007/0270760 A1 | 11/2007 | Dacquay et al. |
| 2007/0280924 A1 | 12/2007 | Daniels et al. |
| 2008/0051741 A1 | 2/2008 | Grenon et al. |
| 2008/0075787 A1 | 3/2008 | Hibino |
| 2008/0081999 A1 * | 4/2008 | Gravely .................. A61B 3/10 600/473 |
| 2008/0114423 A1 * | 5/2008 | Grenon ..................... A61F 7/12 607/96 |
| 2008/0132973 A1 | 6/2008 | Lord et al. |
| 2008/0188839 A1 * | 8/2008 | Chan .................... A61B 18/203 606/9 |
| 2008/0200848 A1 | 8/2008 | Avni |
| 2008/0221649 A1 * | 9/2008 | Echague ............. A61B 18/203 607/100 |
| 2008/0251085 A1 | 10/2008 | Schwebel |
| 2009/0043365 A1 | 2/2009 | Friedland et al. |
| 2009/0137533 A1 | 5/2009 | Adkins, Jr. |
| 2009/0149930 A1 * | 6/2009 | Schenck ................ A61B 18/14 607/100 |
| 2009/0192478 A1 | 7/2009 | Soroudi |

(56) References Cited

U.S. PATENT DOCUMENTS

| | | |
|---|---|---|
| 2009/0306111 A1 | 12/2009 | Nakamura et al. |
| 2009/0306607 A1 | 12/2009 | Yasuhiro |
| 2010/0087899 A1* | 4/2010 | Erez .............................. 607/101 |
| 2010/0100029 A1 | 4/2010 | Maskin |
| 2010/0292630 A1 | 11/2010 | Maskin |
| 2011/0022010 A1* | 1/2011 | Grenon ................ A61F 9/0008 604/294 |
| 2011/0039805 A1 | 2/2011 | Pflugfelder et al. |
| 2011/0059902 A1 | 3/2011 | Sullivan et al. |
| 2011/0059925 A1 | 3/2011 | Donnenfeld |
| 2011/0124725 A1 | 5/2011 | Maskin |
| 2011/0130729 A1* | 6/2011 | Korb .................. A61F 9/00772 604/294 |
| 2011/0172302 A1 | 7/2011 | Dalton et al. |
| 2011/0203832 A1 | 8/2011 | Schrock |
| 2011/0251532 A1 | 10/2011 | Yang |
| 2011/0273550 A1 | 11/2011 | Amano et al. |
| 2011/0294897 A1 | 12/2011 | Aberg et al. |
| 2012/0003296 A1 | 1/2012 | Shantha et al. |
| 2012/0065556 A1 | 3/2012 | Smith et al. |
| 2012/0093876 A1 | 4/2012 | Ousler, II et al. |
| 2012/0109041 A1 | 5/2012 | Munz |
| 2012/0128763 A1 | 5/2012 | Maskin |
| 2012/0209154 A1 | 8/2012 | Williams, III et al. |
| 2012/0220612 A1 | 8/2012 | Nakamura et al. |
| 2012/0321673 A1 | 12/2012 | Ogawa et al. |
| 2013/0045927 A1 | 2/2013 | Dana et al. |
| 2013/0046367 A1 | 2/2013 | Chen |
| 2013/0053733 A1 | 2/2013 | Korb et al. |
| 2013/0065867 A1 | 3/2013 | Smith et al. |
| 2013/0110101 A1 | 5/2013 | Van Valen et al. |
| 2013/0131171 A1 | 5/2013 | Maskin |
| 2013/0172790 A1 | 7/2013 | Badawi |
| 2013/0172829 A1 | 7/2013 | Badawi |
| 2014/0330129 A1 | 11/2014 | Grenon et al. |
| 2014/0378878 A1 | 12/2014 | Sharma et al. |
| 2015/0005750 A1 | 1/2015 | Kelleher et al. |
| 2015/0038851 A1 | 2/2015 | Hamrah et al. |
| 2015/0057701 A1 | 2/2015 | Kelleher et al. |
| 2015/0100001 A1 | 4/2015 | Bujak |
| 2015/0148711 A1 | 5/2015 | Bujak et al. |
| 2015/0174425 A1 | 6/2015 | Toyos et al. |
| 2015/0182415 A1 | 7/2015 | Olkowski et al. |
| 2015/0320590 A1 | 11/2015 | Whitehurst et al. |
| 2015/0320594 A1 | 11/2015 | Smith |
| 2016/0120692 A1 | 5/2016 | Chen |
| 2016/0120693 A1 | 5/2016 | Guillon et al. |
| 2016/0317379 A1 | 11/2016 | Mosaddegh |
| 2017/0014300 A1 | 1/2017 | Dippo et al. |
| 2017/0079834 A1 | 3/2017 | Badawi |
| 2017/0079842 A1 | 3/2017 | Maskin |

FOREIGN PATENT DOCUMENTS

| | | |
|---|---|---|
| CA | 2679448 A1 | 9/2008 |
| CA | 2787114 A1 | 7/2011 |
| CA | 2809274 A1 | 3/2012 |
| CN | 2650737 Y | 10/2004 |
| CN | 1631344 A | 6/2005 |
| CN | 2855388 Y | 1/2007 |
| CN | 102204854 A | 10/2011 |
| CN | 101663064 B | 3/2013 |
| CN | 103002737 A | 3/2013 |
| CN | 103108669 A | 5/2013 |
| CN | 102600008 B | 5/2014 |
| CN | 103816033 | 5/2014 |
| CN | 103948490 | 7/2014 |
| CN | 102697593 B | 12/2014 |
| CN | 102697595 B | 12/2014 |
| CN | 104203190 A | 12/2014 |
| CN | 104398234 A | 3/2015 |
| DE | 202005011496 U1 | 7/2006 |
| EP | 1816980 A2 | 8/2007 |
| EP | 2151438 A1 | 2/2010 |
| EP | 1587468 B1 | 1/2011 |
| EP | 2523556 A1 | 11/2012 |
| JP | 0370557 A | 3/1991 |
| JP | 06269473 A | 9/1994 |
| JP | 06315499 A | 11/1994 |
| JP | 10085248 A | 4/1998 |
| JP | 11221247 | 8/1999 |
| JP | 2000225141 A | 8/2000 |
| JP | 2001276113 A | 10/2001 |
| JP | 2002078727 A | 3/2002 |
| JP | 2004350803 A | 12/2004 |
| JP | U3112008 B | 7/2005 |
| JP | 2005237724 A | 9/2005 |
| JP | 2006198249 A | 8/2006 |
| JP | 2010155012 A | 7/2010 |
| JP | 2014205069 A | 10/2014 |
| KR | 20120115380 A | 10/2012 |
| MX | 2012008110 A | 10/2012 |
| WO | 9810723 A1 | 3/1998 |
| WO | 9920213 A1 | 4/1999 |
| WO | 9958131 A1 | 11/1999 |
| WO | 2004041134 A1 | 5/2004 |
| WO | 2006058189 A2 | 6/2006 |
| WO | 2006093851 A2 | 9/2006 |
| WO | 2008024100 A2 | 2/2008 |
| WO | 2008106228 A2 | 9/2008 |
| WO | 2009064834 A2 | 5/2009 |
| WO | 2010005527 A1 | 1/2010 |
| WO | 2010056848 A1 | 5/2010 |
| WO | 2011085385 A1 | 7/2011 |
| WO | 2012036931 A1 | 3/2012 |
| WO | 2012051313 A2 | 4/2012 |
| WO | 2013003594 A3 | 1/2013 |
| WO | 2013003731 A3 | 1/2013 |
| WO | 2013006574 A1 | 1/2013 |
| WO | 2013036894 A2 | 3/2013 |
| WO | 2013114127 A1 | 8/2013 |
| WO | 2013126599 A1 | 8/2013 |
| WO | 2013149318 A1 | 10/2013 |
| WO | 2013166353 A1 | 11/2013 |
| WO | 2014049841 A1 | 4/2014 |
| WO | 2014158356 A1 | 10/2014 |
| WO | 2014179356 A1 | 11/2014 |
| WO | 2014179795 A2 | 11/2014 |
| WO | 2015163821 A1 | 10/2015 |
| WO | 2016070134 A1 | 5/2016 |

OTHER PUBLICATIONS

No Author, "New Over-the-Counter Dry Eye Drop Now Available to Help Estimated 40 Percent of Americans Who Suffer from Occasional or Chronic Dry Eye", Business Wire News Release, Mar. 31, 2008, accessed Jun. 5, 2008, 4 pages.

Akyol-Salman, Ilknur et al., "Efficacy of Topical N-Acetylcysteine in the Treatment of Meibomian Gland Dysfunction," Journal of Ocular Pharmacology and Therapeutics, vol. 26, No. 4, Aug. 1, 2010, pp. 329-333.

Aronowicz, JD et al. "Short Term Oral Minocycline Treatment of Meibomiantis," Br. J. Ophthalmol, vol. 90, No. 7, Jul. 2006, pp. 856-860.

Blackie, Caroline A. et al., "Inner Eyelid Surface Temperature as a Function of Warm Compress Methodology," Optometry and Vision Science, vol. 85, No. 8, Aug. 2008, pp. 675-683.

Blackie, Caroline A. et al., "Nonobvious Obstructive Meibomian Gland Dysfunction," Cornea, vol. 29, No. 12, Dec. 2010, pp. 1333-1345.

Blackie, Caroline A. et al., "Recovery Time of an Optimally Secreting Meibomian Gland," Cornea, vol. 28, No. 3, Apr. 2009, pp. 293-297.

Butovich, Igor et al., "Meibomian Lipid Films and the Impact of Temperature," Investigative Opthalmology & Visual Science, vol. 51, No. 11, Jul. 2010, pp. 5508-5518.

Cunniffe, M. Geraldine et al., "Topical Antiglaucoma Treatment with Prostaglandin Analogues May Precipitate Meibomian Gland Disease," Ophthalmic Plastic and Reconstructive Surgery, Sep.-Oct. 2011, vol. 27, No. 5, Lippincott Williams and Wilkins, Philadelphia, PA, p. 128-129.

(56) References Cited

OTHER PUBLICATIONS

Dausch, Eva et al., "Dry Eye Syndrome in Women's Health and Gynecology: Etiology, Pathogenesis and Current Therapeutic Strategies," Geburtshilfe und Frauenheilkunde, vol. 70, No. 9, Jan. 1, 2010, pp. 707-711. (Abstract Only).
Donnenfeld, Eric et al., "Topical Ophthalmic Cyclosporine: Pharmacology and Clinical Uses," Survey of Ophthalmology, vol. 54, No. 3, May/Jun. 2009, pp. 321-338.
Foulks, Gary N. et al., "Topical Azithromycin Therapy for Meibomian Gland Dysfunction: Clinical Response and Lipid Alterations," Cornea, vol. 29, No. 7, Jul. 2010, pp. 781-788.
Foulks, Gary N. et al., "Meibomian Gland Dysfunction: The Past, Present, and Future," Eye and Contact Lens, vol. 36, No. 5, Sep. 2010, pp. 249-253.
Friedland, B., et al., "A Novel Thermodynamic Treatment for Meibomian Gland Dysfunction," Current Eye Research, vol. 36, No. 2, Feb. 2011, pp. 79-87.
Geerling, G., et al., "The international workshop on meibomian gland dysfunction: report of the subcommittee on management and treatment of meibomian gland dysfunction," Mar. 2011, Investigative Ophthalmology & Visual Science, vol. 52, No. 4., pp. 2050-2064.
Goto, E., et al. "Treatment of Non-Inflamed Obstructive Meibomian Gland Dysfunction by an Infrared Warm Compression Device," Br. J. Ophthalmology, vol. 86, Dec. 2002, pp. 1403-1407.
Goto, Eiki, et al., "Tear Evaporation Dynamics in Normal Subjects and Subjects with Obstructive Meibomian Gland Dysfunction," Investigative Ophthalmology & Visual Science, vol. 44, No. 2, Feb. 2003, pp. 533-539.
Greiner, J., "A Single LipiFlow Thermal Pulsation System Treatment Improves Meibomian Gland Function and Reduces Dry Eye Symptoms for 9 months," Current Eye Research, vol. 37 No. 4, Apr. 2012, pp. 272-278.
Gupta, S. et al. "Docetaxel-Induced Meibomian Duct Inflammation and Blockage Leading to Chalazion Formation," Prostate Cancer and Prostatic Diseases, vol. 10, No. 4, Apr. 2007, pp. 396-397.
Haque, Reza M. et al., "Multicenter Open-label Study Evaluating the Efficacy of Azithromycin Opthalmic Solution 1% on the Signs and Symptoms of Subjects with Blepharitis," Cornea, vol. 29, No. 8, Aug. 2010, pp. 871-877.
Holifield, Karintha and Lazzaro, Douglas R., "Case report: Spontaneous stenotrophomonas maltophilia keratitis in a diabetic patient," Eye and Contact Lens, Sep. 2011, vol. 37, No. 5, Philadelphia PA, pp. 326-327.
Knop, E. et al., "Meibomian Glands: Part III—Dysfunction—Argument for a Discrete Disease Entity and as an Important Cause of Dry Eye," Ophthalmologe, vol. 106, No. 11, Nov. 2009, pp. 966-979. (Abstract Only).
Knop, E. et al., "Meibomian Glands: Part IV—Functional Interactions in the Pathogenesis of Meibomian Gland Dysfunction (MGD)," Ophthalmologe, vol. 106, No. 11, Nov. 2009, pp. 980-987. (Abstract Only).
Kokke, K.H. et al., "Oral Omega-6 Essential Fatty Acid Treatment in Contact Lens Associated Dry Eye," Contact Lens and Anterior Eye, vol. 31, No. 3, Jun. 2008, pp. 141-146.
Korb, Donald et al., "The Effect of Two Novel Lubricant Eye Drops on Tear Film Lipid Layer Thickness in Subjects with Dry Eye Symptoms," Optom. Vis. Sci., vol. 82, No. 7, 2005, pp. 594-601.
Korb, Donald R. and Blackie, Caroline A., "Meibomian gland therapeutic expression: Quantifying the applied pressure and the limitation of resulting pain," Eye and Contact Lens, Sep. 2011, vol. 37, No. 5, Philadelphia, PA, pp. 298-301.
Korb, Donald R. et al., "Increase in Tear Film Lipid Layer Thickness Following Treatment of Meibomian Gland Dysfunction", Lacrimal Gland, Tear Film & Dry Eye Syndromes, vol. 350, Plenum Press, 1994, pp. 293-298.
Korb, Donald R. et al., "Lid Wiper Epitheliopathy and Dry Eye Symptoms," Eye & Contact Lens, vol. 31, No. 1, Jan. 2005, pp. 2-8.
Korb, Donald R. et al., "Restoration of Meibomian Gland Functionality with Novel Thermodynamic Treatment Device—A Case Report," Cornea, vol. 29, No. 8, Aug. 2010, pp. 930-933.
Korb, Donald R. et al., "Tear Film Lipid Layer Thickness as a Function of Blinking," Cornea, vol. 13, No. 4, Jul. 1994, pp. 354-359.
Korb, Donald R. et al., Slide entitled "Inner Eyelid Surface Temperature as a Function of Warm Compress Methodology," from presentation entitled "The Greatest Anterior Segment Disease and Contact Lens Complications Course," AOA Meeting, Seattle, Washington, Jun. 27, 2008, 2 pages.
Korb, Donald R., O.D., et al., "Meibomian Gland Dysfunction and Contact Lens Intolerance," Journal of the American Optometric Association, vol. 51, No. 3, Mar. 1980, pp. 243-251.
Korb, Donald R., Slide entitled "Inner Eyelid Surface Temperature as a Function of Warm Compress Methodology," from presentation entitled "The Tear Film and Dry Eye States a Fertile Research Area," University of California at Berkeley, School of Optometry, Apr. 11, 2008. 2 pages.
Kuscu, Naci Kemal, et al., "Tear Function Changes of Postmenopausal Women in Response to Hormone Replacement Therapy," Maturitas, vol. 44, Jan. 2003pp. 63-68.
Lane, S. et al., "A New System, the LipiFlow, for the Treatment of Meibomian Gland Dysfunction," Cornea, vol. 31, No. 4, Apr. 2012, pp. 396-404.
Lemp, Michael A. et al., "Blepharitis in the United States 2009: A Survey-Based Perspective on Prevalence and Treatment." Oculular Surface, vol. 7, No. 2 Supplement, Apr. 2009, 36 pages.
Lemp, Michael A., et al., "The Therapeutic Role of Lipids—Managing Ocular Surface Disease," Supplement to Refractive Eyecare of Ophthalmologists, vol. 9, No. 6, Jun. 2005, 14 pages.
Maskin, Steven L., "Intraductal Meibomian Gland Probing Relieves Symptoms of Obstructive Meibomian Gland Dysfunction," Cornea, vol. 29, No. 10, Oct. 2010, pp. 1145-1152.
Matsumoto, Yukihiro et al., "The Evaluation of the Treatment Response in Obstructive Meibomian Gland Disease by In Vivo Laser Confocal Microscopy," Graefes Arch Clin Exp Ophthalmol, vol. 247, No. 6, Jun. 2009, pp. 821-829.
Unknown, "Introducing: Thermofoil Heaters", Minco Bulletin HS-202, 2002, 9 pages.
Mitra, M. et al., "Tear Film Lipid Layer Thickness and Ocular Comfort after Meibomian Therapy via Latent Heat with a Novel Device in Normal Subjects," Eye, Jun. 2005, pp. 657-660.
Mori, A., et al., "Efficacy of the Treatment by the Disposable Eyelid Warming Instrument for Meibomian Gland Dysfunction," Poster Presentation, Hall A, The Association for Research and Vision in Ophthalmology Annual Meeting, Fort Lauderdale, Florida, Apr. 30, 2000, 1 page.
Mori, Asako, et al., "Disposable Eyelid-Warming Device for the Treatment of Meibomian Gland Dysfunction", Japan Journal of Ophthalmology, vol. 47, pp. 578-586, 2003.
Olson, Mary Catherine, B.A., et al., "Increase in Tear Film Lipid Layer Thickness Following Treatment with Warm Compresses in Patients with Meibomian Gland Dysfunction," Eye & Contact Lens, vol. 29, No. 2, Apr. 2003, pp. 96-99.
Paugh, J.R. et al., "Meibomian Therapy in Problematic Contact Lens Wear," Entrez PubMed, Optom Vis Sci, vol. 67, No. 11, Nov. 1990, pp. 803-806 (abstract only).
Paugh, Jerry R. et al., "Precorneal Residence Time of Artificial Tears Measured in Dry Eye Subjects," Optometry and Vision Science, vol. 85, No. 8, Aug. 2008, pp. 725-731.
Romero, Juan M., et al., "Conservative Treatment of Meibomian Gland Dysfunction," Contact Lens Association of Ophthalmology, Eye & Contact Lens, vol. 30, No. 1, Jan. 2004, pp. 14-19.
Sullivan, Benjamin D., et al., "Impact of Antiandrogen Treatment on the Fatty Acid Profile of Neutral Lipids in Human Meibomian Gland Secretions," Journal of Clinical Endocrinology & Metabolism, vol. 85, No. 12, Dec. 2000, pp. 4866-4873.
Sullivan, David et al., "Do Sex Steroids Exert Sex-Specific and/or Opposite Effects on Gene Expression in Lacrimal and Meibomian Glands?" Molecular Vision, vol. 15, No. 166, Aug. 10, 2009, pp. 1553-1572.

(56) References Cited

OTHER PUBLICATIONS

Suzuki, Tomo et al., "Estrogen and Progesterone Control of Gene Expression in the Mouse Meibomian Gland," Invest. Ophthalmol. Vis. Sci., vol. 49, No. 5, May 2008, pp. 1797-1818.
Tobler, David, et al., "Nanotech Silver Fights Microbes in Medical Devices," Medical Device and Diagnostic Industry, May 1, 2005, p. 164.
Toyos, Rolando, "Intense Pulsed Light for Dry Eye Syndrome," Cataract & Refractive Surgery Today, Apr. 2009, pp. 1-3.
Wolff, Eugene, "Eugene Wolff's Anatomy of the eye and orbit : including the central connexions, development, and comparative anatomy of the visual apparatus (book)," 1976, p. 170.
Unknown, "IFU Manual for PNT Model 1000—Rev H," Feb. 11, 2009, http://www.oi-pnt.com/files/IFU_Manual_Model_1000_English_with_Bargode_Rev_H.pdf, 24 pages.
Unknown, "TearScience Launches Breakthrough Technology in Canada to Address the Root Cause of Evaporative Dry Eye," Business Wire, Jun. 9, 2011, http://www.businesswire.com/news/home/20110609005860/en/TearScience-Launches-Breakthrough-Technology-Canada-Address-Root, 2 pages.
Vasta, Stephanie, "Aggressive Treatments Developed for Meibomian Gland Dysfunction," Primary Care Optometry News, Nov. 1, 2009, 3 pages.
Wang, Y. et al., "Baseline Profiles of Ocular Surface and Tear Dynamics After Allogeneic Hematopoietic Stem Cell Transplantation in Patients With or Without Chronic GVHD-Related Dry Eye," Bone Marrow Transplantation, vol. 45, No. 6, Jun. 2010, pp. 1077-1083.
Korb, D. et al., "Meibomian gland therapeutic expression: quantifying the applied pressure and the limitation of resulting pain," Eye & Contact Lens, vol. 37 No. 5, Sep. 2011, pp. 298-301.
Akyol-Salman, I. et al., "Comparison of the efficacy of topical N-acetyl-cysteine and a topical steroid-antibiotic combination therapy in the treatment of meibomian gland dysfunction," Journal of Ocular Pharmacology and Therapeutics, vol. 28 No. 1, Feb. 2, 2012, pp. 49-52.
No Author, "TearScience's LipiFlow Multi-center Clinical Study Shows Improved Meibomian Gland Secretions and Dry Eye Symptoms," Business Wire, Mar. 5, 2012, 2 pages.
Non-Final Rejection for U.S. Appl No. 11/434,033 mailed Jan. 24, 2011, 7 pages.
Non-final Office Action for U.S. Appl No. 11/434,033 mailed Aug. 12, 2011, 8 pages.
Non-final Office Action for U.S. Appl No. 11/931,398 mailed Jan. 27, 2012, 4 pages.
Advisory Action for U.S. Appl No. 11/434,446 mailed Mar. 4, 2010, 2 pages.
Final Rejection for U.S. Appl No. 11/434,446 mailed Dec. 23, 2009, 16 pages.
Non-final Rejection for U.S. Appl No. 11/434,446 mailed Apr. 9, 2010, 17 pages.
Non-Final Rejection for U.S. Appl No. 11/434,446 mailed Jun. 17, 2009, 13 pages.
English translation of Official Action issued May 10, 2011, for Japanese Patent Application No. 2009-525529, 3 pages.
Notice of Allowance for U.S. Appl No. 13/025,951 mailed Mar. 28, 2012, 8 pages.
Non-final Office Action for U.S. Appl No. 13/025,951 mailed Oct. 25, 2011, 9 pages.
Notice of Allowance for U.S. Appl No. 13/025,990 mailed Mar. 28, 2012, 9 pages.
Non-final Office Action for U.S. Appl No. 13/025,990 mailed Oct. 25, 2011, 11 pages.
Notice of Allowance for U.S. Appl No. 11/434,054 mailed Oct. 18, 2011, 9 pages.
Non-final Office Action for U.S. Appl No. 11/434,054 mailed May 26, 2011, 7 pages.
Non-final Office Action for U.S. Appl No. 11/434,054 mailed Sep. 8, 2010, 7 pages.
Non-final Office Action for U.S. Appl No. 11/434,054 mailed Mar. 12, 2010, 7 pages.
Notice of Allowance for U.S. Appl No. 12/821,183 mailed Jul. 29, 2011, 8 pages.
Non-final Office Action for U.S. Appl No. 12/821,183 mailed May 26, 2011, 8 pages.
Non-final Office Action for U.S. Appl No. 12/821,183 mailed Dec. 21, 2010, 7 pages.
Notice of Allowance for U.S. Appl No. 11/541,291 mailed May 26, 2011, 7 pages.
Notice of Allowance for U.S. Appl No. 11/541,291 mailed Jan. 10, 2011, 6 pages.
Final Office Action for U.S. Appl No. 11/541,291 mailed Aug. 17, 2010, 6 pages.
Non-final Office Action for U.S. Appl No. 11/541,291 mailed Jun. 2, 2010, 10 pages.
Advisory Action for U.S. Appl No. 11/541,291 mailed Mar. 30, 2010, 3 pages.
Final Office Action for U.S. Appl No. 14/541,291 mailed Dec. 16, 2009, 11 pages.
Non-final Office Action for U.S. Appl No. 11/541,291 mailed May 19, 2009, 11 pages.
Notice of Allowance for U.S. Appl No. 11/931,646 mailed Aug. 5, 2010, 6 pages.
Advisory Action for U.S. Appl No. 11/931,646 mailed Mar. 30, 2010, 3 pages.
Final Office Action for U.S. Appl No. 11/931,646 mailed Dec. 15, 2009, 11 pages.
Non-final Office Action for U.S. Appl No. 11/931,646 mailed May 19, 2009, 11 pages.
Notice of Allowance for U.S. Appl No. 11/541,418 mailed May 26, 2011, 7 pages.
Advisory Action for U.S. Appl No. 11/541,418 mailed Apr. 6, 2011, 3 pages.
Final Office Action for U.S. Appl No. 11/541,418 mailed Mar. 10, 2011, 21 pages.
Non-final Office Action for U.S. Appl No. 11/541,418 mailed Jul. 12, 2010, 20 pages.
Notice of Allowance for U.S. Appl No. 12/015,558 mailed Jun. 1, 2011, 8 pages.
Non-final Office Action for U.S. Appl No. 12/015,558 mailed Aug. 13, 2010, 9 pages.
Non-final Office Action for U.S. Appl No. 11/928,681 mailed Feb. 2, 2012, 4 pages.
Notice of Allowance for U.S. Appl No. 29/303,312 mailed Mar. 1, 2010, 7 pages.
Notice of Allowance for U.S. Appl No. 29/303,314 mailed Feb. 5, 2010, 6 pages.
Final Office Action for U.S. Appl No. 29/303,314 mailed Dec. 28, 2009, 6 pages.
Notice of Allowance for U.S. Appl. No. 29/303,317 mailed Feb. 1, 2010, 8 pages.
Non-final Office Action for U.S. Appl. No. 29/303,317 mailed Sep. 1, 2009, 10 pages.
Notice of Allowance for U.S. Appl. No. 12/015,567 mailed May 20, 2011, 8 pages.
Non-final Office Action for U.S. Appl. No. 12/015,567 mailed Aug. 16, 2010, 9 pages.
Non-final Office Action for U.S. Appl. No. 12/015,576 mailed Jul. 19, 2010, 11 pages.
Notice of Allowance for U.S. Appl. No. 12/015,584 mailed Jul. 8, 2011, 4 pages.
Notice of Allowance for U.S. Appl. No. 12/015,584 mailed Jun. 29, 2011, 7 pages.
Final Office Action for U.S. Appl. No. 12/015,584 mailed May 27, 2011, 7 pages.
Non-final Office Action for U.S. Appl. No. 12/015,584 mailed Aug. 23, 2010, 9 pages.
Non-final Office Action for U.S. Appl. No. 12/015,600 mailed Mar. 19, 2012, 6 pages.
Notice of Allowance for U.S. Appl. No. 12/015,675 mailed Oct. 26, 2011, 9 pages.

(56) References Cited

OTHER PUBLICATIONS

Non-final Office Action for U.S. Appl. No. 12/015,675 mailed May 10, 2011, 7 pages.
Notice of Allowance for U.S. Appl. No. 12/015,683 mailed Oct. 26, 2011, 8 pages.
Non-final Office Action for U.S. Appl. No. 12/015,683 mailed May 6, 2011, 14 pages.
Notice of Allowance for U.S. Appl. No. 12/015,721 mailed Nov. 30, 2011, 8 pages.
Advisory Action for U.S. Appl. No. 12/015,721 mailed Aug. 31, 2011, 3 pages.
Final Office Action for U.S. Appl. No. 12/015,721 mailed Jun. 8, 2011, 12 pages.
Non-final Office Action for U.S. Appl. No. 12/015,721 mailed Jan. 5, 2011, 12 pages.
Notice of Allowance for U.S. Appl. No. 29/344,914 mailed Mar. 7, 2011, 8 pages.
Notice of Allowance for U.S. Appl. No. 29/344,914 mailed Jan. 12, 2011, 7 pages.
English translation of Japanese Office Action for patent application 2009-525536 mailed Jan. 10, 2012, 6 pages.
International Search Report for PCT/US07/00493 mailed Oct. 1, 2007, 1 page.
English translation of First Office Action for Chinese patent application 200780039253.8 mailed Jul. 12, 2010, 6 pages.
Extended European Search Report for PCT/US2007/000525 mailed Sep. 20, 2010, 9 pages.
English translation of Japanese Office Action for patent application 2009-544825 mailed Jan. 10, 2012, 9 pages.
International Search Report for PCT/US07/00525 mailed Dec. 3, 2007, 12 pages.
Extended European Search Report for patent application 07716445-1269 mailed Apr. 7, 2011, 9 pages.
English translation of Japanese Office Action for patent application 2009-525537 mailed Jan. 10, 2012, 4 pages.
International Search Report for PCT/US07/00508 mailed Nov. 2, 2007, 1 page.
English translation of Second Chinese Office Action for patent application 200880008741.7 mailed Mar. 29, 2012, 7 pages.
English translation of First Chinese Office Action for patent application 200880008741.7 mailed Jul. 20, 2011, 7 pages.
Office Action for Israeli patent application 199920 mailed May 22, 2011, 2 pages.
International Search Report for PCT/US08/51309 mailed May 20, 2008, 1 page.
English translation of First Office Action for Chinese patent application 200680056181.3 mailed Jun. 12, 2010, 6 pages.
International Search Report for PCT/US06/32544 mailed May 12, 2008, 8 pages.
Notice of Allowance for U.S. Appl. No. 12/015,576 mailed May 20, 2011, 8 pages.
Final Office Action for U.S. Appl. No. 11/434,033 mailed Mar. 15, 2012, 9 pages.
Finis, D. et al., "Meibom-Drusen-Dysfunktion," Klinische Monatsblatter fur Augenheilkunde, vol. 229, No. 5, Mar. 2012, pp. 506-513 (Abstract translated only).
Non-final Office Action for U.S. Appl. No. 13/183,901 mailed Jun. 4, 2012, 46 pages.
Korb, et al., "Prevalence of lid wiper epitheliopathy in subjects with dry eye signs and symptoms," Cornea, vol. 29, No. 4, Apr. 2012, pp. 377-383.
Second Office Action for Japanese patent application 2009-525529 mailed Jun. 5, 2012, 8 pages.
Extended European Search Report for patent application 07716441.6 mailed Sep. 4, 2012, 7 pages.
Foulks, G. et al., Comparative Effectiveness of Azithromycin and Doxycycline in Therapy of Meibomian Gland Dysfunction, ARVO Annual Meeting, May 2011, pp. 3816 (Abstract only).
Korb, et al., "Restoration of meibomian gland function post Lipiflow treatment," ARVO Annual Meeting, May 2011, pp. 3818 (Abstract only).
Maskin, S. et al., "Intraductal Meibomian Gland Probing with Adjunctive Intraductal Microtube Steriod Injection (MGPs) for Meibomian Gland Dysfuction," ARVO Annual Meeting, May 2011, pp. 3817 (Abstract only).
McCann, L. et al., "Effect of First Line Management Therapies on Dry Eye Disease," ARVO Annual Meeting, May 2011, pp. 3829 (Abstract only).
Willis, et al., Meibomian gland function, lid wiper epitheliopathy, and dry eye symptoms, ARVO Annual Meeting, May 2011, pp. 3740 (Abstact only).
Non-final Office Action for U.S. Appl. No. 13/368,976 mailed Aug. 31, 2012, 10 pages.
Non-final Office Action for U.S. Appl. No. 11/541,308 mailed Aug. 31, 2012, 20 pages.
Non-final Office Action for U.S. Appl. No. 13/242,068 mailed Aug. 29, 2012, 9 pages.
Non-final Office Action for U.S. Appl. No. 13/367,908 mailed Sep. 13, 2012, 11 pages.
Asbell, P. et al. "The international workshop on meibomian gland dysfunction: report of the clinical trials subcommittee," Investigative Ophthalmology and Visual Science, Mar. 2011, pp. 2065-2085.
Office Action for Japanese patent application 2009-546506 mailed Sep. 4, 2012, 6 pages.
Foulks et al., "Improving awareness, identification, and management of meibomian gland dysfunction," Ophthalmology, vol. 119, No. 10 Sup., Oct. 2012, 12 pages.
Arita, F. et al., "Comparison of the long-term effects of various topical antiglaucoma medications on meibomian glands," Cornea, vol. 31, No. 11, Nov. 2012, pp. 1229-1234.
Non-final Office Action for U.S. Appl. No. 11/931,398 mailed Nov. 2, 2012, 8 pages.
European Search Report for patent application 06801969.4 mailed Nov. 5, 2012, 4 pages.
Examination Report for Indian patent application 563/MUMNP/2009 mailed Oct. 31, 2012, 1 page.
Non-final Office Action for U.S. Appl. No. 11/928,681 mailed Nov. 20, 2012, 10 pages.
Pucker, A. et al., "Analysis of Meibum and Tear Lipids," The Ocular Surface, vol. 10, No. 4, Oct. 2012, pp. 230-250.
Author Unknown, Definition of Platform, Macmillan Dictionary, accessed Dec. 10, 2012, 2 pages, http://www.macmillandictionary.com/dictionary/british/platform.
Author Unknown, Definition of Platform, Merriam-Webster Dictionary, accessed Dec. 10, 2012, 3 pages, http://www.merriam-webstercom/dictionary/platform.
Author Unknown, Definition of On, Merriam-Webster Dictionary, accessed Dec. 14, 2012, 5 pages, http://www.merriam-webster.com/dictionary/on.
Final Rejection mailed Dec. 27, 2012, for U.S. Appl. No. 13/183,901, 10 pages.
Non-Final Rejection mailed Dec. 27, 2012, for U.S. Appl. No. 12/015,593, 27 pages.
Non-Final Rejection mailed Jan. 4, 2013, for U.S. Appl. No. 12/015,600, 8 pages.
Examination Report issued Oct. 17, 2012, for European Application No. 07716444.0, 5 pages.
Examination Report issued Nov. 16, 2012, for European Application No. 06801969.4, 6 pages.
International Search Report mailed Jan. 7, 2013, for PCT/US12/44650, 44 pages.
Author Unknown, "New Breakthrough Treatment for Evaporative Dry Eye Disease Introduced by Dry Eye Specialist, Mark R. Mandel, M.D.," PR Newswire, Dec. 11, 2012, 2 pages, Hayward, California.
Cuevas, Miguel et al., "Correlations Among Symptoms, Signs, and Clinical Tests in Evaporative-Type Dry Eye Disease Caused by Meibomian Gland Dysfunction (MGD)," Current Eye Research, vol. 37, No. 10, Oct. 2012, pp. 855-863.

(56) References Cited

OTHER PUBLICATIONS

Suzuki, Tomo, "Meibomitis-Related Keratoconjunctivitis: Implications and Clinical Significance of Meibomian Gland Inflammation," Cornea, vol. 31, Supplemental Issue, Nov. 2012, pp. S41-S44.
Non-Final Rejection for U.S. Appl. No. 11/928,681, mailed Nov. 20, 2012, 9 pages.
Final Rejection for U.S. Appl. No. 13/242,068, mailed Feb. 14, 2013, 10 pages.
Examination Report for Indian Patent Application No. 564/MUMNP/2009, issued Jan. 30, 2013, 1 page.
European Search Report for European Patent Application No. 08727830.5 issued Dec. 20, 2012, 3 pages.
Examination Report for European Patent Application No. 08727830.5 issued Jan. 15, 2013, 5 pages.
Yoshitomi, et al., "Meibomian Gland Compressor and Cataract Surgery," New Ophthalmology, Japan, 2001, vol. 18, No. 3, pp. 321-323.
English translation of Final Japanese Office Action for patent application 2009-525537 mailed Jan. 29, 2013, 4 pages.
English translation of Final Japanese Office Action for patent application 2009-544825 mailed Jan. 29, 2013, 4 pages.
Agnifili et al., "In vivo confocal microscopy of meibomian glands in glaucoma," British Journal of Ophthalmology, vol. 97, No. 3, Mar. 2013, pp. 343-349, United Kingdom.
Khandelwal, et al., "Androgen regulation of gene expression in human meibomian gland and conjunctival epithelial cells," Molecular Vision, vol. 18, Apr. 27, 2012, pp. 1055-1067.
Final Office Action for U.S. Appl. No. 11/541,308 mailed Mar. 19, 2013, 25 pages.
Final Office Action for U.S. Appl. No. 11/928,681 mailed Feb. 26, 2013, 7 pages.
Advisory Action for U.S. Appl. No. 13/183,901 mailed Mar. 11, 2013, 3 pages.
Final Office Action for U.S. Appl. No. 13/368,976 mailed Mar. 11, 2013, 8 pages.
Final Office Action for U.S. Appl. No. 13/242,068 mailed Feb. 14, 2013, 10 pages.
Final Office Action for U.S. Appl. No. 13/367,865 mailed Mar. 4, 2013, 7 pages.
Final Office Action for U.S. Appl. No. 13/367,908 mailed Feb. 27, 2013, 7 pages.
Final Office Action for U.S. Appl. No. 11/931,398 mailed Mar. 4, 2013, 7 pages.
Advisory Action for U.S. Appl. No. 11/928,681 mailed May 3, 2013, 3 pages.
Advisory Action for U.S. Appl. No. 11/931,398 mailed May 15, 2013, 2 pages.
Advisory Action for U.S. Appl. No. 13/367,908 mailed May 22, 2013, 3 pages.
Notice of Allowance for U.S. Appl. No. 13/367,865 mailed May 23, 2013, 9 pages.
Examination Report for Indian Patent Application No. 555/MUMNP/2009, issued Apr. 15, 2013, 1 page.
Korb, et al., "Forceful Meibomian Gland Expression with a Standardized Force of 8 PSI in Patients with Obstructive Meibomian Gland Dysfunction," ARVO Annual Meeting, Poster Session, Program No. 3819, Poster Board No. D952, May 3, 2011, 2 pages (Abstract Only).
Advisory Action for U.S. Appl. No. 11/541,308 mailed Jun. 26, 2013, 3 pages.
Non-final Office Action for U.S. Appl. No. 12/887,165 mailed Apr. 10, 2013, 13 pages.
Translation of Notice of Rejection for Japanese Patent Application No. 2009-525529 mailed May 14, 2013, 5 pages.
Arita, R. et al., "Topical diquafosol for patients with obstructive meibomian gland dysfunction," British Journal of Ophthalmology, vol. 97, No. 6, Jun. 2013, pp. 725-729.
Greiner, J., "Long-term 12-month improvement in meibomian gland function and reduced dry eye symptoms with a single thermal pulsation treatment," Clinical and Experimental Ophthalmology, vol. 41, No. 6, Aug. 2013, pp. 524-530.
Her, Y. et al., "Dry eye and tear film functions in patients with psoriasis," Japanese Journal of Ophthalmology, vol. 57, No. 4, Jul. 2013, pp. 341-346.
Li, Li-Hu et al., "Analysis of the efficacy in the treatment of meibomian gland dysfunction," International Eye Science, vol. 13, No. 7, Jul. 2013, pp. 1495-1497.
Tang, Qin et al., "Clinical analysis of meibomian gland dysfunction in elderly patients," International Eye Science, vol. 13, No. 7, Jul. 2013, pp. 1419-1423.
Zhang et al., "Efficacy of physical therapy meibomian gland dysfunction," International Eye Science, International Journal of Ophthalmology, vol. 13, No. 6, Jun. 2013, pp. 1267-1268.
Non-final Office Action for U.S. Appl. No. 12/015,600 mailed Aug. 5, 2013, 8 pages.
Notice of Allowance for U.S. Appl. No. 12/887,165 mailed Sep. 3, 2013, 10 pages.
Advisory Action for U.S. Appl. No. 13/368,976 mailed Jul. 10, 2013, 3 pages.
Non-final Office Action for U.S. Appl. No. 13/242,068 mailed Jul. 3, 2013, 7 pages.
Notice of Allowance for U.S. Appl. No. 13/367,908 mailed Aug. 19, 2013, 8 pages.
Notice of Allowance for U.S. Appl. No. 13/368,976 mailed Aug. 30, 2013, 9 pages.
Final Office Action for U.S. Appl. No. 12/015,593 mailed Oct. 3, 2013, 21 pages.
Non-final Office Action for U.S. Appl. No. 13/183,901 mailed Oct. 4, 2013, 10 pages.
Notice of Allowance for U.S. Appl. No. 13/242,068 mailed Nov. 12, 2013, 10 pages.
Advisory Action for U.S. Appl. No. 12/015,593 mailed Dec. 13, 2013, 3 pages.
International Preliminary Report on Patentability for PCT/US2012/044650 mailed Jan. 16, 2014, 41 pages.
First Office Action for Chinese patent application 201210077169.8 mailed Nov. 26, 2013, 18 pages.
First Office Action for Chinese patent application 201210077192.7 mailed Nov. 22, 2013, 12 pages.
Liu, Ze-Yuan et al., "Treatment of dry eye caused by meibomian gland dysfunction," International Eye Science, vol. 14, No. 2, Feb. 2014, pp. 270-272.
Non-final Office Action for U.S. Appl No. 11/434,033 mailed Feb. 19, 2014, 10 pages.
Examiner's Decision of Rejection for Japanese Patent Application No. 2009-544825 mailed Jan. 7, 2014, 6 pages.
Examiner's Decision of Rejection for Japanese Patent Application No. 2009-525537 mailed Jan. 7, 2014, 6 pages.
Final Office Action for U.S. Appl. No. 13/183,901 mailed Feb. 3, 2014, 10 pages.
Lu, Hui et al., "Tear film measurement by optical reflectometry technique," Journal of Biomedical Optics, vol. 19, No. 2, Feb. 2014, 8 pages.
Non-final Office Action for U.S. Appl. No. 12/015,593 mailed Mar. 14, 2014, 19 pages.
First Office Action for Chinese patent application 201210127347.3 mailed Jan. 15, 2014, 13 pages.
Purslow, Christine, "Evaluation of the ocular tolerance of a novel eyelid-warming device used for meibomian gland dysfunction," Contact Lens & Anterior Eye, vol. 36, No. 5, Elsevier Ltd., Oct. 2013, pp. 226-231.
Final Office Action for U.S. Appl. No. 12/015,600 mailed Apr. 29, 2014, 9 pages.
Advisory Action and Applicant-Initiated Interview Summary for U.S. Appl. No. 13/183,901 mailed Apr. 21, 2014, 5 pages.
Second Office Action for Chinese patent application 201210077192.7 mailed May 5, 2014, 3 pages.
Final Office Action for U.S. Appl. No. 11/434,033 mailed Jun. 2, 2014, 11 pages.
Non-final Office Action for U.S. Appl. No. 11/931,398 mailed Jun. 3, 2014, 8 pages.

(56) References Cited

OTHER PUBLICATIONS

Non-final Office Action for U.S. Appl. No. 11/928,681 mailed Jun. 4, 2014, 7 pages.
Non-final Office Action for U.S. Appl. No. 11/931,914 mailed Jun. 10, 2014, 15 pages.
First Office Action for Chinese patent application 201310017764.7 issued Mar. 31, 2014, 20 pages.
First Office Action for Chinese patent application 201310017761.3 issued May 6, 2014, 12 pages.
Second Office Action for Chinese patent application 201210077169.8 issued May 20, 2014, 3 pages (no translation).
Notice of Allowance for U.S. Appl. No. 11/434,033 mailed Aug. 8, 2014, 8 pages.
Final Office Action for U.S. Appl. No. 12/015,593 mailed Jul. 7, 2014, 19 pages.
Advisory Action for U.S. Appl. No. 12/015,600 mailed Jul. 16, 2014, 3 pages.
Examination Report for European Patent Application No. 07716441.6 mailed May 19, 2014, 4 pages.
Notice of Allowance for U.S. Appl. No. 11/928,681, mailed Sep. 22, 2014, 9 pages.
Advisory Action for U.S. Appl. No. 12/015,593, mailed Oct. 16, 2014, 3 pages.
Bron, Anthony J. et al., "Rethinking Dry Eye Disease: A Perspective on Clinical Implications," The Ocular Surface, vol. 12, No. 2S, Apr. 2014, Elsevier Inc., 31 pages.
Foulks, Gary N., "The Correlation Between the Tear Film Lipid Layer and Dry Eye Disease," Survey of Ophthalmology, vol. 52, Issue 4, Jul.-Aug. 2007, Elsevier Inc., pp. 369-374.
Lin, Hui et al., "Dry eye disease: A review of diagnostic approaches and treatments," Saudi Journal of Ophthalmology, vol. 28, Issue 3, Jul.-Sep. 2014, Saudi Ophthalmological Society, pp. 173-181.
Ozer, P.A. et al., "Eyelid nodule in a child: a chalazion or idiopathic facial aseptic granuloma?" Eye, vol. 28, No. 9, Sep. 2014, The Royal College of Ophthalmologists, pp. 1146-1147.
Non-Final Office Action for U.S. Appl No. 12/015,600 mailed Oct. 31, 2014, 9 pages.
Second Office Action for Chinese Patent Application No. 201310017764.7, issued Nov. 15, 2014, 12 pages.
Second Office Action for Chinese Patent Application No. 201210127347.3, issued Nov. 2, 2014, 7 pages.
Zhang, J. et al., "A Meibomian Gland Massage Mechanism for Upper and Lower Eyelids Based on Anti-phase Rolling and Enveloping Movement," Chinese Journal of Medical Instrumentation, vol. 38, No. 4, Jul. 2014, pp. 255-258, 273.
Notice of Allowance for U.S. Appl. No. 11/931,398, mailed Jan. 16, 2015, 8 pages.
Non-Final Office Action for U.S. Appl. No. 13/183,901, mailed Feb. 12, 2015, 9 pages.
Baumann, A. et al., "Meibomian gland dysfunction: A comparative study of modern treatments," French Journal of Ophthalmology, vol. 37, No. 4, Apr. 2014, Elsevier Masson SAS, pp. 303-312.
Notice of Rejection for Japanese Patent Application No. 2013-226709, mailed Mar. 24, 2015, 10 pages.
Final Office Action for U.S. Appl. No. 12/015,600 mailed May 21, 2015, 12 pages.
Non-Final Office Action for U.S. Appl. No. 11/931,914, mailed Jun. 8, 2015, 25 pages.
Non-Final Office Action for U.S. Appl. No. 12/015,593, mailed Jun. 4, 2015, 20 pages.
Third Office Action for Chinese Patent Application No. 201210127347.3, issued Jun. 26, 2015, 7 pages.
Examination Report for European Patent Application No. 06801969.4, mailed Jul. 6, 2015, 5 pages.
Notice of Allowance for U.S. Appl. No. 13/183,901, mailed Aug. 12, 2015, 11 pages.
Blackie, Caroline A., et al., "Treatment for meibomian gland dysfunction and dry eye symptoms with a single-dose vectored thermal pulsation: a review," Current Opinion in Ophthamology, vol. 26, Issue 4, Jul. 2015, Lippincott Williams & Wilkins, pp. 306-313.
Doan, S., et al., "Evaluation of an eyelid warming device (Blephasteam®) for the management of ocular surface diseases in France: The ESPOIR study," Journal Français d'Ophtalmologie, vol. 37, Issue 10, Dec. 2014, Elsevier Masson Sas, pp. 763-772.
Thode, Adam R., et al., "Current and Emerging Therapeutic Strategies for the Treatment of Meibomian Gland Dysfunction (MGD)," Drugs, vol. 75, Issue 11, Jul. 1, 2015, Springer International Publishing, pp. 1177-1185.
Vora, Gargi K., et al., "Intense pulsed light therapy for the treatment of evaporative dry eye disease," Current Opinion in Ophthalmology, vol. 26, Issue 4, Jul. 2015, Wolters Kluwer Health, Inc., pp. 314-318.
Advisory Action for U.S. Appl. No. 12/015,600 mailed Nov. 3, 2015, 3 pages.
Examination Report for European Patent Application No. 08727830.5 mailed Oct. 5, 2015, 5 pages.
Fourth Office Action for Chinese Patent Application No. 201210127347.3, issued Feb. 29, 2016, 9 pages.
Decision of Rejection for Japanese Patent Application No. 2013-226709, mailed Feb. 2, 2016, 8 pages.
Author Unknown, "Appendages of the eye," The Free Dictionary by Farlex, Medical Dictionary, retrieved on Feb. 8, 2016, medical-dictionary.thefreedictionary.com/appendages+of+the+eye, Farlex and Partners, 1 page.
Author Unknown, "Medical Definition of ORBIT," Merriam-Webster Dictionary, retrieved Feb. 8, 2016, www.merriam-webster.com/medical/orbit, Merriam-Webster, Incorporated, 2 pages.
Goslin, Krysta, et al., "Evaluation of a Single Thermal Pulsation Treatment for Dry Eye and Meibomian Gland Dysfunction and Likelihood of Positive SJO Test," Investigative Ophthalmology & Visual Science, vol. 56, Jun. 2015, The Association for Research in Vision and Ophthalmology, 2 pages (Meeting Abstract).
Hynes, Michael, et al., "Design of a subtarsal ultrasonic transducer for mild hyperthermia of meibomian glands treating Dry Eye Disease," Investigative Ophthalmology & Visual Science, vol. 56, Jun. 2015, The Association for Research in Vision and Ophthalmology, 3 pages (Meeting Abstract).
Nakayama, Naohiko, et al., "Analysis of Meibum Before and After Intraductal Meibomian Gland Probing in Eyes with Obstructive Meibomian Gland Dysfunction," Cornea, vol. 34, Issue 10, Oct. 2015, Wolters Kluwer Health, Inc., pp. 1206-1208.
Nakayama, Naohiko, et al., "Analysis of Meibum Before and Following Intraductal Meibomian Gland Probing for Eyes with Obstructive Meibomian Gland Dysfunction," Investigative Ophthalmology & Visual Science, vol. 56, Jun. 2015, The Association for Research in Vision and Ophthalmology, 2 pages (Meeting Abstract).
Ngo, William, et al., "Effect of Lid Debridement-Scaling on Dry Eye Signs and Symptoms in Sjogren's Syndrome," Investigative Ophthalmology & Visual Science, vol. 56, Jun. 2015, The Association for Research in Vision and Ophthalmology, 2 pages (Meeting Abstract).
Tanabe, Hirotaka, et al., "Effect of Eye Shampoo for Obstructive Meibomian Gland Disease," Investigative Ophthalmology & Visual Science, vol. 56, Jun. 2015, The Association for Research in Vision and Ophthalmology, 2 pages (Meeting Abstract).
Vegunta, Srav, et al., "Tear osmolarity measurements in ocular graft-versus-host disease patients undergoing intense pulsed light (IPL) and meibomian gland expression (MGX)," Investigative Ophthalmology & Visual Science, vol. 56, Jun. 2015, The Association for Research in Vision and Ophthalmology, 2 pages (Meeting Abstract).
Final Office Action for U.S. Appl. No. 12/015,593, mailed Feb. 16, 2016, 22 pages.
Non-Final Office Action for U.S. Appl. No. 14/510,843, mailed Feb. 4, 2016, 10 pages.
Notice of Allowance for U.S. Appl. No. 12/015,600, mailed Jan. 20, 2016, 7 pages.

(56) References Cited

OTHER PUBLICATIONS

Korb, Donald R. et al., "Restoration of Meibomian Gland Function Post Lipiflow® Treatment," ARVO Annual Meeting, May 2011, 3 pages (Abstract only).
Willis, Timothy et al., "Meibomian Gland Function, Lid Wiper Epitheliopathy, and Dry Eye Symptoms," ARVO Annual Meeting, May 2011, 3 pages (Abstract only).
Aragona, Pasquale et al., "Towards a dynamic customised therapy for ocular surface dysfunctions," British Journal of Ophthalmology, vol. 97, No. 8, Aug. 2013, pp. 955-960.
Dudee, Jitander S., "Affidavit," mailed Aug. 26, 2016, 2 pages.
U.S. Appl. No. 09/178,772, filed Oct. 26, 1998, not published.
Extended European Search Report for European Patent Application No. 16170742.7, mailed Sep. 8, 2016, 8 pages.
Author Unknown, "Simple Definition of Around," Merriam-Webster's Learner's Dictionary, accessed Aug. 15, 2016, www.merriam-webster.com/dictionary/around, 1 page.
Author Unknown, Definition of "Orbit," Miller-Keane Encyclopedia and Dictionary of Medicine, Nursing, and Allied Health, Seventh Edition, 2003, Saunders, medical-dictionary.thefreedictionary.com/orbit, accessed Sep. 29, 2016, 1 page.
Author Unknown, "Medical Definition of Periorbital," Merriam-Webster: Medical Dictionary, accessed Aug. 15, 2016, www.merriam-webster.com/medical/periorbital, 1 page.
Di Pascuale, Mario A., et al, "Lipid tear deficiency in persistent dry eye after laser in situ keratomileusis and treatment results of new eye-warming device," Journal of Cataract & Refractive Surgery, vol. 31, Issue 9, Sep. 2005, Elsevier, pp. 1741-1749.
Hynes, Michael, B., et al., "Design of a Subtarsal Ultrasonic Transducer for Mild Hyperthermia Treatment of Dry Eye Disease," Ultrasound in Medicine & Biology, vol. 42, Issue 1, Jan. 2016, Elsevier Inc., pp. 232-242.
Matsumoto, Yukihiro, et al., "Efficacy of a New Warm Moist Air Device on Tear Functions of Patients With Simple Meibomian Gland Dysfunction," Cornea, vol. 25, Issue 6, Jul. 2006, Lippincott Williams & Wilkins, pp. 544-650.
Non-Final Office Action for U.S. Appl. No. 11/541,308, mailed Sep. 29, 2016, 26 pages.
Non-Final Office Action for U.S. Appl. No. 14/618,392, mailed Sep. 30, 2016, 11 pages.
Final Office Action for U.S. Appl. No. 14/510,843, mailed Aug. 25, 2016, 13 pages.
Author Unknown, "Home," http://www.heatedeyepad.com/home.html, accessed Dec. 16, 2016, Digital Heat, 2 pages.
Author Unknown, "Product," http://www.heatedeyepad.com/product.html, accessed Dec. 16, 2016, Digital Heat, 2 pages.
Non-Final Office Action for U.S. Appl. No. 14/074,123, mailed Dec. 29, 2016, 23 pages.
First Examination Report for Indian Patent Application No. 1318/MUMNP/2009, issued Mar. 14, 2017, 20 pages.
Non-Final Office Action for U.S. Appl. No. 11/541,308, mailed Apr. 27, 2017, 21 pages.

\* cited by examiner

= SHOWS RF ENERGY & THERMAL GRADIENT

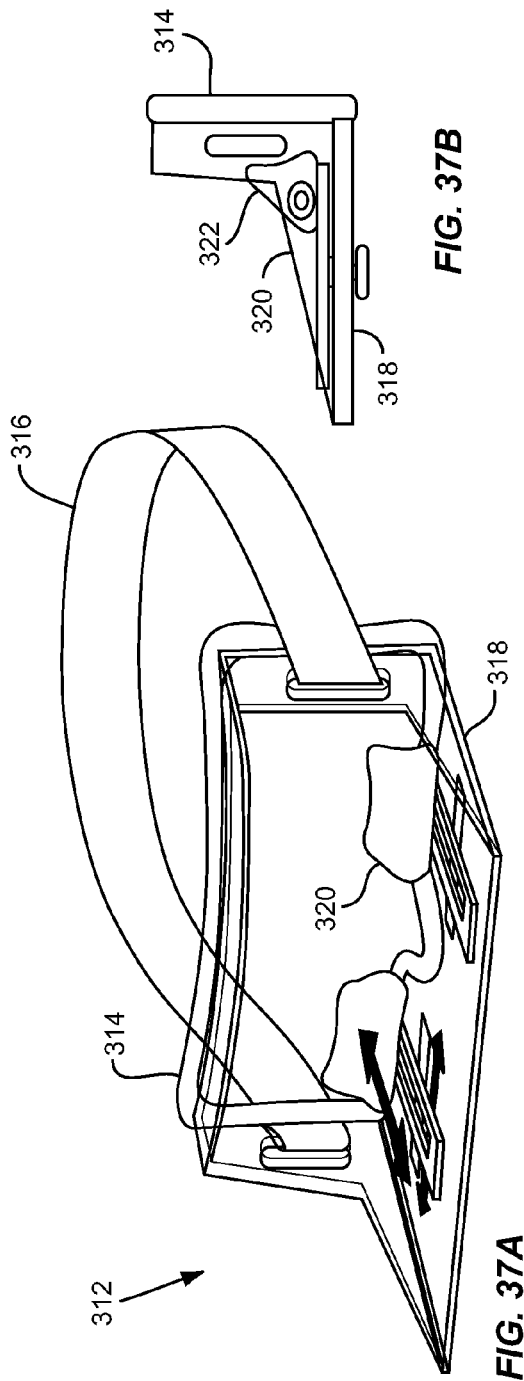
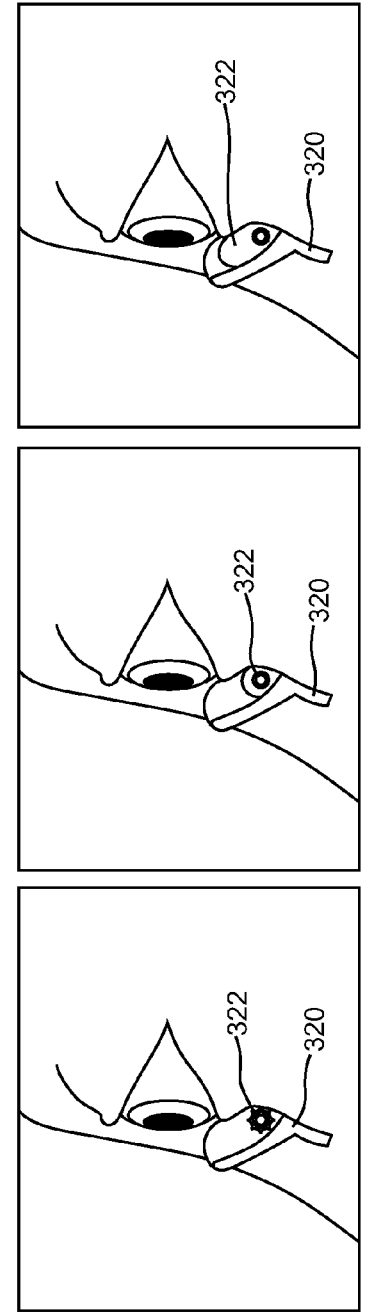
FIG. 37A
FIG. 37B
FIG. 37C
FIG. 37D
FIG. 37E

METHODS AND SYSTEMS FOR TREATING MEIBOMIAN GLAND DYSFUNCTION USING RADIO-FREQUENCY ENERGY

RELATED APPLICATIONS

The present application is a continuation of, and claims priority to, PCT Application No. PCT/US 12/44650 entitled "Methods and Systems for Treating Meibomian Gland Dysfunction Using Radio-Frequency Energy," filed Jun. 28, 2012, which in turn claims priority to U.S. Provisional Patent Application No. 61/502,120 entitled "Method and Systems for Treating Meibomian Gland Dysfunction Using Radio-Frequency Energy," filed Jun. 28, 2011, both of which are incorporated herein by reference in their entireties.

The present application is a continuation-in-part patent application of, and claims priority to, U.S. application Ser. No. 11/434,033, now U.S. Pat. No. 8,915,253, entitled "Method and Apparatus for Treating Gland Dysfunction Employing Heated Medium," filed on May 15, 2006, which claims priority to U.S. Provisional Patent Application No. 60/700,233, entitled "Method and Apparatus for Treating Gland Dysfunction," filed Jul. 18, 2005, both of which are incorporated herein by reference in their entireties.

The present application is also a continuation-in-part patent application of, and claims priority to, U.S. application Ser. No. 11/931,398, now U.S. Pat. No. 9,060,843, entitled "Method and Apparatus for Treating Gland Dysfunction Employing Heated Medium," filed on Oct. 31, 2007, which claims priority to U.S. application Ser. No. 11/434,033, now U.S. Pat. No. 8,915,253, entitled "Method and Apparatus for Treating Gland Dysfunction Employing Heated Medium," filed on May 15, 2006, which claims priority to U.S. Provisional Patent Application No. 60/700,233, entitled "Method and Apparatus for Treating Gland Dysfunction," filed Jul. 18, 2005, all of which are incorporated herein by reference in their entireties.

The present application is also a continuation-in-part patent application of, and claims priority to, U.S. application Ser. No. 13/242,068, now U.S. Pat. No. 8,685,073, entitled "Apparatus for Treating Meibomian Gland Dysfunction," filed on Sep. 23, 2011, which claims priority to U.S. application Ser. No. 12/821,183, now U.S. Pat. No. 8,025,689, entitled "Method and Apparatus for Treating Meibomian Gland Dysfunction," filed on Jun. 23, 2010, which claims priority to U.S. application Ser. No. 11/434,054, now U.S. Pat. No. 8,083,787, entitled "Method and Apparatus for Treating Meibomian Gland Dysfunction," filed on May 15, 2006, all of which are incorporated herein by reference in their entireties.

The present application is also a continuation-in-part patent application of, and claims priority to, U.S. application Ser. No. 13/183,901, now U.S. Pat. No. 9,216,028, entitled "Apparatuses for Treatment of Meibomian Glands," filed on Jul. 15, 2011, which claims priority to U.S. application Ser. No. 11/541,418, now U.S. Pat. No. 7,981,145, entitled "Treatment of Meibomian Glands," filed on Sep. 29, 2006, both of which are incorporated herein by reference in its entirety.

The present application is also a continuation-in-part patent application of, and claims priority to, U.S. application Ser. No. 11/541,308 entitled "Melting Meibomian Gland Obstructions," filed on Sep. 29, 2006, which is incorporated herein by reference in its entirety.

The present application is also a continuation-in-part patent application of, and claims priority to, U.S. application Ser. No. 11/893,669, now U.S. Pat. No. 8,255,039 entitled "Meibomian Gland Illuminating and Imaging," filed on Aug. 17, 2007, which is incorporated herein by reference in its entirety.

The present application is also a continuation-in-part patent application of, and claims priority to, U.S. application Ser. No. 12/015,593 entitled "Apparatus for Inner Eyelid Treatment of Meibomian Gland Dysfunction," filed on Jan. 17, 2008, which claims priority to U.S. Provisional Patent Application No. 60/880,850 entitled "Method and Apparatus for Treating Meibomian Gland Obstructive Disease," filed on Jan. 17, 2007, both of which are incorporated herein by reference in their entireties.

FIELD OF THE DISCLOSURE

The field of the disclosure relates to treatment of meibomian gland dysfunction (MGD), which may be either responsible for or be a contributing factor to a patient suffering from a "dry eye" condition. A patient's meibomian glands are treated to aid in facilitating a sufficient protective lipid layer being generated and retained on the tear film of the eye to retain aqueous.

BACKGROUND

In the human eye, the tear film covering the ocular surfaces is composed of three layers. The innermost layer in contact with the ocular surface is the mucus layer. The mucus layer is comprised of many mucins. The middle layer comprising the bulk of the tear film is the aqueous layer. The aqueous layer is important in that it provides a protective layer and lubrication to prevent dryness of the eye. Dryness of the eye can cause symptoms such as itchiness, burning, and irritation, which can result in discomfort. The outermost layer is comprised of many lipids known as "meibum" or "sebum." This outermost lipid layer is very thin, typically less than 250 nm in thickness. The lipid layer provides a protective coating over the aqueous and mucus layers to limit the rate at which these underlying layers evaporate. A higher rate of evaporation of the aqueous layer can cause dryness of the eye. Thus, if the lipid layer is not sufficient to limit the rate of evaporation of the aqueous layer, dryness of the eye may result. The lipid layer also lubricates the eyelid during blinking, which prevents dry eye. Dryness of the eye is a recognized ocular disease, which is generally known as "dry eye." If the lipid layer can be improved, the rate of evaporation is decreased, lubrication is improved, and partial or complete relief of the dry eye state is achieved.

The sebum that forms the outermost lipid layer is secreted by meibomian glands 10 of the eye, as illustrated in FIGS. 1 and 2 of this application. The meibomian glands are enlarged, specialized sebaceous-type glands (hence, the use of "sebum" to describe the secretion) located on both the upper eyelid 12 and lower eyelid 14. The meibomian glands contain orifices 16 that are designed to discharge lipid secretions onto the lid margins, thus forming the lipid layer of the tear film as the mammal blinks and spreads the lipid secretion. The typical human upper eyelid 12 has about twenty five (25) meibomian glands and the lower eyelid 14 has about twenty (20) meibomian glands, which are somewhat larger than those located in the upper lid. Blinking and the squeezing action of the muscle of Riolan surrounding the meibomian glands 10 are thought to be the primary mechanism to open the orifice for the release of secretion from the meibomian gland 10. The meibomian gland orifices 16 open on the lid margin usually along the mucocutaneous junction also known as the gray line. The meibomian gland orifices 16 are assumed to open with blinking and release minute amounts of sebum secretions onto the lid margin and then into the inferior tear meniscus. The lipid "sebum" in the tear meniscus is spread upward and over the tear film of the open eye by the upward blink action. Blinking causes the upper lid 12 to pull a sheet of the lipids secreted by the meibomian glands 10 over the other two layers of the tear film, thus forming a type of protective coating which limits the rate at which the underlying layers evaporate. If the lipid secretions are optimal, and adequate lipid layer is maintained at the air interface, evaporation is minimized and dry eye states are prevented. If the lipid secretions are inadequate, the lipid layer is not adequate to minimize evaporation with resulting rapid evaporation leading to dry eye states. Thus, a defective lipid layer or an insufficient quantity of such lipids can result in accelerated evaporation of the aqueous layer which, in turn, causes symptoms such as itchiness, burning, irritation, and dryness, which are collectively referred to as "dry eye."

Various treatment modalities have been developed to treat the dry eye condition. These modalities include drops, which are intended to replicate and replace the natural aqueous tear film and pharmaceuticals which are intended to stimulate the tear producing cells. For example, eye drops such as Refresh Endura™, Soothe™, and Systane™ brand eye drops are designed to closely replicate the naturally occurring healthy tear film. However, their use and administration are merely a treatment of symptoms and not of the underlying cause. Further, the use of aqueous drops is generally for an indefinite length of time and consequently, extended use can become burdensome and costly.

Pharmaceutical modalities, such as the use of tetracycline, have also been suggested to treat meibomian gland dysfunction. One such treatment is disclosed in U.S. Patent Application Publication No. 2003/0114426 entitled "Method for Treating Meibomian Gland Disease," U.S. Pat. No. 6,455,583 entitled "Method for Treating Meibomian Gland Disease" to Pflugfelder et al., and PCT Publication Application No. WO 99/58131 entitled "Use of Tetracyclines for Treating Meibomian Gland Disease." However, this treatment has not proven to be universally clinically effective, and it may be unnecessary in cases where MGD is the result of obstruction of the gland without infection.

The use of corticosteroids has also been proposed to treat MGD as disclosed in U.S. Pat. No. 6,153,607 entitled "Non-preserved Topical Corticosteroid for Treatment of Dry Eye, filamentary Keratitis, and Delayed Tear Clearance (or Turnover)" to Pflugfelder et al. Again, this proposed treatment appears to treat the symptoms of dry eye, as opposed to treatment of the underlying cause.

Additionally, the use of topically applied androgens or androgen analogues has also been used to treat acute dry eye signs and symptoms in keratoconjuctivitis sicca. This is disclosed in U.S. Pat. Nos. 5,958,912 and 6,107,289, both entitled "Ocular Therapy in Keratoconjunctivitis Sicca Using Topically Applied Androgens or TGF-beta." and both issued to Sullivan.

There is a correlation between the tear film lipid layer and dry eye disease. The various different medical conditions and damage to the eye and the relationship of the lipid layer to those conditions are reviewed in Surv Opthalmol 52:369-374, 2007. It is clear that the lipid layer condition has the greatest effect on dry eye disease when compared to the aqueous layer or other causes. Thus, while dry eye states have many etiologies, the inability of the meibomian gland 10 to sufficiently generate the lipid layer is a common cause of common dry eye state. This state is the condition known as "meibomian gland dysfunction" (MGD). MGD is a disorder where the meibomian glands 10 are obstructed or occluded. As employed herein the terms "occluded" and "obstruction" as they relate to meibomian gland dysfunction are defined as partially or completely blocked or plugged meibomian glands. If completely obstructed the gland cannot secrete. If partially or intermittently occluded the gland may secrete either normal or decreased amounts of sebum. More usually the secretions are altered having semi-solid, thickened, congested secretions, frequently described as inspissated. The secretions may be clear or yellowish, the latter indicating possible infection. Meibomitis, an inflammation of the meibomian glands leading to their dysfunction, is usually accompanied by blepharitis (inflammation of the lids). Meibomian gland dysfunction may accompany meibomitis, or meibomian gland dysfunction may be present without obvious lid inflammation.

MGD is frequently the result of keratotic obstructions, which partially or completely block the meibomian gland orifices 16. Such obstructions compromise the secretory functions of the individual meibomian glands 10. More particularly, these keratotic obstructions may be associated with or result in various combinations of bacteria, sebaceous ground substance, dead, and/or desquamated epithelial cells (see, Meibomian Gland Dysfunction and Contact Lens Intolerance, Journal of the Optometric Association, Vol. 51, No. 3, Korb et al., (1980), pp. 243-51).

Hormonal changes, which occur during menopause and particularly changing estrogen levels, can result in thickening of the oils secreted by the meibomian glands 10. This may result in clogged gland orifices. Further, decreased estrogen levels may also enhance conditions under which staphylococcal bacteria can proliferate. This can cause migration of the bacteria into the glands 10 compromising glandular function and further contributing to occlusion, thus resulting in a decreased secretion rate of the meibomian gland 10.

When the flow of secretions from the meibomian gland 10 is restricted due to the existence of an occlusion, cells on the eyelid margin have been observed to grow over the gland orifice 16. This may further restrict sebum flow and exacerbate a dry eye condition. Additional factors may also cause or exacerbate meibomian gland dysfunction including age, disorders of blinking, activities such as computer use which compromise normal blinking, contact lens use, contact lens hygiene, cosmetic use, or other illness, particularly diabetes. The state of an individual meibomian gland 10 can vary from optimal, where clear meibomian fluid is produced; to mild or moderate meibomian gland dysfunction where milky fluid or inspis sated or creamy secretion is produced; to total blockage, where no secretion of any sort can be obtained (see "Increase in Tear Film Lipid Layer Thickness Following Treatment of Meibomian Gland Dysfunction," Lacrimal Gland, Tear Film, and Dry Eye Syndromes," Korb, et al., pp. 293-98, Edited by D. A. Sullivan, Plenum Press, New York (1994)). Significant chemical changes of the meibomian gland 10 secretions occur with meibomian gland dysfunction and consequently, the composition of the naturally occurring tear film is altered, which in turn, contributes to dry eye.

MGD may be difficult to diagnose, because visible indicators are not always present. For example, meibomitis, an inflammation of the meibomian glands 10, can lead to MGD. Meibomitis may also be accompanied by blepharitis (inflammation of the lids). While meibomitis is obvious by inspection of the external lids, MGD may not be obvious even when examined with the magnification of the slit-lamp biomicroscope. This is because there may not be external signs or the external signs may be so minimal that they are overlooked. The external signs of MGD without obvious lid inflammation may be limited to subtle alterations of the meibomian gland orifices 16, overgrowth of epithelium over the orifices 16, and pouting of the orifices 16 of the glands 10 with congealed material acting as obstructions. In severe instances of MGD without obvious lid inflammation, the changes may be obvious, including serrated or undulated lid margins, orifice recession and more obvious overgrowth of epithelium over the orifices 16, and pouting of the orifices 16.

Thus to summarize, the meibomian glands 10 of mammalian (e.g., human) eyelids secrete oils that prevent evaporation of the tear film and provide lubrication to the eye and eyelids. These glands can become blocked or plugged (occluded) by various mechanisms leading to so-called "dry eye syndrome." While not the only cause, MGD is a known cause of dry eye syndrome. The disorder is characterized by a blockage of some sort at an orifice of the meibomian glands 10 preventing normal lipid secretions from flowing from the meibomian glands 10 to form the lipid layer of the tear film. Such secretions serve to prevent evaporation of the aqueous tear film and lubricate the eye and eyelids 12, 14, hence, their absence can cause dry eye syndrome.

While the present state of the art provides a number of treatments for dry eye, there is a need to treat the underlying cause, as opposed to the symptom. Many patients suffer from dry eye as a result of obstructions or occlusions in the meibomian glands. Thus, a need exists to provide effective treatment of the meibomian glands to restore a sufficient flow of sebum to the lipid layer of the eye to limit the rate of evaporation of the underlying layers.

SUMMARY OF THE DETAILED DESCRIPTION

It is herein recognized that, in addition to obstructions at an orifice of a meibomian gland, obstructions located within a meibomian gland channel (duct) below the orifice, can also be a cause of lipid layer deficiency in a tear film that could lead to evaporative dry eye MGD. It is further recognized that obstructions within the meibomian gland channel causing lipid layer deficiency may not be obvious to detect, because MGD may be present without obvious lid inflammation, as opposed to clogged meibomian gland orifices, where meibomitis is present and obvious by inspection of the external eyelids. Thus, regardless of whether a clogged meibomian gland orifice is recognized by the presence of meibomitis and unclogged as part of a treatment to remove bacterial flora that reside at the eyelid margin, if an obstruction is located within the meibomian gland channel (duct), the obstruction may not be detected. As a result, secretions from the meibomian gland may still not flow in order to be added to the tear film upon blinking, regardless of whether a meibomian gland orifice is unclogged. Thus, the inventors of the present application recognized that removing obstructions from within a channel or duct of the meibomian gland would be beneficial for treating MGD.

In this regard, embodiments disclosed herein include methods and systems for treating meibomian gland dysfunction. In one embodiment, a method is provided and comprises directing RF energy to an internal portion of a meibomian gland, selectively targeting an obstruction within a duct of the meibomian gland with the applied RF energy to melt, loosen, or soften the obstruction, and expressing the obstruction from the duct of the meibomian gland. Embodiments disclosed herein can use RF or microwave energy to soften obstructions in the internal portions of the meibomian glands to treat meibomian gland dysfunction (MGD). Using RF or microwave energy may allow an efficient heat transfer to the meibomian gland duct to be attained, which may allow higher temperatures to be attained at the meibomian glands and/or in a more efficient time to melt, loosen, or soften more serious obstructions or occlusions in the meibomian glands. RF energy may allow heightened temperatures at the meibomian glands to be attained and in less time when applying heat to the outside of the eyelid due to more effective conductive heat transfer and the proximity of the heating to the eyelid surface.

In another embodiment, an apparatus for treating meibomian gland dysfunction is disclosed. The apparatus comprises at least one RF electrode configured to direct RF energy to an internal portion of a meibomian gland located in an eyelid of an eye, the at least one RF electrode further configured to selectively target an obstruction within a duct of the meibomian gland with the applied RF energy to melt, loosen, or soften the obstruction. The apparatus also comprises at least one mechanical expressor configured to express the obstruction from the duct of the meibomian gland.

In another embodiment, a method of treating meibomian gland dysfunction is disclosed. The method comprising positioning an RF electrode proximate an external surface of an eyelid containing at least one meibomian gland, directing RF energy via the RF electrode to an internal portion of a meibomian gland, selectively targeting an obstruction within a duct of the meibomian gland with the applied RF energy to melt, loosen, or soften the obstruction; and expressing the obstruction from the duct of the meibomian gland.

The methods may be performed by apparatuses according to embodiments disclosed herein. In one example, such an apparatus may comprise an RF electrode configured to be positioned proximate an external surface of an eyelid containing at least one meibomian gland. The apparatus may also comprises an energy delivery source configured to direct RF energy via the RF electrode to an internal portion of a meibomian gland to selectively target an obstruction within a duct of the meibomian gland with the applied RF energy to melt, loosen, or soften the obstruction. At least one mechanical expressor configured to express the obstruction from the duct of the meibomian gland is also included in the apparatus.

In another embodiment, a method of treating meibomian gland dysfunction is disclosed. The method comprising positioning an RF electrode proximate an internal surface of an eyelid containing at least one meibomian gland, directing RF energy via the RF electrode to an internal portion of a meibomian gland, selectively targeting an obstruction within a duct of the meibomian gland with the applied RF energy to melt, loosen, or soften the obstruction; and expressing the obstruction from the duct of the meibomian gland.

The above method may be performed by an apparatus according to one embodiment. The apparatus comprises an RF electrode configured to be positioned proximate an internal surface of an eyelid containing at least one meibomian gland. The apparatus also comprises an energy delivery source configured to direct RF energy via the RF electrode to an internal portion of a meibomian gland to selectively target an obstruction within a duct of the meibomian gland with the applied RF energy to melt, loosen, or soften the obstruction. At least one mechanical expressor configured to express the obstruction from the duct of the meibomian gland is also included in the apparatus.

In another embodiment, a method of treating meibomian gland dysfunction is disclosed that uses a plurality of RF electrodes. The method comprises positioning a first RF electrode proximate an inner surface of an eyelid containing at least one meibomian gland and positioning a second RF electrode proximate an external surface of the eyelid. RF energy is then applied via at least one of the first RF electrode and the second RF electrode to an internal portion of a meibomian gland. An obstruction within a duct of the meibomian gland is selectively targeted with the applied RF energy to melt, loosen, or soften the obstruction, and the softened obstruction is then expressed from the duct of the meibomian gland.

The method described above may be performed using an apparatus according to another embodiment. The apparatus comprises a first RF electrode configured to be positioned proximate an inner surface of an eyelid containing at least one meibomian gland and a second RF electrode configured to be positioned proximate an external surface of the eyelid. The apparatus further includes an energy delivery source configured to direct RF energy via at least one of the first RF electrode and second RF electrode to an internal portion of a meibomian gland to selectively target an obstruction within a duct of the meibomian gland with the applied RF energy to melt, loosen, or soften the obstruction. At least one expressor configured to express the obstruction from the duct of the meibomian gland is also included.

In another embodiment, a method of treating meibomian gland dysfunction is disclosed. The method includes applying a topical agent to an eyelid having at least one meibomian gland. An eyecup is then positioned on a globe of an eye and the eyelid is placed on a positioning pad. An energy delivery device is positioned proximate the positioning pad and energy is applied to the eyelid via the energy delivery device to soften an obstruction in the meibomian gland. The softened obstruction is then aspirated from the meibomian gland.

In another embodiment, after expression of the occlusions or obstructions is performed, an optional pharmacological agent may be applied to the meibomian gland to promote the free flow of sebum and/or reduce or prevent inflammation or infections of the eye or eyelids. Many pharmacological agents have been proposed for treatment of dry eye syndrome, any of which may be effective or more effective upon clearing of obstructions within the meibomian glands. Some of the pharmacological agents that may be utilized include, but are not limited to: antibiotics such as topical or oral tetracycline and chemically modified tetracycline, testosterone, topical or oral corticosteroids, topical androgens or androgen analogues, omega 3 fatty acid compounds such as fish oils, Laennec, enzymes that promote lipid production, agents that stimulate production of enzymes that promote lipid production, and/or any agent which acts as a secretagogue to enhance meibomian gland secretion or secretion of other tear components. For example, androgen and androgen analogues and TGF-beta have been reported to act as a secretagogue to enhance meibomian gland secretion.

These compounds are illustrative examples of appropriate pharmacological agents, but those skilled in the art will appreciate that other pharmacological compounds may be utilized.

Also, agents, such as Restasis (cyclosporine A), that replace or promote production of the tear component may also be applied more effectively after treating the meibomian glands according to one or more of the embodiments disclosed herein. Treating the meibomian glands improves the lipid layer thus reducing evaporation and conserving the aqueous layer. Conservation of the aqueous layer reduces the need for tear substitutes to be applied through tear component agents. Thus, tear component agents may not have to be used as often when employing the embodiments disclosed herein to treat a patient's MGD.

In addition, convective heat losses occur due to blood flow in the blood vessels located inside the eyelid. Blood flow through blood vessels located inside the eyelid produces convective heat losses. The blood flow serves as a natural "heat sink" provided by the body. Convective heat loss is lessened when directing RF energy to the internal portions of the meibomian gland within the eyelid than when applying heat to the outside of the eyelid. This is because fewer blood vessels are located between the meibomian glands and the inside of the eyelid than the outside of the eyelid. The meibomian glands are located closer to the inside of the eyelid. Moreover, it was discovered that if the blood flow was reduced, convective heat losses could be minimized allowing for temperatures to be attained and sustained at the meibomian glands in an even more efficient manner and in less time.

Thus, one embodiment also includes the further application of force to the patient's eyelid in addition to RF energy. The application of force can further assist in obtaining higher temperatures more efficiently inside the eyelid at the palpebral conjunctiva and at the meibomian gland in a shorter period of time and thus more efficiently. This is because the application of force may reduce blood flow to the eyelid to reduce convective heat loss, as discussed above.

Applying force can also result in a more efficient conductive heat transfer from an applied RF energy source, because the pressure created by the force causes the RF energy source to be compressed against the tissue of the eyelid. This compression can have several benefits. Compression spreads out the tissue to which heating is applied thus making it thinner and improving conductive heat transfer. Compression can also "squeeze out" air pockets at the surface of the eyelid due to the microscopic roughness of skin. Thus, compression of the RF energy source against the eyelid increases the surface contact between the RF energy source and the surface of the eyelid (which increases the heat transfer equation) to provide a more effective conductive heat transfer to the meibomian glands. This results in the meibomian glands being heated to the desired temperature level in a shorter period of time due to these gained efficiencies. Further, increased temperatures may be attained that may not have otherwise been obtained, or obtained using less heat or thermal energy. Because the heating is located in close proximity to the eyelid surface and the RF energy source is further compressed against the eyelid surface, heat transfer is very efficient providing for the temperature at the surface of the eyelid to be very close to the temperature at the meiboimian glands.

The applied force may be regulated, meaning that a force generating means is controlled to be within pressure ranges that are safe to be applied to the eyelid and at sufficient pressure to allow the temperature at the meibomian gland to be raised sufficiently. The force can also be a constant force and be provided manually.

The force may be applied during, after, or both during and after the application of the RF energy. In either case, the force may assist in expressing occlusions or obstructions when in a loosened, softened, or melted state from the meibomian glands. The force may include vibratory type forces, including those generated mechanically or those using fluid type devices or mechanisms. The level of force needed to express obstructions or occlusions in the glands may be greatly reduced when RF energy is applied to the obstructions or occlusions to place them in a melted, softened, or loosened state.

The application of force can also stimulate the movement of fluids or suspensions of occlusions or obstructions from the glands. Devices, which generally apply a regulated force or milking action to the eyelid to express the fluids or suspensions or to otherwise mechanically stimulate the movement of fluids from the glands, may be used. In some instances, a small, gentle, continuous force applied to the eyelid will assist in expression of the fluids and suspensions. Vibration can also be used when applying force simultaneously or immediately after the heating to further assist in the expression.

Those skilled in the art will appreciate the scope of the present invention and realize additional aspects thereof after reading the following detailed description of the preferred embodiments in association with the accompanying drawing figures.

BRIEF DESCRIPTION OF THE DRAWINGS

The accompanying drawing figures incorporated in and forming a part of this specification illustrate several aspects of the disclosed embodiments, and together with the description serve to explain the principles of the disclosed embodiments.

FIG. 7B is a broken away side view of the probe tip of FIG. 5a;

FIG. 8B is a side view of an exemplary embodiment of a probe tip having rollers for clearing obstructed meibomian glands on;

FIG. 37A is a perspective view of another embodiment of the meibomian gland treatment apparatus in the form of the hydro-oculator;

FIG. 37B is a side view of the hydro-oculator of FIG. 37A;

FIG. 37C is a schematic side view of the hydro-oculator of FIG. 37A in place against the lower eyelid;

FIG. 37D is a schematic side view of the hydro-oculator of FIG. 37A in place against the lower eyelid and showing the fluid filled bladder beginning to expand.

FIG. 37E is a schematic side view of the hydro-oculator of FIG. 37A in place against the lower eyelid and showing the fluid filled bladder in a further expanded state.

DETAILED DESCRIPTION

Figure 2:
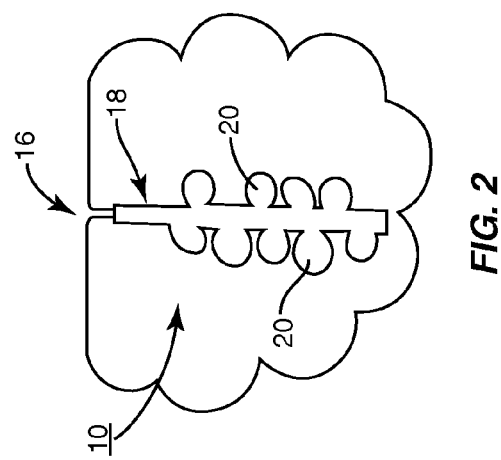
FIG. 2 illustrates an exemplary cutaway view of a meibomian gland.

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

It is herein recognized that, in addition to obstructions at an orifice of a meibomian gland, obstructions located within a meibomian gland channel (duct) below the orifice, can also be a cause of lipid layer deficiency in a tear film that could lead to evaporative dry eye MGD. It is further recognized that obstructions within the meibomian gland channel causing lipid layer deficiency may not be obvious to detect, because MGD may be present without obvious lid inflammation, as opposed to clogged meibomian gland orifices, where meibomitis is present and obvious by inspection of the external eyelids. Thus, regardless of whether a clogged meibomian gland orifice is recognized by the presence of meibomitis and unclogged as part of a treatment to remove bacterial flora that reside at the eyelid margin, if an obstruction is located within the meibomian gland channel (duct), the obstruction may not be detected. As a result, secretions from the meibomian gland may still not flow in order to be added to the tear film upon blinking, regardless of whether a meibomian gland orifice is unclogged. Thus, the inventors of the present application recognized that removing obstructions from within a channel or duct of the meibomian gland would be beneficial for treating MGD.

In this regard, embodiments disclosed herein include methods and systems for treating meibomian gland dysfunction. In one embodiment, a method is provided and comprises directing RF energy to an internal portion of a meibomian gland, selectively targeting an obstruction within a duct of the meibomian gland with the applied RF energy to melt, loosen, or soften the obstruction, and expressing the obstruction from the duct of the meibomian gland. Embodiments disclosed herein can use RF or microwave energy to soften obstructions in the internal portions of the meibomian glands to treat meibomian gland dysfunction (MGD). Using RF or microwave energy may allow an efficient heat transfer to the meibomian gland duct to be attained, which may allow higher temperatures to be attained at the meibomian glands and/or in a more efficient time to melt, loosen, or soften more serious obstructions or occlusions in the meibomian glands. RF energy may allow heightened temperatures at the meibomian glands to be attained and in less time when applying heat to the outside of the eyelid due to more effective conductive heat transfer and the proximity of the heating to the eyelid surface.

Some patients have obstructions or occlusions in their meibomian glands that will not sufficiently melt, loosen, or soften to be expressed without attaining heightened temperatures at the meibomian glands. In many instances, these temperatures either cannot be achieved when applying conductive heat to the outside of the eyelid, or these temperatures may be achievable, but only after applying heat to the outside of the eyelid for a significant period of time. Heightened temperatures may also only be achieved by applying heat at unsafe temperatures that would either produce an unacceptable pain response to the patient or damage to the patient's eyelid. This is because of the temperature drop between the outside of the eyelid and the meibomian glands due to conductive heat loss. Heat applied to the outside of the eyelid must conductively travel through the eyelid tissue and through the tarsal plate that encases the meibomian glands inside the eyelid. As an example, it may take twenty to thirty minutes for the temperature at the meibomian glands to reach only a temperature of 41 to 42 degrees Celsius when applying heat to the outside of the eyelid that will not burn or damage the patient's eyelid or surrounding tissue. Temperatures may need to reach between 43 to 45 degrees Celsius, for example, for melting, loosening, or softening of certain obstructions or occlusions in a patient's meibomian glands.

The ability to effectively and more efficiently raise the temperature at the meibomian glands by directing RF energy may prove instrumental in reaching the melting, loosening, or softening points of obstructions or occlusions. Directing RF energy can also include directing RF energy to the meibomian glands orifices that are located at the inner surface of the eyelid at the lid margin. The orifices may also be obstructed or occluded. The application of RF energy to the internal portions of the meibomian glands and proximate or directly to the meibomian glands orifices may also prove instrumental in restoring sufficient sebum flow for the lipid layer.

The regulated RF energy can be maintained at a therapeutic temperature for a treatment period. The treatment period can be approximately 1 to 10 minutes for example. The RF energy could also be repeatedly applied and maintained for a desired period of time to keep the occlusion or obstruction in a melted, loosened, or softened state. Either during or after such treatment by regulated RF energy, mechanical expression of lipids and other fluids from the meibomian glands has been found to clear obstructions which have essentially melted or been placed in a suspension state (by virtue of melting materials binding solids together).

As discussed above, in the human eye, the tear film covering the ocular surfaces is composed of three layers. The innermost layer in contact with the ocular surface is the mucus layer. The mucus layer is comprised of many mucins. The middle layer comprising the bulk of the tear film is the aqueous layer. The aqueous layer is important in that it provides a protective layer and lubrication to prevent dryness of the eye. Dryness of the eye can cause symptoms such as itchiness, burning, and irritation, which can result in discomfort. The outermost layer is comprised of many lipids known as "meibum" or "sebum." This outermost lipid layer is very thin, typically less than 250 nm in thickness. The lipid layer provides a protective coating over the aqueous and mucus layers to limit the rate at which these underlying layers evaporate. A higher rate of evaporation of the aqueous layer can cause dryness of the eye. Thus, if the lipid layer is not sufficient to limit the rate of evaporation of the aqueous layer, dryness of the eye may result. The lipid layer also lubricates the eyelid during blinking, which prevents dry eye. Dryness of the eye is a recognized ocular disease, which is generally known as "dry eye." If the lipid layer can be improved, the rate of evaporation is decreased, lubrication is improved, and partial or complete relief of the dry eye state is achieved.

Figure 1:
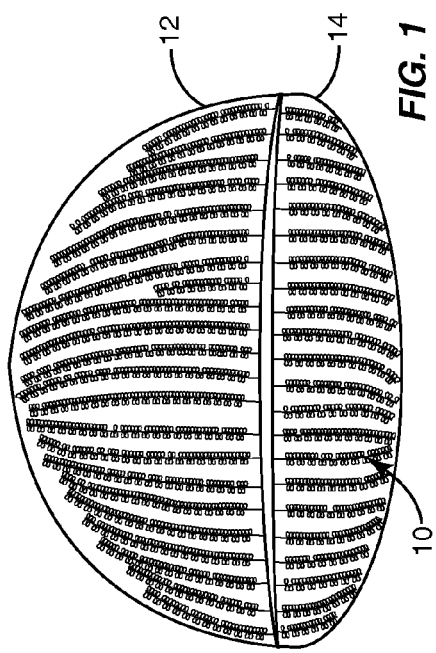
FIG. 1 illustrates an exemplary upper and lower human eyelid showing the meibomian glands.

With respect to FIGS. 1 and 2, the sebum that forms the outermost lipid layer is secreted by meibomian glands 10 of the eye, as illustrated in FIGS. 1 and 2 of this application. The meibomian glands are enlarged, specialized sebaceous-type glands (hence, the use of "sebum" to describe the secretion) located on both the upper eyelid 12 and lower eyelid 14. The meibomian glands contain orifices 16 that are designed to discharge lipid secretions onto the lid margins, thus forming the lipid layer of the tear film as the mammal blinks and spreads the lipid secretion. The typical human upper eyelid 12 has about twenty five (25) meibomian glands and the lower eyelid 14 has about twenty (20) meibomian glands, which are somewhat larger than those located in the upper lid. It is known that obstructions or blockages at the orifices 16 can lead to poor lipid secretion, which may result in dry eye.

Figure 3:
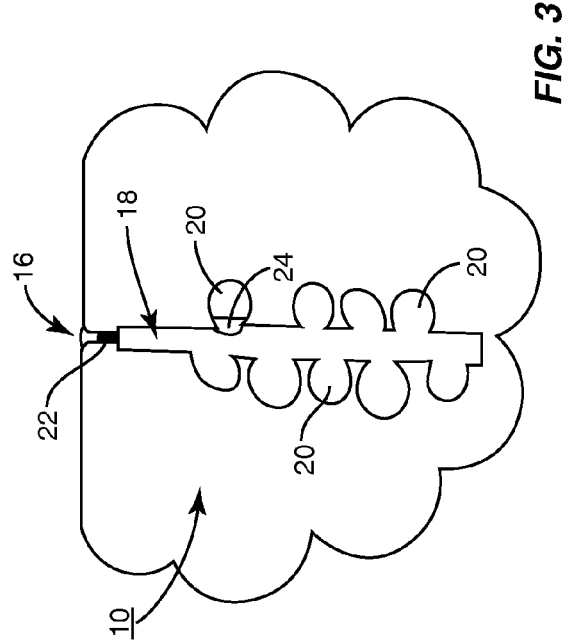
FIG. 3 illustrates an exemplary cutaway view of a meibomian gland having a plurality of clogging mechanisms.

The inventors of the present application recognized for the first time that blockages within other parts of the meibomian glands 10 below the orifice 16 could also prevent an adequate lipid secretion and cause dry eye. Referring to FIG. 3, each meibomian gland 10 has a straight long central duct 18 lined with four epithelial layers on the inner surface of the duct 18. Along the length of the central duct 18 are multiple lateral out-pouching structures 20, termed acini, where the secretion of the gland is manufactured. The inner lining of each acinus 20 differs from the main central duct 18 in that these specialized cells provide the secretions of the meibomian gland. The secretions flow from each acinus 20 to the duct 18. While it has not been established with certainty, there appears to be a valve system between each acinus 20 and the central duct 18 to retain the secretion until it is required, at which time it is discharged into the central duct 18. The meibomian secretion is then stored in the central duct 18 and is released through the orifice of each gland onto the lid margin. The inventors recognized that if these valves exist, they may also become obstructed in some instances leading to reduced or blocked flow from the acini 20. These obstructions or occlusions 22, 24 may have various compositions.

FIG. 3 illustrates an example of obstructions 22, 24 or occlusions 22, 24. Plug obstructions 22 can occur at the orifice 16 located at a top of the meibomian gland 10. Alternatively, obstructions and occlusions 24 can occur in the central duct 18 and may also block a particular acinus 20, as seen in FIG. 3. The obstructions or occlusions 22, 24 can mean that the meibomian glands 10 are partially blocked or plugged, completely blocked or plugged, or any variation thereof. Obstructions and occlusions 22, 24 can be in a solid, semi-solid, or thickened, congealed secretion and/or a plug, leading to a compromise, or more specifically, a decrease in or cessation of secretion. Also, with a reduced or limited secretion, the meibomian gland 10 may be compromised by the occluded or obstructive condition often evidenced by a yellowish color, indicating a possible infection state. Alternatively, the meibomian gland 10 may be otherwise compromised so that the resulting protective lipid film is not adequate for preventing evaporation of the underlying layers on the eye.

MGD is frequently the result of keratotic obstructions, which partially or completely block the meibomian gland orifices 16 and/or the central duct (canal) 18 of the gland 10, or possibly the acini or acini valves (assuming they do in fact exist) or the acini's junction 20 with the central duct 18. Such obstructions 22, 24 compromise the secretory functions of the individual meibomian glands 10. More particularly, these keratotic obstructions may be associated with or result in various combinations of bacteria, sebaceous ground substance, dead, and/or desquamated epithelial cells (see, Meibomian Gland Dysfunction and Contact Lens Intolerance, Journal of the Optometric Association, Vol. 51, No. 3, Korb et al., (1980), pp. 243-51).

Referring again to FIG. 3, obstructions or occlusions 22, 24 of the meibomian glands 10 may be present over or at the orifice 16 of the gland 10, in the main channel 18 of the gland 10, which may be narrowed or blocked, or possibly in other locations including the passages from the acini 20 to the main channel 18. Methods and apparatuses disclosed herein are designed to treat MGD that is caused by obstructions due to infection and inflammation at the orifice of the meibomian, as well as a different type of MGD caused by obstructions within the central duct or channel 18 of the meibomian gland 10, or within the acini 20, or at the junction of the acini 20 and the central duct or channel 18.

This includes loosening or removing possible obstructions or occlusions 22, 24 in the meibomian glands 10, including the expression of obstructions located within the central duct 18 or the acinus 20 of the meibomian gland 10 through an orifice 16 of the meibomian gland 10. FIG. 2 of the application shows the obstructions or occlusions 22, 24 of FIG. 3 in the meibomian glands 10 removed to restore sebum flow to the lipid layer.

Microwave and RF energy may be utilized to pinpoint thermal energy at specific target tissues. In addition, RF and microwave energy can be manipulated to be absorbed or directed for a certain type of cellular content or tissue material make up. For instance, the RF or microwave energy waveforms can be directed to be absorbed preferentially by energy absorbing cellular fluids, saline or lipid containing materials found in the ducts, channels, or acini of the meibomian glands rather than the cellular structures of the meibomian glands themselves. Pulsed waveform energy may react more preferentially on certain cellular fluids and contents than continuous waveforms. Specifically for the removal of meibomian gland obstructions, the desired temperature range for liquefying lipid containing obstructions is quickly and easily achievable using RF energy. Thus, in the area of removing meibomian gland obstructions, a series of short pulsed RF energy waves or microwaves could preferentially heat gland contents within the eyelid without raising the temperature of surrounding tissues or unintended tissue surfaces significantly.

Besides selectively heating different types of tissue contents and not heating indiscriminately surrounding tissue, microwave/RF energy can be directed to perform at a predetermined depth as seen in hyperthermia treatments or when treating a specific depth within the wall of the arterial vessel. For meibomian gland obstructions, being able to treat within the duct itself will have advantages by avoiding thermal injury to eyelid tissue surfaces, which are in close proximity to the ducts, and the eye, cornea, and other unintended structures that are clearly thermally sensitive tissues.

Another important benefit with the described systems is that RF or microwave energy can provide a very rapid direct internal heating source. The clear advantage with this would be an overall decrease in procedural time and reducing patient discomfort from the procedure. In addition since the thermal energy does not require conductive heating or a thermal gradient through tissue to reach its intended target, theoretically terminating the procedure could occur more quickly. Finally, for busy physician practices, shorter procedural times will improve patient flow through the practice.

In the current application, the desired amount of thermal energy to deliver to contents within the meibomian glands is 45 degrees C. Microwave or RF energy can be controlled by the ESU to selectively heat to a known temperature within the tissues and/or selectively heat lipid containing materials by adjusting the power and duration of the RF or microwave energy; adjusting the shape of the waveform (stepped or curved); using pulsed or continuous waveforms; adjusting the shape of antenna or electrode that delivers or emits the RF or microwave energy.

As briefly mentioned herein above, obstruction composition will vary with the etiology which produced it. However, the obstruction will, in most cases, consist of a combination of, dead cells, keratin, bacteria, desquamated cells, sebaceous ground substance, milky fluid, inspissated or creamy secretions, or any combination of the foregoing in solid, semi-solid and thickened forms. The obstruction may be in the gland channel, at the gland orifice, atop the gland orifice or a combination of the foregoing. As employed herein, obstruction refers to any of the foregoing.

Thus, it is self-evident that any obstruction of the channel will restrict or prevent secretions from exiting the gland and further, that in order to clear such obstructions or "occlusions", the obstruction may be loosened from the gland wall, and/or broken up, fractured, softened, or liquified so that it will fit through the gland orifice without causing excessive pain. Lastly, the obstruction remnants must be expressed from the gland. The embodiments disclosed herein provide a method and apparatus to accomplish these tasks.

According to one embodiment, the obstructions 22, 24 as seen in FIG. 3 should be softened or liquefied prior to attempting extraction or expression. With respect to the foregoing, the terms "softened" or "liquified" are intended to mean a "non-solid" flowable state. In addition, in order to be clinically satisfactory, softening or liquefying of the obstructions 22 or 24 should be effected as quickly as possible and regulated heat treatment time should be less than five (5) minutes with one to two (1-2) minutes being preferred without causing damage to the surrounding tissues of the ocular globe or the eye. The heating of the obstructions 22 or 24 may be accomplished by any number of techniques. Many of the embodiments disclosed herein will be discussed with RF energy being used for the heating. However, the heat treatments can also be electrical, laser heating, hot water conductive heating, infrared heating, ultrasonic heating, etc., in lieu of or in addition to RF heating. The disclosed heating treatments necessarily require the addition of a greater amount of energy (heating) than is deliverable by the conventional application of hot compresses which according to current practice are applied for 3-15 minutes prior to the clinician attempting to remove the obstruction. Once the obstruction is softened or liquefied, removal is obtained by the application of a regulated force to the gland. More specifically, it is contemplated by embodiments disclosed herein that the force applied be a repeatable controlled force, as more fully explained herein below.

Figure 4:
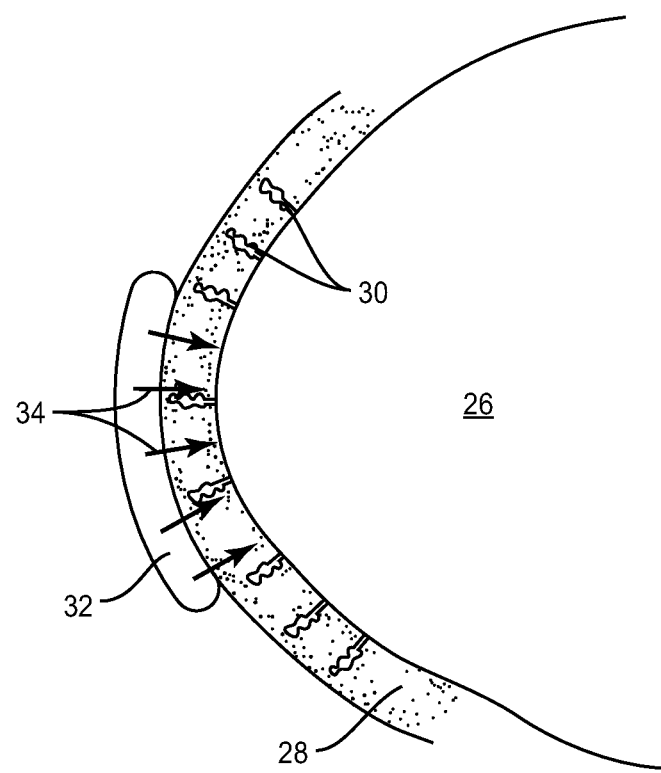
FIG. 4 illustrates an RF electrode for directing RF energy to meibomian glands in an eyelid.

In order to soften, melt, or loosen obstructions in the meibomian glands, as discussed above, in one embodiment, thermal energy may be applied to the obstruction 22 or 24 without contacting the meibomian gland. In one embodiment, RF energy may be applied to the meibomian glands 10 in order to melt, soften, or loosen any obstructions in the meibomian glands prior to attempting extraction or expression of the obstructions from the meibomian glands. FIG. 4 illustrates an eye 26 having an eyelid 28, which contains a plurality of meibomian glands 30. An RF electrode 32 is provided for directing RF energy to the meibomian glands 30. The RF electrode 32 may be located proximate to the eyelid 28. In one embodiment, the RF electrode 32 does not make contact with the eyelid 28, while in another embodiment, the RF electrode 32 slightly touches the eyelid 28. In the embodiment shown in FIG. 4, the RF electrode 32 is positioned proximate to an outer surface of the eyelid 28 and is configured to direct RF energy in a direction into the eyelid, as shown by arrows 34 in FIG. 4, such that the RF energy may selectively target the meibomian glands, and in particular, any obstructions in the meibomian glands.

In one embodiment, in lieu of an RF electrode, a microwave antenna configured to direct microwave energy to the internal portions of the eyelid 28 may be used.

In this manner, RF or microwave energy may be utilized to pinpoint thermal energy at specific target tissues. In addition, RF and microwave energy can be manipulated to be absorbed or directed for a certain type of cellular content or tissue material make up. For instance, the RF or microwave energy waveforms can be directed to be absorbed preferentially by energy absorbing cellular fluids, saline or lipid containing materials found in the ducts, channels, or acini of the meibomian glands rather than the cellular structures of the meibomian glands themselves. Pulsed waveform energy may react more preferentially on certain cellular fluids and contents than continuous waveforms. Specifically for the removal of meibomian gland obstructions, the desired temperature range for liquefying lipid containing obstructions is quickly and easily achievable using RF energy. Thus, in the area of removing meibomian gland obstructions, a series of short pulsed RF energy waves or microwaves could preferentially heat gland contents within the eyelid without raising the temperature of surrounding tissues or unintended tissue surfaces significantly.

Besides selectively heating different types of tissue contents and not heating indiscriminately surrounding tissue, microwave/RF energy can be directed to perform at a predetermined depth as seen in hyperthermia treatments or when treating a specific depth within the wall of the arterial vessel. For meibomian gland obstructions, being able to treat within the duct itself will have advantages by avoiding thermal injury to eyelid tissue surfaces, which are in close proximity to the ducts, and the eye, cornea, and other unintended structures that are clearly thermally sensitive tissues.

Figure 5:
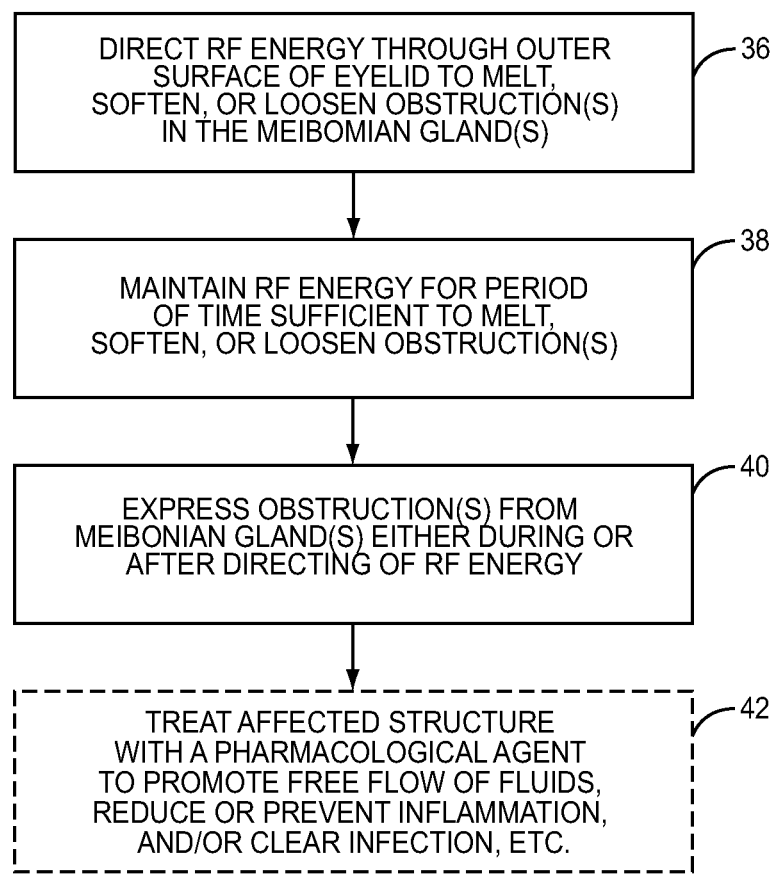
FIG. 5 is a flowchart illustrating an exemplary process of directing RF energy to the eyelid relating to treating the meibomian glands.

FIG. 5 is a flowchart illustrating an exemplary process of directing RF energy to the eyelid relating to treating the meibomian glands. In this regard, in one embodiment, RF energy is applied via the RF electrode 32 through a surface of the eyelid to melt, soften, or loosen obstructions in the meibomian glands to treat MGD in basic form, as shown in the flowchart of FIG. 5. In FIG. 5, RF energy is transmitted from a RF source (see, e.g., RF generator 64, FIG. 10) to the RF electrode 32 and applied through a surface of the eyelid 28 to melt, loosen, or soften obstructions or occlusions in the meibomian glands 30 (step 36). For example, in one embodiment, the RF energy may be applied to raise the temperature of the tissue within the meibomian glands 30, as well as any obstructions within the meibomian glands 30 to 43-47 degrees Celsius. In other embodiment, the temperature range may vary. A time range to direct RF energy may be a period between 1-10 minutes, and may be limited to a range of 3-6 minutes. The RF energy may be regulated, meaning that a RF controller means or element (see, e.g., controller 68 in FIG. 11) is used to control the application of RF energy such that the temperatures and means of application are safe for the structures of the eye, including but not limited to the inner surface of the eyelid, and a sufficient temperature is reached for melting, loosening, or softening an occlusion or obstruction in the meibomian gland. By sufficient temperature, this refers to the amount of RF energy needed to heat the palpebral conjunctiva to achieve the desired melting, loosening, or softening of the obstruction.

Still referring to FIG. 5, the application of the RF energy may be maintained for a period of time until the temperature reaches the desired level sufficient to melt, loosen, or soften the obstructions or occlusions (step 38). For example, the heat may be applied for 1 to 10 minutes in one embodiment. In other embodiments, various amounts of time for the RF energy application may be used. Thereafter, either during the application of the RF energy or after, obstructions or occlusions in the meibomian glands may be expressed so that sebum flow is restored from the glands to establish a sufficient lipid layer (step 40).

In one embodiment, the ability to effectively and more efficiently raise the temperature at the meibomian glands may prove instrumental in melting, loosening, or softening obstructions or occlusions in the meibomian gland to reach the loosening or melting point of the obstruction or occlusion.

As used herein, the terms "melt," "loosen," and "soften" and variants thereof are to be interpreted broadly. These terms broadly encompass any change in form or state of the obstructive or occluding material causing or contributing to an obstruction or occlusion related to a disorder of the eye or eyelid structure to a form such that the obstruction or occlusion can be more easily freed or expressed. This includes, but is not limited to, changing form from less of a solid form or state to more of a liquefied form or state, including but not limited to dissolving, loosening, liquefying, and/or softening of the obstructive or occluding material to be removed, and/or dissolving, loosening, liquefying, or softening of material that holds together particulate matters causing or contributing towards the obstruction or occlusion related to a disorder of the eye or eyelid structure and other modalities.

Referring back to FIG. 5, optionally, after expression of the occlusions or obstructions is performed (step 40), an optional pharmacological agent may be applied to the meibomian gland to promote the free flow of sebum and/or reduce or prevent inflammation or infections of the eye or eyelids (step 42). Many pharmacological agents have been proposed for treatment of dry eye syndrome, any of which may be effective or more effective upon clearing of obstructions within the meibomian glands. Some of the pharmacological agents that may be utilized include, but are not limited to: antibiotics such as topical or oral tetracycline and chemically modified tetracycline, testosterone, topical or oral corticosteroids, topical androgens or androgen analogues, omega 3 fatty acid compounds such as fish oils, Laennec, enzymes that promote lipid production, agents that stimulate production of enzymes that promote lipid production, and/or any agent which acts as a secretagogue to enhance meibomian gland secretion or secretion of other tear components. For example, androgen and androgen analogues and TGF-beta have been reported to act as a secretagogue to enhance meibomian gland secretion. These compounds are illustrative examples of appropriate pharmacological agents, but those skilled in the art will appreciate that other pharmacological compounds may be utilized.

Treatment to remove the obstruction may involve the application of an external regulated force to the eyelid and/or directly over the obstructed orifice to loosen the obstruction within the meibomian gland 10 and the orifice 16 of FIGS. 2 and 3. The means for applying the force may be selected from one or more of a number of modalities. In many of the embodiments disclosed herein, RF energy is discussed. However, the means for applying the force may be selected from one or more of any number of modalities wherein the frequency of vibration may be including low frequency vibration (generally less than 1000 Hz), sonic (generally 1000 Hz to 20,000 Hz) or ultrasonic energy (generally greater than 20,000 Hz), fluid jet such as air or water, microwave energy, needles, laser energy, aspiration/suction, vacuum, pressure, compression, and functional equivalents thereof, in lieu of or in addition to RF energy. In addition, once a modality is chosen, the physician will have to determine the optimum treatment parameters so that each of the foregoing modalities will be applied to the eyelid such that the force (or energy, as appropriate) provided thereby is transmitted through the eyelid tissue to the obstruction. Further, the treatment intensity and length of application of these external forces will vary with the size and composition of the obstruction. Once a treatment protocol is established, the force can either be set per variable within a preselected range. Experiments were performed using an eccentric vibrating motor applied directly to the human eyelids. Bench tests of the vibration revealed the following data points, specifically setting number 3 was shown to be clinically effective to loosen the obstruction within the meibomian gland and orifice:

| Setting | Vibration Freq. (Hz.) | Vibration Amplitude (in/μm) |
|---|---|---|
| 1 | 51 | .001 in. (25.4 μm) |
| 2 | 118 | .004 in. (100 μm) |
| 3 | 165.5 | .0062 in. (157.5 μm) |

Once the obstruction has been loosened from the walls of the meibomian gland 10, it may be operated upon such that it will pass through the orifice 16 in a manner which causes little or no pain or discomfort to the patent. This can be accomplished by heating to soften or liquefy the obstruction 22 or 24 up to a range of thirty seven degrees centigrade (37° C.) to fifty degrees centigrade (50° C.) with the preferred operating range being forty degrees centigrade (40° C.) to forty seven degrees centigrade (47° C.) and desired modality of forty two degrees centigrade (42° C.) to forty six degrees centigrade (46° C.) so that it easily passes through the orifice (or with minimal non-painful expansion thereof). In one embodiment, the heating to soften or liquefy the obstructions 22 or 24 in the meibomian glands is done by RF heating, with the RF electrode 32 as shown in FIG. 4 being one non-limiting example. However, other modalities for heating are possible and may include conduction, convection and radiation supplied by one or more of the following: thermal conduction, thermal convection, ultrasonic energy, laser energy, direct and/or indirect transfer from heat source and microwave energy which may be applied for a preselected period of time. By varying the amplitude, intensity and length of application, some of the foregoing modalities may also be employed to fracture or break up the obstruction. It will be noted that a closed loop feedback control system, well known to those skilled in the art may be employed during heating to measure temperature proximate the eyelid to ensure that the obstruction does, in fact, reach a temperature sufficient to turn the obstructive material into a flowable, liquid or semi-liquid state.

Extraction of the softened, broken apart or fractured obstruction may be accomplished by one or more of the following: needles, micro-needles, aspiration/suction, vacuum, pressure and compression. One embodiment includes a suction system that is placed over the gland orifice may be employed to suck out the components of the softened, loosened or liquefied obstruction or the pieces thereof, as appropriate or alternatively, to employ suction to collect the obstruction as it exits the gland orifice. In order to be clinically effective, the foregoing modalities for extracting or expressing the obstruction should be administered in a fashion that is regulated, i.e., done in a repeatable manner.

Figure 6A:
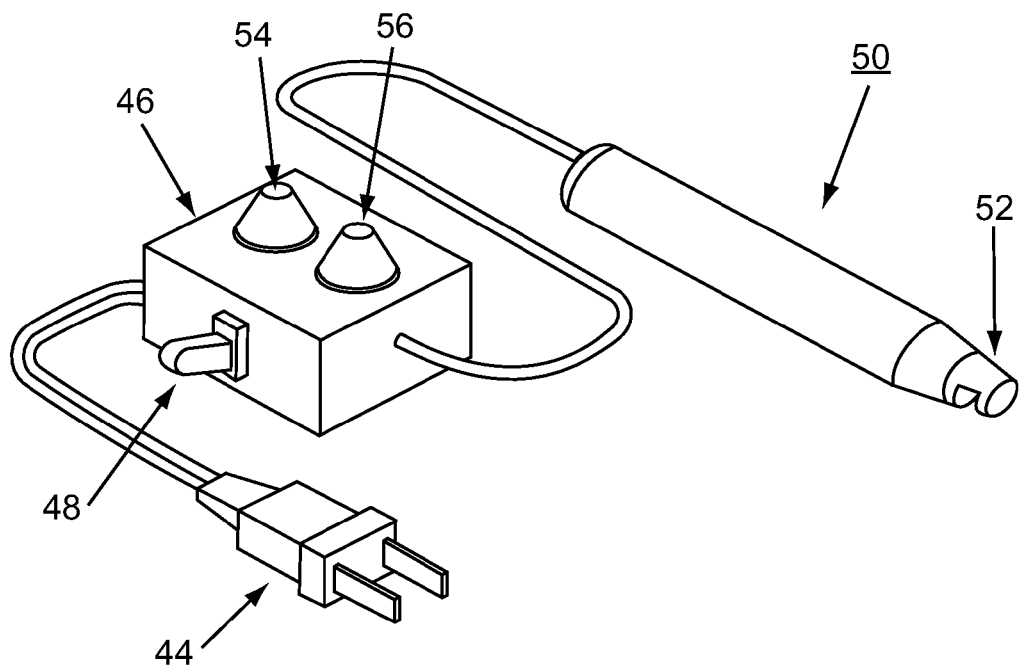
FIG. 6A is a perspective view of a system for clearing obstructed meibomian glands according to an exemplary embodiment.

In addition to the apparatus described above in FIG. 4 that includes an RF electrode 32 positioned proximate to an outer surface of the eyelid 28 and configured to direct RF energy in a direction into the eyelid, other apparatuses may be used to aid in the extraction or expression of obstructions in the meibomian glands. One embodiment of an apparatus for unplugging the obstructed gland channel 18 of FIG. 3 is schematically illustrated in FIG. 6A. The apparatus comprises an RF source 44 which may be direct current (battery powered) or alternating current (wall socket) as desired. The RF source 44 is connected to a controller, generally indicated at 46, which includes a power on/power off switch 48. The controller 46 includes an RF means 50 for applying an external force to the gland to loosen the obstruction. The RF means 50 in this embodiment includes a probe 52, which is adapted to vibrate at a preselected frequency at preselected amplitude. The probe 52 may vibrate at sonic or ultrasonic frequencies as needed. In addition, means for varying the frequency 54 and amplitude 56 of the probe output, well known to those skilled in the art, are provided. The RF means 50 may be used for applying the regulated external force or regulated energy to the obstruction. Although the embodiment shown in FIG. 4 illustrates an RF source 44 and an RF means 40, other types of power sources and means for applying a force may be used, including but not limited to a fluid jet, air fluid, water fluid, microwave energy, needles, micro-needles, laser energy, RF energy, aspiration, suction, vacuum, pressure, piezoelectric, and compression.

Figure 6B:
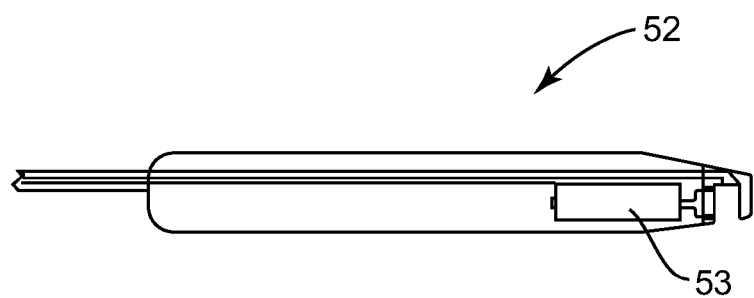
FIG. 6B is a broken away side view of the probe tip employed in the embodiment of FIG. 6A.
Figure 7A:
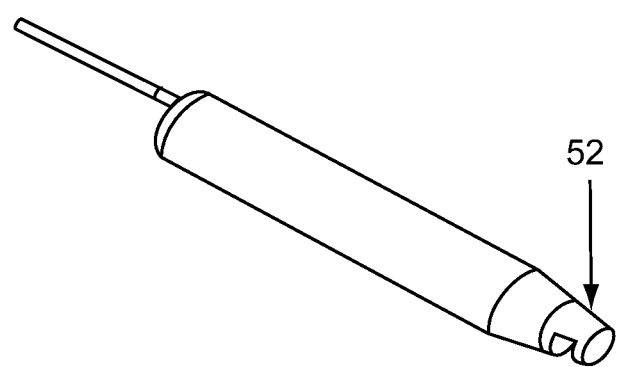
FIG. 7A is a perspective view of another exemplary probe tip.
Figure 7B:
Figure 7C:
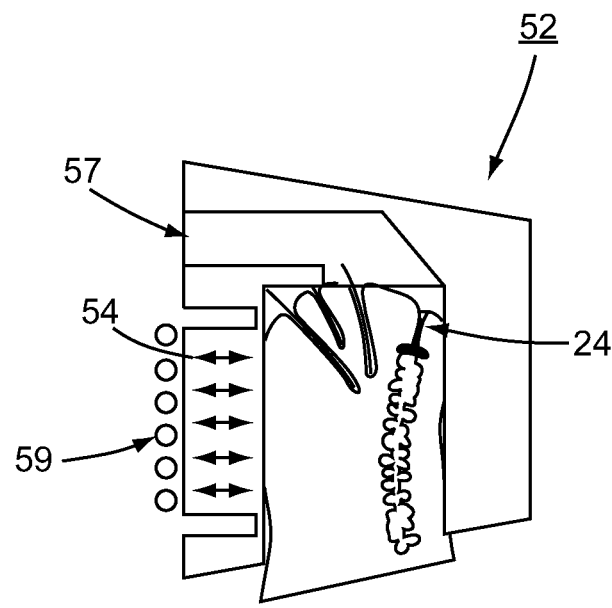
FIG. 7C is a broken away side view of the probe tip of FIGS. 4a and 5a in place on an eyelid.

Turning now to FIG. 6B, a small ultrasonic probe 52 (and specifically the probe tip) is illustrated in FIG. 7C in place on the eyelid. The probe 52 is adapted to deliver RF energy through the skin into the obstruction 22 or 24 (as shown in FIG. 3) in order to loosen, liquefy, and/or fracture the obstruction. In one embodiment, as seen in FIGS. 6B and 7B, the probe 52 may contain an RF element 53 for directing RF energy though an eyelid to selectively target an obstruction in the meibomian gland in order to soften, melt, or liquefy the obstruction. The RF element may be similar to the RF electrode shown in FIG. 4 in one embodiment. More specifically, by tuning the probe output so that the obstruction 22 or 24 resonates (by adjusting the frequency and amplitude of the signal) energy is efficiently transferred to the obstruction and sympathetic vibration of the obstruction 22 or 24 occurs with minimal energy transfer to the surrounding tissues. In some instances, vibration alone may be sufficient to change the characteristics of the obstruction 22 or 24 such that vigorous blinking may express the obstruction remnants.

In addition to vibration alternative force, energy, aspiration and/or chemical/pharmacological agents can be used to open up the channel 18. The probe may be further equipped with aspiration means 57 (best illustrated in FIG. 7C) for introducing aspiration, suction or vacuum into the gland channel 18 to evacuate the obstruction remnants. Alternatively, heat and aspiration may be employed in lieu of or in addition vibration.

In another embodiment, the probe 52 may be equipped with a RF heating element 59, which may be regulated to provide relatively precise amounts of energy in the previously mentioned ranges that assists in softening, liquifying or melting the obstruction 22 or 24 via heat transfer through the tissue when the probe is placed against the tissue. In a further embodiment, the probe 52 may use the RF element 53 to deliver vibrational and/or thermal energy to the obstruction 22 or 24 without contacting the gland.

In other embodiments, a solid state heating element may be used in place of or in addition to the RF heating element 59. Further, in other embodiments, other potential energy sources may be used, such as laser light supplied by titanium, argon, krypton or microwave energy.

After the obstruction is softened, melted, loosened, liquefied, and/or fractured, extraction of the obstruction would be accomplished by any of the means described herein.

Figure 8A:
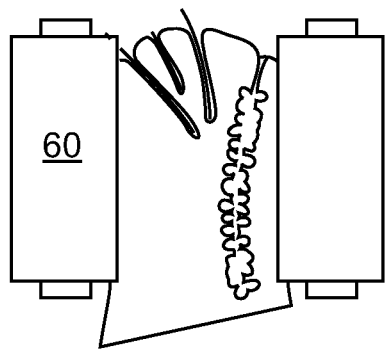
FIG. 8A is a side view of an exemplary embodiment of the probe tip having rollers for clearing obstructed meibomian glands.
Figure 8B:
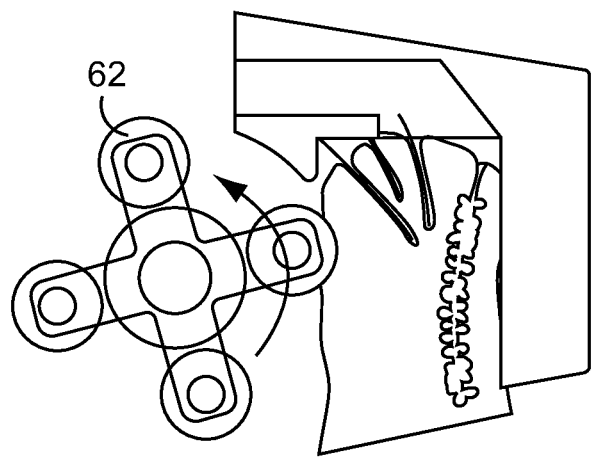
Figure 9:
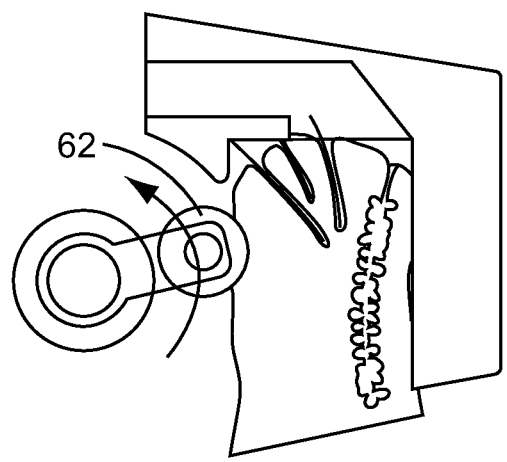
FIG. 9 is a side view of an exemplary embodiment of a probe tip having rollers for clearing obstructed meibomian glands.

In one embodiment, pressure may be applied to the tissue as shown in FIGS. 8A, 8B, and 9 by rollers (or drums) 60 or 62 which are placed in front of and/or behind the meibomian gland with the rollers applying constant regulated pressure to the meibomian glands to apply a "milking" type force to expel the obstruction to return the gland to normal secretion levels. The rollers can be connected to heat, aspiration, vacuum, and/or suction that operate as described herein.

In operation, the physician would place the rollers 62 in contact with the eyelid, either inside, outside or both. Lateral movement of the rollers 62 would cause pressure to be applied to the gland to remove the obstruction. Alternatively, aspiration, suction and/or vacuum could be applied to extract the obstruction and material from the vicinity of the gland opening. In addition, depending upon the obstruction, aspiration, suction and/or vacuum alone may be sufficient to extract the obstruction.

Additional features may also be provided to the rollers 62 such as a regulated RF heating element (not shown) which could be placed in the outer covering near the tip as shown in FIGS. 6A-7C. In addition, the roller 62 could be equipped such that ultrasonic energy could be delivered to the obstruction as discussed herein above.

Figure 10:
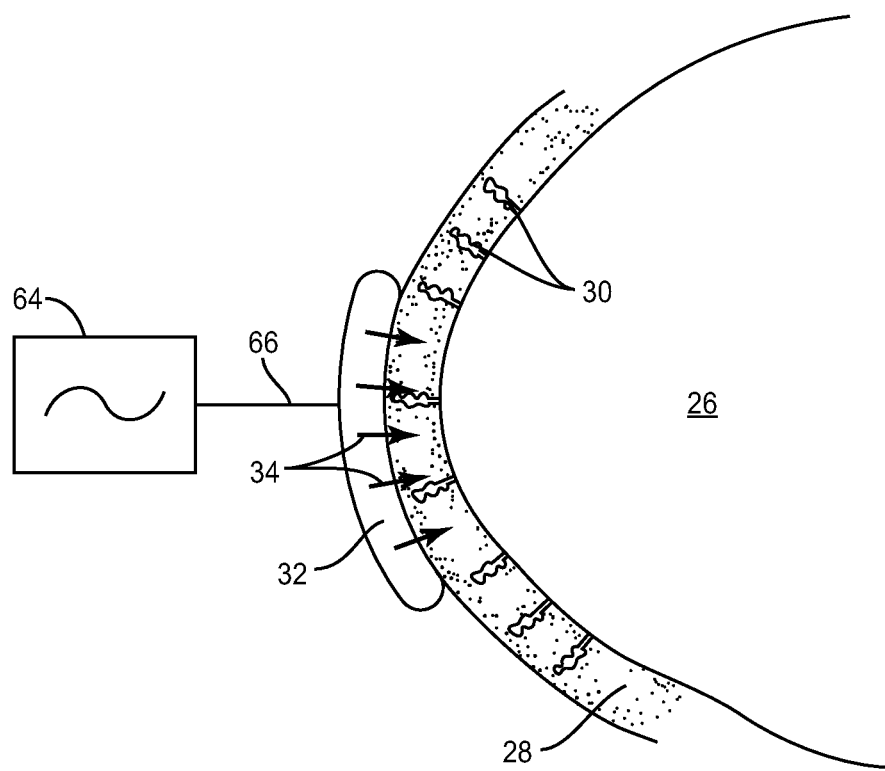
FIG. 10 illustrates an exemplary system for directing RF energy from a RF generator to an RF electrode positioned proximate an eyelid.

The RF energy used to soften the obstructions in the meibomian glands may be generated by a RF source, or generator 64, as shown in FIG. 10. FIG. 10 illustrates an exemplary system for directing RF energy from a RF generator 64 to an RF electrode 32 positioned proximate an eyelid 28. In one embodiment, the RF generator 64 may be an electrical surgical unit (ESU). The RF generator 64 may be directly connected to the RF electrode 32 via a connection 66, which may be an electrical wire in one embodiment. The RF generator 64 can be controlled by a physician or other trained professional via a footswitch, hand button, or finger button actuation.

Figure 11:
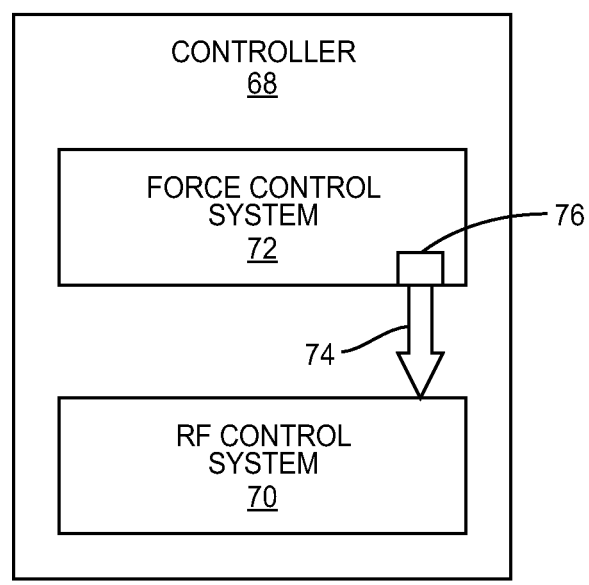
FIG. 11 illustrates a controller to be used with the system of FIG. 10 for facilitating selective and controllable communication of RF energy and/or force to the eyelid, according to one embodiment.

FIG. 11 illustrates a controller 68 to be used with the system of FIG. 10 for facilitating selective and controllable communication of RF energy and/or force to the eyelid, according to one embodiment. The controller 68 may include a RF control system 70 and a force control system 72. The force control system 72 is the control component within the controller 68 that controls the force applied to the patient's eye. The RF control system 70 is the control component within the controller 68 that controls the RF energy applied to the patient's eye. The force control system 72 also communicates the pressure in tubing 74 to a force sensor 76 within the force control system 72. The force sensor 76 is used to determine a pressure level in the tubing 174 as well as to provide feedback to the controller 68 to provide the various functions and controls for the system, as will be described in more detail below. The force sensor 76 also allows the recordation of pressure data to be recorded by the controller 68, or an external data acquisition device (not shown) coupled to the controller 68, if desired.

The application of RF energy may be regulated, meaning that a RF controller means or element is controlled to be within the temperatures and means that are safe for the structures of the eye, including the inner surface of the eyelid, and at a sufficient temperature for melting, loosening, or softening an occlusion or obstruction in the meibomian gland. The RF energy is maintained for a period of time sufficient to melt, loosen, or soften the occlusions or obstructions. Either during the application of the RF energy or after the application of RF energy has been discontinued, the occlusions or obstructions in the meibomian glands are expressed to remove obstructions or occlusions thus providing an improved pathway to restore or improve sebum flow from the gland.

In one embodiment, increasing the temperature of the surface of the palpebral conjunctiva to at least 37 degrees Celsius can begin to provide therapeutic effect for milder cases of MGD. A therapeutic temperature can be any temperature above body temperature. One preferred range for treatment is 43 to 45 degrees Celsius, with a target of 43 to 44.5 degrees Celsius. Temperature in this range has been found effective and comfortable to the patient when treating MGD. A time range to direct the RF energy may be a period between 1-10 minutes, and may be limited to a range of 3-6 minutes.

In one embodiment, the application of RF energy may be regulated. Regulated RF energy can include controlling the application of RF energy according to a temperature profile. The temperature profile may be a constant temperature, including ramp-ups, ramp-downs, peaks and valleys. Further, the temperature profile may include heat pulses or be modulated with various characteristics, including the use of on/off switching or pulse width modulation (PWM) techniques for example. The use of modulated RF energy may allow the temperature to be raised even higher at the eyelid without damages to the patient's eyelid since the increased temperatures are applied for shorter periods of time. Obstructions or occlusions in the meibomian glands may have melting, loosening, or softening points that are beyond temperatures that may be applied without the use of modulated RF energy. The temperature needed to melt, loosen, or soften obstructions or occlusions may depend on how keratinized the obstruction or occlusion is. Not all obstructions or occlusions have the same melting, loosening, or softening points.

By example only, elevated temperatures between 45 and 55 degrees Celsius may be possible when directing regulated RF energy, especially if the eyelid has been anesthetized. However, the RF energy must always be applied to the eyelid at temperatures that take into consideration the pain response of the patient as well as whether damage will occur to the patient's eyelid and/or surrounding tissues. Depending on the severity of the patient's MGD or the patient's pain tolerance, elevated temperatures may be used with patient's on an individualized basis when directing RF energy. It has been found that lighter skinned patients can generally tolerate less heat than darker skinned patients, and darker skinned patients tend to exhibit less inflammation as a result of exposure to the heat. Other factors, including humidity, may contribute to a patient's tolerate to greater temperatures. For example, humans can generally tolerate temperatures up to 70 to 80 degrees Celsius in dry saunas where humidity is low. Application of RF energy in higher humidity environments may cause pain and/or burns to occur at lower temperatures.

Severe cases of MGD that cause substantial irritation or risk to the patient may even call for temperatures that would produce category one or two burns to the patient's eyelid, since these burns generally heal. Temperatures that cause category three burns should be avoided. In summary, treatment times and/or temperature can be adjusted to account for these differences. Embodiments disclosed herein are not limited to any particular temperature or time ranges as long as therapeutic temperature is being applied.

The regulated RF energy can be maintained at a therapeutic temperature for a treatment period. The treatment period can be approximately 1 to 10 minutes for example. The RF energy could also be repeatedly applied and maintained for a desired period of time to keep the occlusion or obstruction in a melted, loosened, or softened state. Either during or after such treatment by regulated RF energy, mechanical expression of lipids and other fluids from the meibomian glands has been found to clear obstructions which have essentially melted or been placed in a suspension state (by virtue of melting materials binding solids together).

Also, agents, such as Restasis (cyclosporine A), that replace or promote production of the tear component may also be applied more effectively after treating the meibomian glands according to the embodiments disclosed herein. Treating the meibomian glands improves the lipid layer, thus reducing evaporation and conserving the aqueous layer. Conservation of the aqueous layer reduces the need for tear substitutes to be applied through tear component agents. Thus, tear component agents may not have to be used as often when employing the embodiments disclosed herein to treat a patient's MGD.

In another embodiment, a method and apparatus for treating meibomian gland disease (MGD) using RF/microwave energy for rapid heating and removal of MGD obstructions is disclosed. In this embodiment, an RF electrode may be part of an eyecup apparatus, as shown in FIGS. 12A-14. It is the objective of this method and apparatus for treating MGD to reduce procedural times and decrease patient discomfort. It is a further objective to allow patients on a cosmetic basis to return to normal activities without a need for a recovery time from pain, discomfort, pigmentation at the eye lid, or aesthetic discoloration (redness) visible post-treatment. It is a further objective of the described eye cup mechanism to provide for the application of therapeutic drugs or topical pharmacological agents directly at the site of the meibomian gland openings immediately post treatment all within the same device and in the same procedural setting.

Figure 12A:
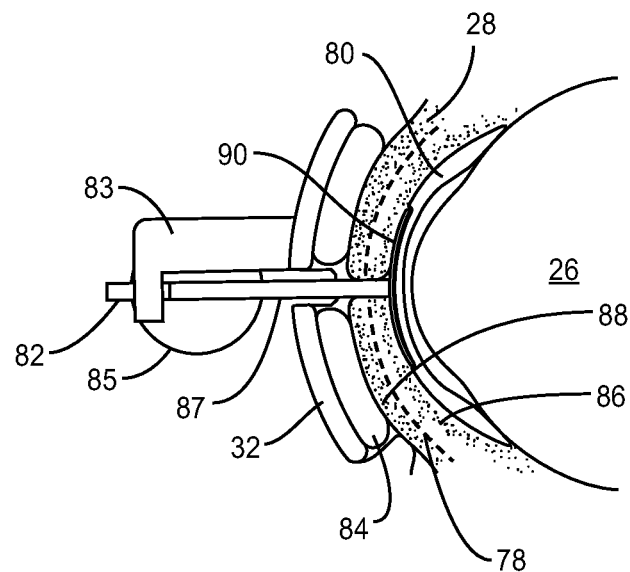
FIG. 12A is a broken side view of an exemplary eyecup comprising an exemplary RF electrode configured to direct RF energy to the internal portions of meibomian glands according to one embodiment.

FIG. 12A is a broken side view of an exemplary eyecup comprising an exemplary RF electrode configured to direct RF energy to the internal portions of meibomian glands according to one embodiment. In one embodiment, heating the meibomian glands, as well as any obstructions within the meibomian glands, from the outside of an eyelid 28 is accomplished by the use of RF or microwave energy. The energy source is directed to focus below the skin layer and through the tarsal plate into an area 78 of an eyelid 28 where meibomian glands are located.

Looking at FIG. 12A, an eyecup 80 may be provided and positioned on the surface of the eye 26 behind the inner surface of the eyelid 28. The eyecup 80 is configured to overlie the outer surface of the eyelid 28 and substantially conform to the surface shape thereof. Extending perpendicularly outward from the body of the eyecup 80 is a pair of flexible spaced apart opposing cantilevered engagement arms 83 which include integrally molded finger grips or handles 85 as part of handle 87. An RF delivery means may be provided as a RF electrode 32. A connection 82, as seen in FIG. 12A, is configured to be connected to an RF generator, such as RF generator 64 in FIG. 10, to allow RF energy to be generated at RF electrode 32. The eyecup 80 further includes a cooling mechanism 84. As described above, the application of the RF energy below the skin layer and into the tarsal plate can also be achieved with combination with a skin cooling mechanism, such as cooling mechanism 84. In one embodiment, the surface of the RF electrode 32 does not heat the skin layer directly. The RF electrode 32 or other RF energy delivery means can be located above the skin layer by use of a spacer or insulator. By use of an insulator, the skin layer is not heated directly.

In one embodiment, the cooling mechanism 84 may be a cooling membrane. By use of a cooling membrane, as shown in FIGS. 12A-13, the skin layer stays unheated while the gland duct materials are being heated. In one embodiment, the cooling membrane is a bladder that has continuous flowing coolant media to maintain low skin layer temperatures. In one embodiment, the coolant could be cryogenic media. In addition, the coolant could be a reduced temperature or iced saline solution. In one embodiment, the cooling membrane is a vessel with an internal air vacuum to act as an insulator. In another embodiment, the cooling membrane is a conduit with flowing air running through it to reduce surface temperature heating.

In one embodiment, RF/microwave energy can be modified by altering the wave length, wave form, power, frequency, pulse duration or continuous waveforms, and shape of the energy delivering means.

Figure 12B:
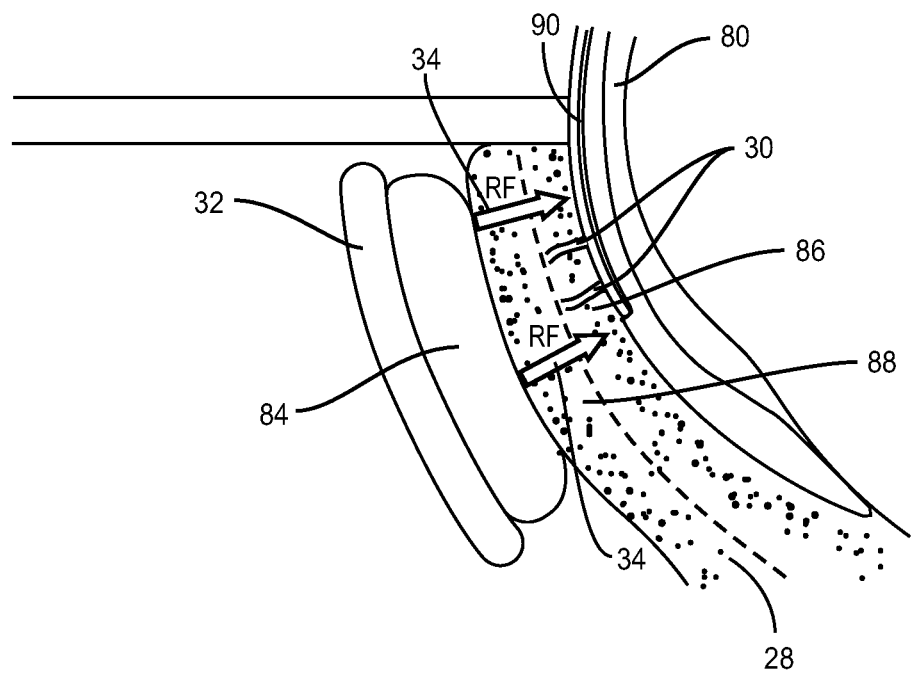
FIG. 12B is a close up view of the exemplary eyecup of FIG. 12A showing RF energy being applied to the internal portions of meibomian glands according to one embodiment.
Figure 13:
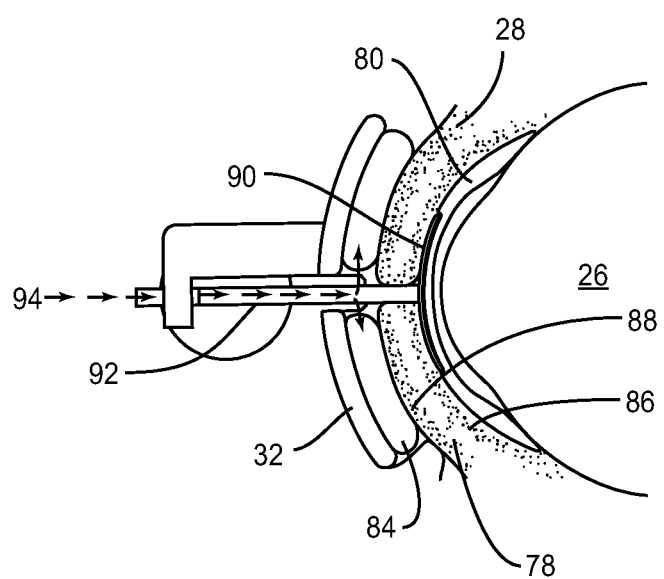
FIG. 13 is a broken side view of an exemplary eyecup comprising an exemplary cooling mechanism and an exemplary RF electrode configured to direct RF energy to the internal portions of meibomian glands according to one embodiment.

The above modifications are directed towards preferentially heating the gland duct materials as seen in FIG. 12B. A zone of preferential heating 86 and a zone of preferential cooling 84 may be created. The RF energy generated by the RF electrode 32 may be targeted in the zone of preferential heating 86, where the meibomian glands 30 are located. Gland duct materials will have different electrical and thermal conductivity properties than their surrounding tissues. There can be significant differences in dielectric properties between the duct materials and the surrounding gland and eye lid tissues themselves. Historically in other RF applications, these differences can be more pronounced at lower frequencies and in some clinical applications, below 100 kHz. The systems disclosed herein can efficiently direct RF energy to tissues below the skin layer without substantially heating the skin layer itself. Other systems that describe heating below the skin layer without a separate mechanism for cooling the skin can be found in (WO/2006/077567), entitled "Improved System and Method for Heating Biological Tissue Via RF Energy" or U.S. Pat. No. 5,948,011, entitled "Method for controlled contraction of collagen tissue via non-continuous energy delivery."

In one embodiment, as shown in FIGS. 12A-15, a specially designed eye cup (described below) prevents thermal energy from being delivered to the globe and sensitive structures of the eye. The heating mechanism of the eyecup is nearly instantaneous due to the mechanism of RF heating, conductivity of cellular components, and preferential heating of lipid containing cellular components. Dead cells, dried out cellular matter, or material clusters devoid of water or fluid components would tend to be affected less by RF energy than other cells.

By focusing the RF energy below the skin layer, a more efficient thermal process being directed at the site of meibomian glands could be achieved without damaging outer layer tissues in a more rapid time frame. The meibomian glands 30 in particular are located near the inside of the eyelid 28. As seen in FIG. 12A, a temperature monitoring means 90 may be provided on the eye cup 80 in order to maintain temperatures below 45 degrees Celsius (or any temperature above body temperature below 54 degrees Celsius).

As described above, the application of the RF energy below the skin layer and into the tarsal plate can also be achieved with combination with a skin cooling mechanism. In one embodiment, the surface of the energy delivering means does not heat the skin layer directly. The RF electrode or other RF energy delivery means can be located above the skin layer by use of a spacer. By use of an insulator, the skin layer is not heated directly.

In addition, in one embodiment, the system may also include a cooling membrane. By use of a cooling membrane, as shown in FIGS. 12A-13, the skin layer stays unheated while the gland duct materials are being heated. In one embodiment, a conduit 92 may be provided as part of the handle 87 or some other part of the eyecup 80 in order to provide cooling media to be introduced to the eye area, as indicated by the arrows 94 in FIG. 13. In another embodiment, the cooling membrane is a bladder that has continuous flowing coolant media to maintain low skin layer temperatures. In one embodiment, the coolant may be could be cryogenic media. In addition, the coolant could be a reduced temperature or iced saline solution. In one embodiment, the cooling membrane is a vessel with an internal air vacuum to act as an insulator. In another embodiment, the cooling membrane is a conduit (similar to conduit 92 in FIG. 13) with flowing air running through it to reduce surface temperature heating. The surface of the RF electrode 32 or RF energy delivering means and/or insulator may also apply mechanical pressure (beyond stabilizing the energy delivery mechanism) to express gland duct materials for greater patient comfort and without marking the outer/visible eyelid.

Figure 14:
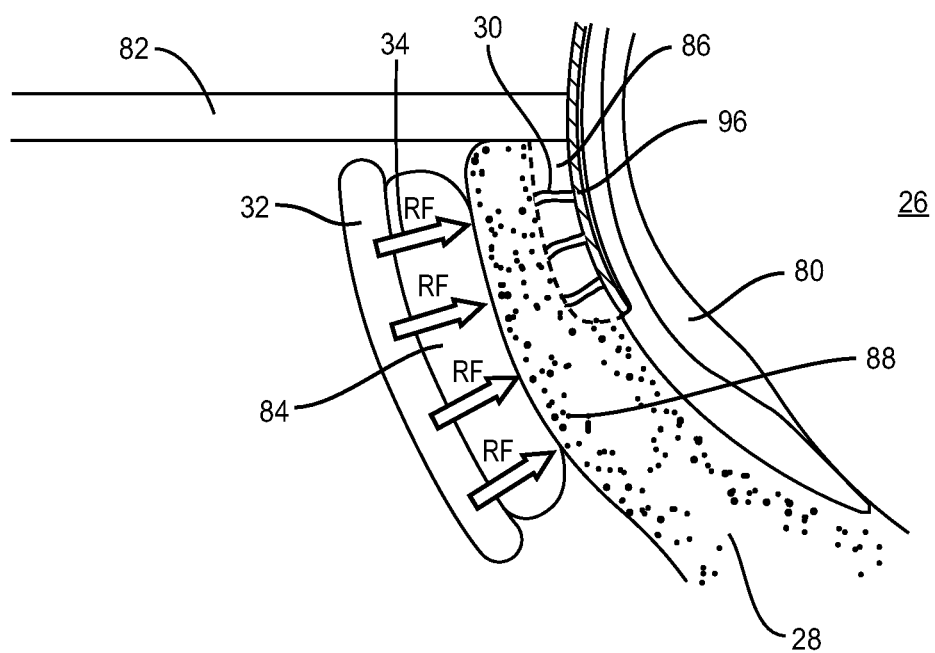
FIG. 14 is a broken side view of an exemplary eyecup comprising an exemplary RF electrode located on the outside of an eyelid configured to preferentially heat an exemplary conductive plate located on a periphery of the exemplary eyecup.

In another embodiment, the RF electrode 32 or RF energy means on the outside of the eyelid 28 preferentially heats a conductive plate or plates 96 located on the periphery of the eye cup 80, as seen in FIG. 14. As the conductive plate(s) 96 are heated to controlled temperatures, the adjacent inner eyelid 28 is heated by thermal conductivity, as shown in FIG. 14. In particular, the zone 86 where the meibomian glands 30 are located is preferentially heated as compared to the other tissues of the eyelid 28.

Figure 15:
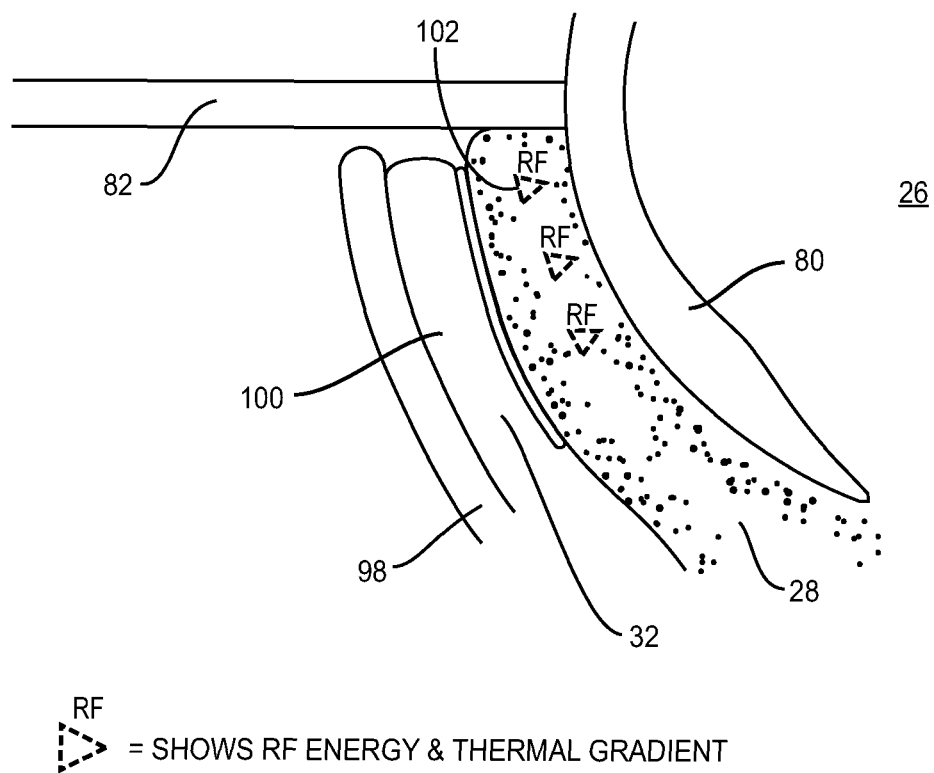
FIG. 15 is a broken side view of an exemplary eyecup comprising an exemplary RF electrode positioned on an outer surface of an eyelid.

In one embodiment, as shown in FIG. 15, an RF electrode 32 (or microwave antenna) is placed on an outer surface of the eyelid 28 to direct RF/microwave energy rapidly to an internal portion of meibomian glands 30 within the eyelid 28. The RF energy is applied to selectively target gland duct contents, including any obstructions that may be within the channel or duct of the meibomian gland. The RF energy is applied completely through the eyelid 28, but does not heat the outer surface of the eyelid 28. In addition, the microwave/RF energy in this instance equally would not be directed on the inner surface of the eyelid 28 or the orifices 16 of the meibomian glands 30. Instead, only the internal duct or channel 18 of the meibomian glands 30 is heated by the application of the RF energy in this embodiment.

FIG. 15 is a broken side view of an exemplary eyecup comprising an exemplary RF electrode positioned on an outer surface of an eyelid. An eyecup 80 is positioned as described above. An RF electrode 32 is positioned proximate the outer surface of eyelid 28, The eyecup 80 also comprises a support structure 98 and an expression means 100, which may be used as a backplate to apply pressure to express melted or softened obstructions from the meibomian glands.

One advantage of the single electrode, outer eyelid system illustrated in FIG. 15 is that the RF electrode 32 directs RF energy within the eyelid tissue at a predetermined depth while structurally the electronics of the system resides on the exterior of the eyelid 28, thereby decreasing the amount of materials required to fit underneath the eyelid 28 during treatment, as seen in FIG. 15. The triangles 102 show where the RF energy is being directed and the thermal gradient created thereby.

Another advantage of having the RF electrode 32 on the exterior of the eyelid 28 is that the RF electrode 32 will not be in the location where expressed materials accumulate. Expressed fluids from the inner eyelid will not be obstructed by the physical presence of the RF electrode 32 and its electronics and the fluid collection process will occur unimpeded. In addition, an RF electrode 32 on the exterior location will not be affected in performance by the volume or mass of expressed materials from the glands. In general for this embodiment, the RF electrode 32 will not interfere with any aspiration or collection mechanism for the expressed materials and vice versa.

Microwave and RF energy may be utilized to pinpoint thermal energy at specific target tissues. In addition, RF and microwave energy can be manipulated to be absorbed or directed for a certain type of cellular content or tissue material make up. For instance, the RF or microwave energy waveforms can be directed to be absorbed preferentially by energy absorbing cellular fluids, saline or lipid containing materials found in the ducts, channels, or acini of the meibomian glands rather than the cellular structures of the meibomian glands themselves. Pulsed waveform energy may react more preferentially on certain cellular fluids and contents than continuous waveforms. Specifically for the removal of meibomian gland obstructions, the desired temperature range for liquefying lipid containing obstructions is quickly and easily achievable using RF energy. Thus, in the area of removing meibomian gland obstructions, a series of short pulsed RF energy waves or microwaves could preferentially heat gland contents within the eyelid without raising the temperature of surrounding tissues or unintended tissue surfaces significantly.

Besides selectively heating different types of tissue contents and not heating indiscriminately surrounding tissue, microwave/RF energy can be directed to perform at a predetermined depth as seen in hyperthermia treatments or when treating a specific depth within the wall of the arterial vessel. For meibomian gland obstructions, being able to treat within the duct itself will have advantages by avoiding thermal injury to eyelid tissue surfaces, which are in close proximity to the ducts, and the eye, cornea, and other unintended structures that are clearly thermally sensitive tissues.

Another important benefit with the described systems is that microwave/RF energy can provide a very rapid direct internal heating source. The clear advantage with this would be an overall decrease in procedural time and reducing patient discomfort from the procedure. In addition since the thermal energy does not require conductive heating or a thermal gradient through tissue to reach its intended target, theoretically terminating the procedure could occur more quickly. Finally, for busy physician practices, shorter procedural times will improve patient flow through the practice.

In FIG. 15, the desired amount of thermal energy to deliver to contents within the meibomian glands is an amount sufficient to heat the contents to between 37 and 45 degrees C. The RF energy or microwave energy can be controlled by a controller, such as controller 68 in FIG. 11, or by the RF generator 64 in FIG. 10, to selectively heat the contents of the ducts and channel of the meibomian glands to a known temperature within the tissues and/or to selectively heat lipid containing materials. This may be done by adjusting the power and duration of the applied RF energy, or by changing the waveform shape (stepped or curved). The waveforms may be pulsed or continuous waveforms. In another embodiment, the shape of the RF electrode or microwave antenna that delivers or emits the RF or microwave energy may be changed to selectively heat the contents of the ducts and channel of the meibomian glands to a known temperature within the tissues and/or to selectively heat lipid containing materials. In this manner, the RF energy will be applied to selectively target any obstructions within the duct, channel, or acini of the meibomian glands to melt, soften, or loosen such obstructions. Once melted, softened, or loosened, the obstructions may be more easily expressed from within the channel of the meibomian gland through an orifice of the meibomian gland.

In another embodiment, the RF electrode 32 may be placed on an inner surface of the eyelid 28. This provides certain advantages over the RF electrode 32 being positioned on the outer surface of the eyelid 28, including but not limited to the ability to effectively and more efficiently raise the temperature at the meibomian glands, which may prove instrumental in melting, loosening, or softening obstructions or occlusions in the meibomian gland to reach the loosening or melting point of the obstruction or occlusion.

Figure 16:
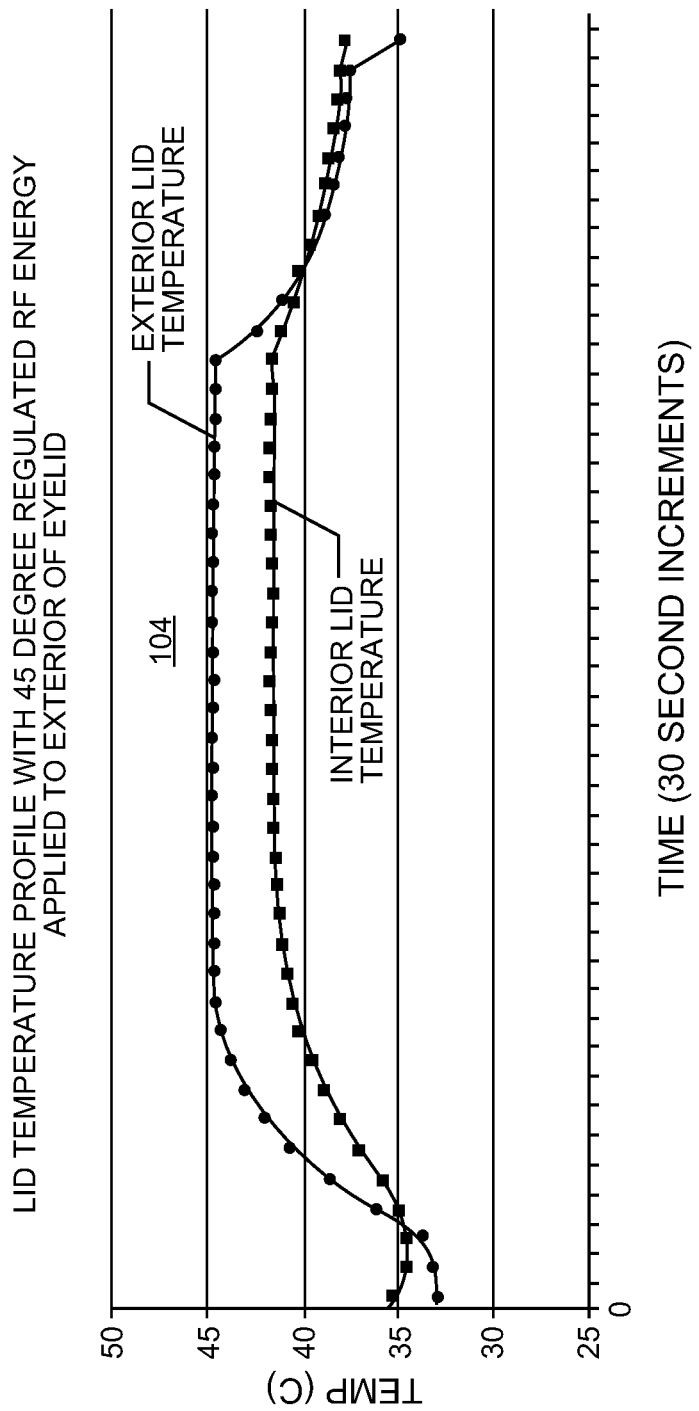
FIG. 16 illustrates an exemplary eyelid temperature profile of an inner and outer eyelid temperature versus time when heat is applied to the exterior of the eyelid.
Figure 17:
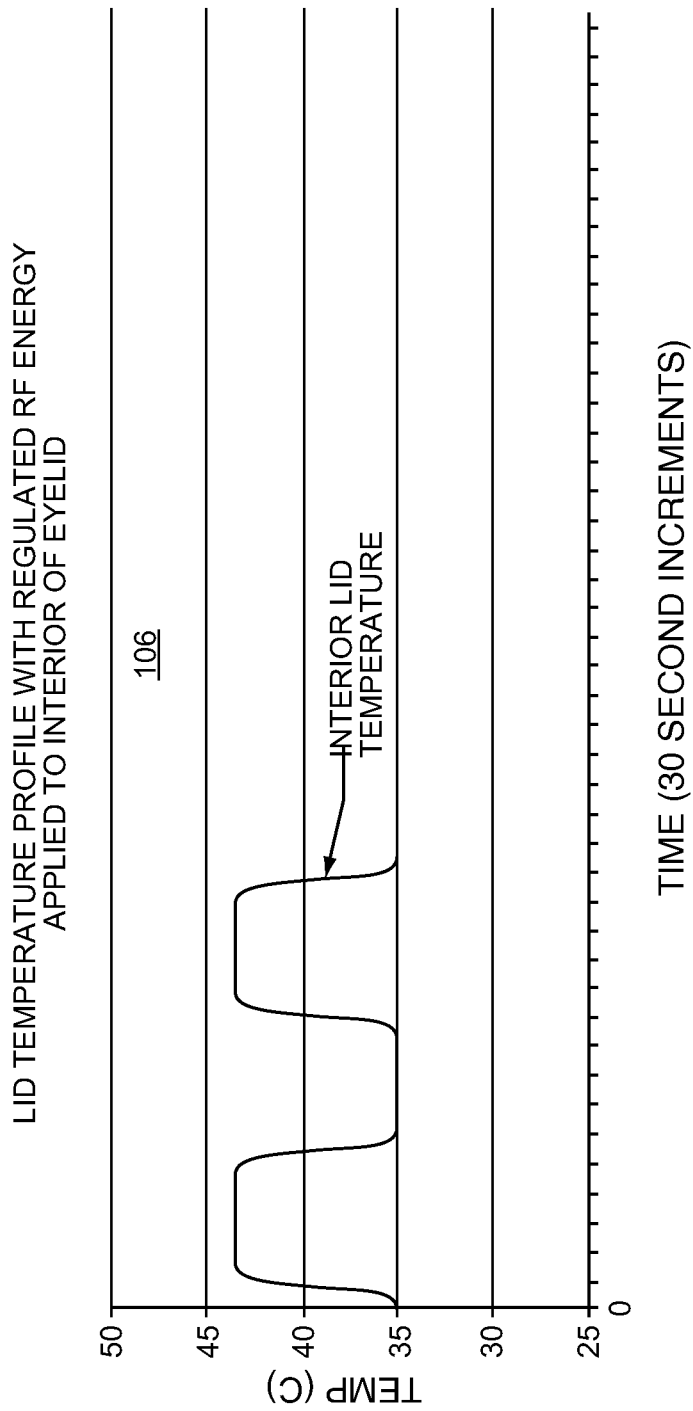
FIG. 17 illustrates an exemplary eyelid lid temperature profile of inside and outside eyelid temperature versus time when heat is applied to the inside the eyelid.

FIG. 16 illustrates an exemplary eyelid temperature profile 104 of an inner and outer eyelid temperature versus time when RF energy is applied to the exterior of the eyelid. FIG. 17 illustrates an exemplary eyelid lid temperature profile 106 of inside and outside eyelid temperature versus time when heat is applied to the inside the eyelid.

An exemplary lid temperature profile 106 that may be generated when RF energy is applied to the inside of the eyelid is illustrated in FIG. 17. There, a graph depicts what the temperature of the inner surface of an eyelid may be as a function of time when a source of RF energy is applied to an example subject patient. A RF electrode attached to the inside of the patient's eyelid is turned on for a period of time. For this patient, it took approximately 30 seconds for the eyelid's inner surface to reach about 44 degrees Celsius. Unlike the lid temperature profile 104 illustrated in FIG. 16, the inner surface of the patient's eyelid did reach a higher temperature when RF energy was applied to the inside of the eyelid. For example, it may only take two to three minutes to bring the temperature at the meibomian glands to 43-45 degrees Celsius or higher when directing RF energy to the inside of the eyelid. In one embodiment, the ability to raise the temperature at the meibomian glands may prove instrumental in melting, loosening, or softening obstructions or occlusions in the meibomian gland to reach the loosening, softening, or melting point of the obstruction or occlusion.

Figure 18:
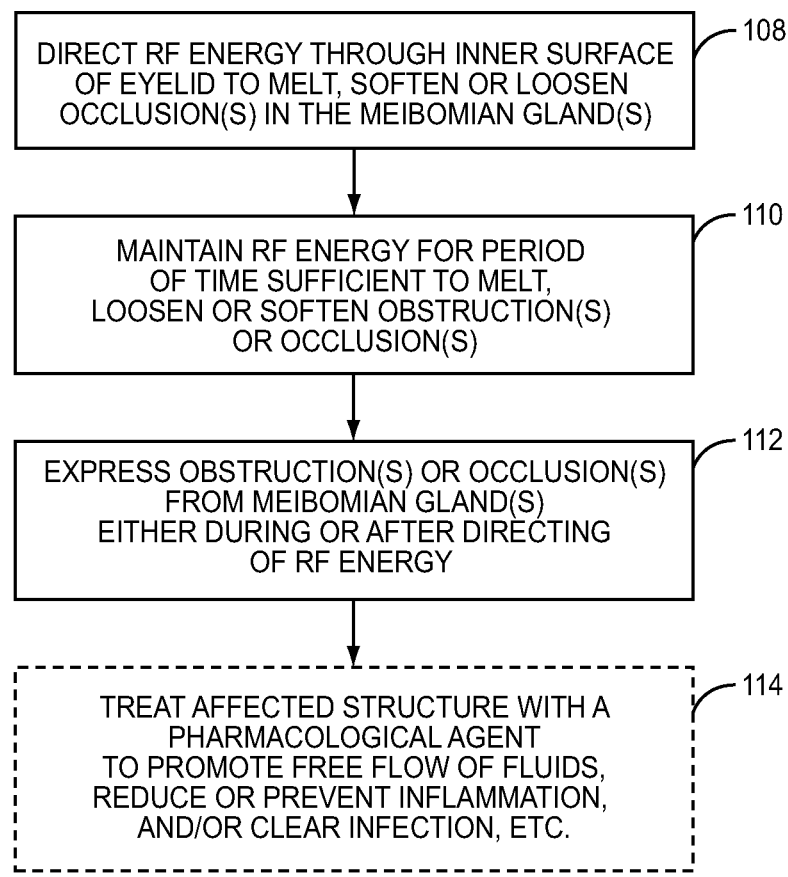
FIG. 18 is a flowchart illustrating an exemplary process of applying heat to the inner eyelid relating to treating meibomian glands.

In this regard, an embodiment to direct RF energy to the inside or inner surface of the eyelid proximate the meibomian glands to treat MGD in basic form is illustrated in the flowchart of FIG. 18. This has the advantage in that it typically takes less time to raise the temperature at the meibomian glands sufficient to melt, loosen, or soften an obstruction or occlusion than if heat were applied directly to the outside of the eyelid. Further, directing RF energy to the inside of the eyelid may allow higher temperatures to be achieved than if the outside of the eyelid were heated.

First, RF energy is applied to the inner surface of the eyelid to a temperature adequate to melt, loosen, or soften obstructions or occlusions in the meibomian glands (step 108). For example, RF energy may be applied to raise the temperature at the inside of the eyelid to 43-47 degrees Celsius in one embodiment, although different temperature ranges may be achieved in other embodiments. A time range to direct the RF energy may be a period between 1-10 minutes, and may be limited to a range of 3-6 minutes in one embodiment. The RF energy may be regulated meaning that a RF control means or element is controlled to be within the temperatures and means that are safe for the inner surface of the eyelid and at a sufficient temperature for melting, loosening, or softening an occlusion or obstruction in the meibomian gland. By sufficient temperature, this refers to the amount of heating needed to heat the palpebral conjunctiva to achieve the desired melting, loosening, or softening of the obstruction. The RF energy may be maintained for a period of time until the temperature reaches the desired level sufficient to melt, loosen, or soften the obstructions or occlusions (step 110). For example, the RF energy may be applied for 1 to 10 minutes in one embodiment, although other embodiments may use different amounts of application time for the RF energy. Thereafter, either during the application of the RF energy or after, obstructions or occlusions in the meibomian glands may be expressed so that sebum flow is restored from the glands to establish a sufficient lipid layer (step 112).

In this manner, in one embodiment, the ability to effectively and more efficiently raise the temperature at the meibomian glands may prove instrumental in melting, loosening, or softening obstructions or occlusions in the meibomian gland to reach the loosening or melting point of the obstruction or occlusion.

As used herein, the terms "melt," "loosen," and "soften" and variants thereof are to be interpreted broadly. These terms broadly encompass any change in form or state of the obstructive or occluding material causing or contributing to an obstruction or occlusion related to a disorder of the eye or eyelid structure to a form such that the obstruction or occlusion can be more easily freed or expressed. This includes, but is not limited to, changing form from less of a solid form or state to more of a liquefied form or state, including but not limited to dissolving, loosening, liquefying, and/or softening of the obstructive or occluding material to be removed, and/or dissolving, loosening, liquefying, or softening of material that holds together particulate matters causing or contributing towards the obstruction or occlusion related to a disorder of the eye or eyelid structure and other modalities.

The application of RF energy may be regulated, meaning that a RF control means or element is controlled to be within the temperatures and means that are safe for the inner surface of the eyelid and at a sufficient temperature for melting, loosening, or softening an occlusion or obstruction in the meibomian gland. The RF energy is maintained for a period of time sufficient to melt, loosen, or soften the occlusions or obstructions. Either during the RF energy application or after the application of RF energy is stopped, the occlusions or obstructions in the meibomian glands are expressed to remove obstructions or occlusions thus providing an improved pathway to restore or improve sebum flow from the gland.

In one embodiment, increasing the temperature of the surface of the palpebral conjunctiva to at least 37 degrees Celsius can begin to provide therapeutic effect for milder cases of MGD. A therapeutic temperature can be any temperature above body temperature. One preferred range for treatment is 43 to 45 degrees Celsius, with a target of 43 to 44.5 degrees Celsius. A time range to direct RF energy may be a period between 1-10 minutes, and may be limited to a range of 3-6 minutes. Temperature in this range has been found effective and comfortable to the patient when treating MGD.

In one embodiment, the application of RF energy may be regulated. Regulated RF energy can include controlling RF energy according to a temperature profile. The temperature profile may be a constant temperature, include ramp-ups, ramp-downs, peaks and valleys. Further, the temperature profile may include RF energy pulses or be modulated with various characteristics, including the use of on/off switching or pulse width modulation (PWM) techniques for example. The use of modulated RF energy may allow the temperature to be raised even higher at the eyelid without damages to the patient's eyelid since the increased temperatures are applied for shorter periods of time. Obstructions or occlusions in the meibomian glands may have melting, loosening, or softening points that are beyond temperatures that may be applied without the use of modulated heat. The temperature needed to melt, loosen, or soften obstructions or occlusions may depend on how keratinized the obstruction or occlusion is. Not all obstructions or occlusions have the same melting, loosening, or softening points.

By example only, elevated temperatures between 45 and 55 degrees Celsius may be possible when directing regulated RF energy, especially if the eyelid has been anesthetized. However, RF energy must always be applied to the eyelid at temperatures that take into consideration the pain response of the patient as well as whether damage will occur to the patient's eyelid and/or surrounding tissues. Depending on the severity of the patient's MGD or the patient's pain tolerance, elevated temperatures may be used with patient's on an individualized basis when directing RF energy. It has been found that lighter skinned patients can generally tolerate less high temperatures than darker skinned patients, and darker skinned patients tend to exhibit less inflammation as a result of exposure to the higher temperatures. Other factors, including humidity, may contribute to a patient's tolerate to greater temperatures. For example, humans can generally tolerate temperatures up to 70 to 80 degrees Celsius in dry saunas where humidity is low. Application of RF energy in higher humidity environments may cause pain and/or burns to occur at lower temperatures.

Severe cases of MGD that cause substantial irritation or risk to the patient may even call for temperatures that would produce category one or two burns to the patient's eyelid, since these burns generally heal. Temperatures that cause category three burns should be avoided. In summary, treatment times and/or temperature can be adjusted to account for these differences. The embodiments described herein are not limited to any particular temperature or time ranges as long as therapeutic temperature is being applied.

The regulated RF energy can be maintained at a therapeutic temperature for a treatment period. The treatment period can be approximately 1 to 10 minutes for example. The RF energy could also be repeatedly applied and maintained for a desired period of time to keep the occlusion or obstruction in a melted, loosened, or softened state. Either during or after such treatment by regulated RF energy, mechanical expression of lipids and other fluids from the meibomian glands has been found to clear obstructions which have essentially melted or been placed in a suspension state (by virtue of melting materials binding solids together).

Optionally, after expression of the occlusions or obstructions is performed (step 112), an optional pharmacological agent may be applied to the meibomian gland to promote the free flow of sebum and/or reduce or prevent inflammation or infections of the eye or eyelids (step 114). Many pharmacological agents have been proposed for treatment of dry eye syndrome, any of which may be effective or more effective upon clearing of obstructions within the meibomian glands. Some of the pharmacological agents that may be utilized include, but are not limited to: antibiotics such as topical or oral tetracycline and chemically modified tetracycline, testosterone, topical or oral corticosteroids, topical androgens or androgen analogues, omega 3 fatty acid compounds such as fish oils, Laennec, enzymes that promote lipid production, agents that stimulate production of enzymes that promote lipid production, and/or any agent which acts as a secretagogue to enhance meibomian gland secretion or secretion of other tear components. For example, androgen and androgen analogues and TGF-beta have been reported to act as a secretagogue to enhance meibomian gland secretion. These compounds are illustrative examples of appropriate pharmacological agents, but those skilled in the art will appreciate that other pharmacological compounds may be utilized.

Also, agents, such as Restasis (cyclosporine A), that replace or promote production of the tear component may also be applied more effectively after treating the meibomian glands according to the embodiments disclosed herein. Treating the meibomian glands improves the lipid layer, thus reducing evaporation and conserving the aqueous layer. Conservation of the aqueous layer reduces the need for tear substitutes to be applied through tear component agents. Thus, tear component agents may not have to be used as often when employing the embodiments disclosed herein to treat a patient's MGD.

In the course of experimenting with the application of RF energy to the inside of the eyelid, it was also discovered that convective heat losses occur due to blood flow in the blood vessels located inside the eyelid. Blood flow through blood vessels located inside the eyelid produces convective heat losses. The blood flow serves as a natural "heat sink" provided by the body. Convective heat loss is lessened when directing RF energy to the inside of the eyelid than when applying heat to the outside of the eyelid. This is because fewer blood vessels are located between the meibomian glands and the inside of the eyelid than the outside of the eyelid. The meibomian glands are located closer to the inside of the eyelid. However, convective heat loss still occurs when heating the inside of the eyelid. However, if the blood flow were reduced, convective heat losses could be minimized allowing for temperatures to be attained and sustained at the meibomian glands in an even more efficient manner and in less time.

Figure 19:
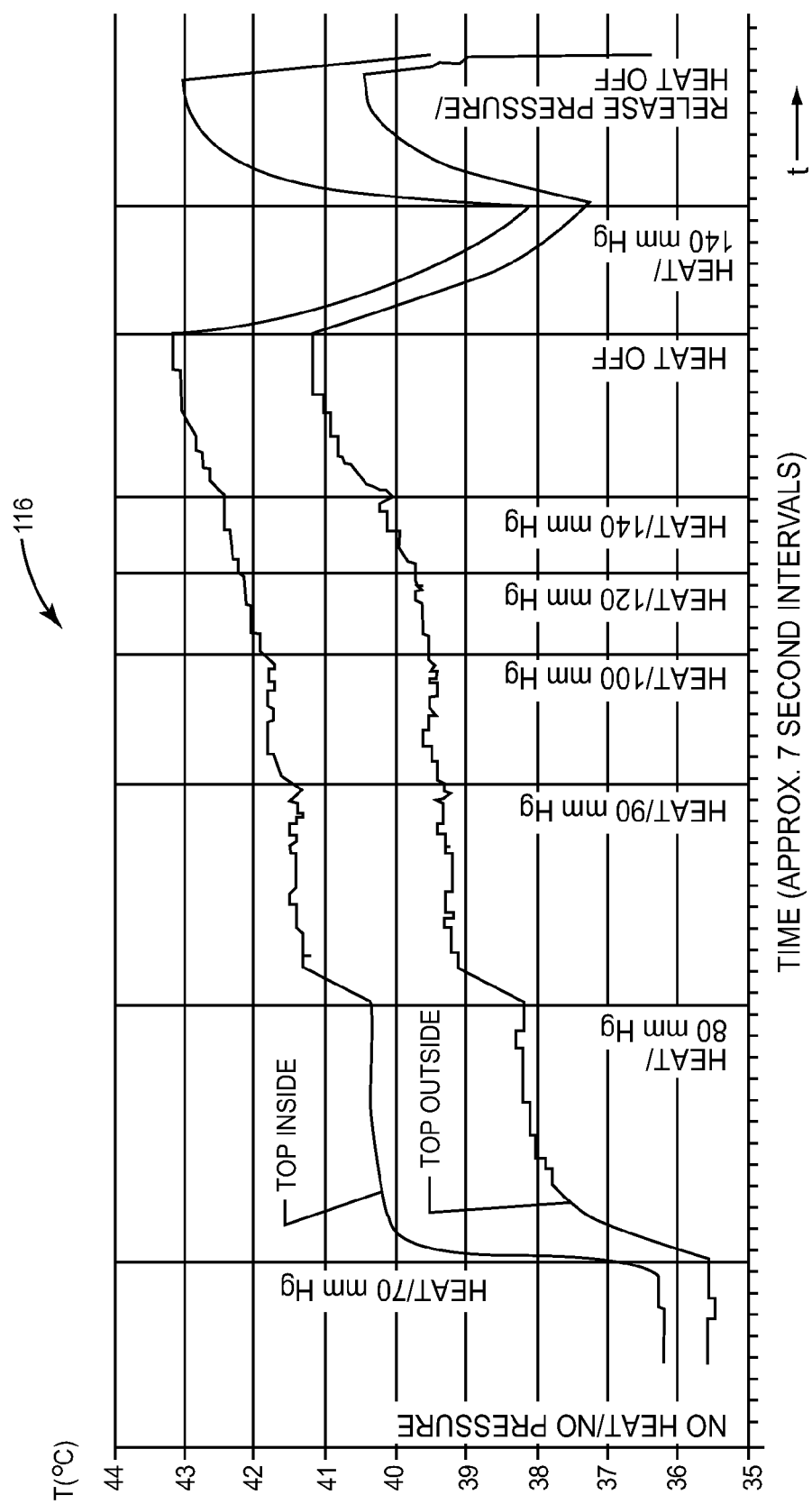
FIG. 19 illustrates an exemplary lid temperature profile of eyelid temperature versus time when heat and force is applied to inside the eyelid.

In this regard, an exemplary lid temperature profile 116 when RF energy is applied to the inside of the eyelid and force at various pressure levels is applied to the outside of the eyelid is illustrated in FIG. 19. There, a graph depicts the temperature at the inner and outer surface of an eyelid as a function of time when a source of constant heat and pressure is applied to an example subject patient. Initially, no heat or pressure is applied to the eyelid. In this example, the temperature at the inside of the eyelid is approximately 36 degrees Celsius while the temperature at the outside of the eyelid is approximately 35 degrees Celsius. When the RF energy source is turned on to direct RF energy to the inside of the eyelid and a 70 mm Hg pressure is applied to the outside of the eyelid, the temperature at the inside of the eyelid dramatically increases quickly. The pressure being applied to the eyelid is reducing blood flow in the eyelid, which reduces convective heat loss and increases conductive heat gain. The temperature at the outside of the eyelid increases quickly as well, but less dramatically than at the inside of the eyelid since the RF electrode is at the inside of the eyelid. A nominal temperature of approximately 40.5 and 38.3 degrees Celsius is reached at the inside and outside of the eyelid, respectively.

If the pressure is increased, even higher temperatures are attained as illustrated in FIG. 19. Finally, when the RF energy source is completely shut off, the temperature degrades. However, the temperature at the eyelid does not degrade immediately due to the force continuing to be applied. Again, the force reduces blood flow to prevent convective heat loss. If both the RF energy source and the force are shut off after being applied, the temperature at the eyelid does degrade more rapidly. This is because blood flow in the eyelid is unobstructed, allowing the body's blow flow to quickly convect the heat away. Thus, the lid temperature profile 116 of FIG. 19 illustrates temperature at the eyelid can be increased effectively and quickly with the application of force in addition to the application of the RF energy Note that the application of force to reduce convective heat loss can be applied whether RF energy is applied via an RF electrode on the inside or outside of the eyelid. As illustrated in FIG. 19, the application of force is effective in both scenarios.

Thus, in one embodiment, the application of force to the patient's eyelid in addition to RF energy is used. The application of force can further assist in obtaining higher temperatures more efficiently inside the eyelid at the palpebral conjunctiva and at the meibomian gland in a shorter period of time and thus more efficiently. This is because the application of force may reduce blood flow to the eyelid to reduce convective heat loss, as discussed above.

Figure 20:
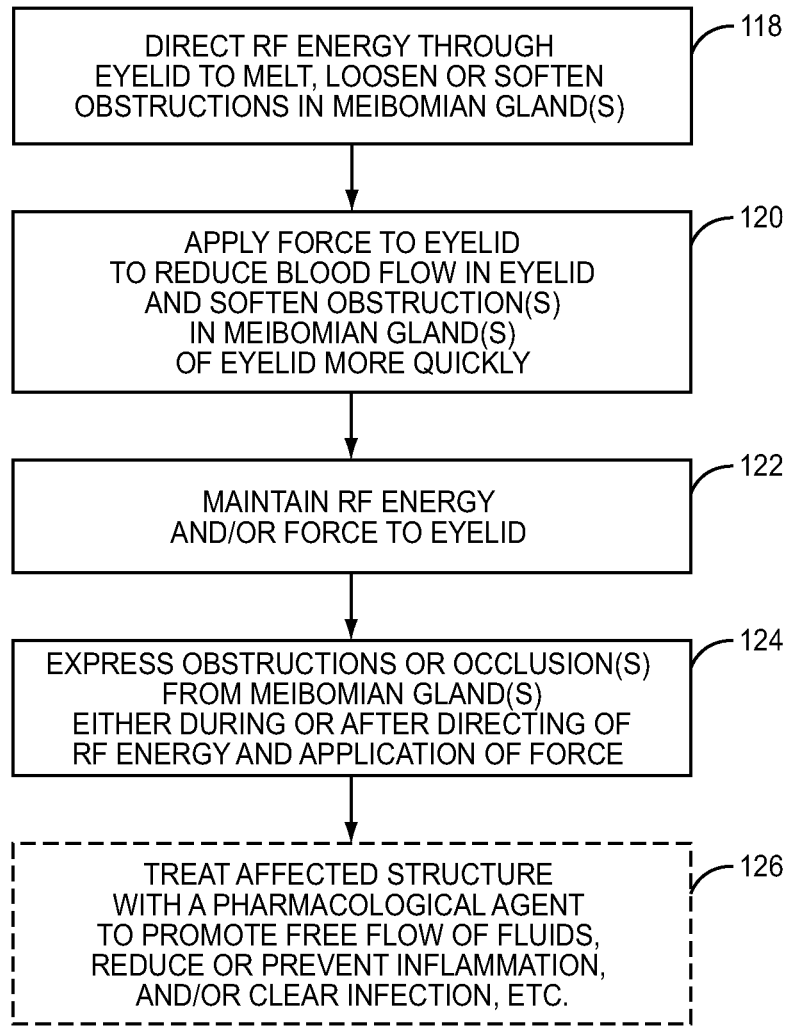
FIG. 20 is a flowchart illustrating an exemplary process of applying heat to the inner eyelid with the addition of force applied to the outside or outer surface of the eyelid relating to treating the meibomian glands.

In this regard, an embodiment to direct RF energy and apply force to the eyelid to treat MGD is illustrated in the flowchart of FIG. 20. First, RF energy is applied to the eyelid to raise the temperature at the meibomian glands to the desired level (step 118). For example, RF energy may be applied to raise the temperature at the inside of the eyelid to 44-47 degrees Celsius. The RF energy may be applied to the inside or outside of the eyelid, or on both sides of the eyelid. The RF energy may also be regulated, meaning that a RF control means or element is controlled to be within the temperatures and means that are safe for the eyelid and at a sufficient temperature for melting, loosening, or softening an occlusion or obstruction in the meibomian gland. A force is also applied to the eyelid to reduce blood flow in the eyelid to allow the applied RF energy to more quickly raise the temperature at the meibomian glands (step 120). The force may be applied to the inside or outside of the eyelid.

The RF energy and/or force may be maintained for a period of time sufficient to raise the temperature at the meibomian glands sufficient to melt, loosen, or soften the obstructions or occlusions (step 122). The force may be maintained after the application of RF energy is stopped, or vice versa depending on the treatment technique desired. Maintaining force after RF energy is removed may cause the temperature at the meibomian glands to dissipate more slowly than if force is removed. Maintaining RF energy without maintaining force may be employed to allow blood flow in the eyelids, such as between successive treatments. For example, it may be desirable to maintain the RF energy to lessen the total amount of treatment time while applying and removing force between treatments. Also, it may not be necessary to apply significant amounts of force or for the same duration as RF energy if the obstruction or occlusion is located in close proximity to the lid margin rather than in the deeper portions of the meibomian gland.

Applying force can also result in a more efficient conductive heat transfer from an applied RF electrode, because the pressure created by the force causes the RF electrode to be compressed against the tissue of the eyelid. This compression can have several benefits. Compression spreads out the tissue to which RF energy is applied thus making it thinner and improving conductive heat transfer. Compression can also "squeeze out" air pockets at the surface of the eyelid due to the microscopic roughness of skin. Thus, compression of the RF electrode against the eyelid increases the surface contact between the RF electrode and the surface of the eyelid (which increases the heat transfer equation) to provide a more effective conductive heat transfer to the meibomian glands. This results in the meibomian glands being heated to the desired temperature level in a shorter period of time due to these gained efficiencies. Further, increased temperatures may be attained that may not have otherwise been obtained, or obtained using less heat or thermal energy. Because the RF electrode is located in close proximity to the eyelid surface and is further compressed against the eyelid surface, heat transfer is very efficient providing for the temperature at the surface of the eyelid to be very close to the temperature at the meibomian glands.

Further, note that while the exact reduction in times to heat the meibomian glands will vary from patient to patient when force is applied, and may be based on the amount of pressure applied to the patient's eyelid, in general, the change in heating times can vary by as much as several hundred percent, for example, when compared to previous methods. As an example, this can translate into five (5) or more minutes that one has to expel an obstruction or occlusion before such re-solidifies when compared with prior methods.

The force may be regulated, meaning that a force generating means is controlled to be within the pressure ranges that are safe to be applied to the eyelid and at sufficient pressure to allow the temperature at the meibomian gland to be raised sufficiently. The force can also be a constant force and be provided manually. For example, force may be provided by a technician or doctor's finger or thumb as RF energy is applied. The force may be applied during the application of RF energy, after the application of RF energy, or both during and after the application of RF energy. In either case, the force may assist in expressing occlusions or obstructions when in a loosened, softened, or melted state from the meibomian glands. The force may include vibratory type forces, including those generated mechanically or those using fluid type devices or mechanisms. The force can be applied at a particular location or vector of the patient's eyelid to be specifically directed to the meibomian glands. This may reduce the level of force needed to express obstructions or occlusions in the glands. The level of force needed to express obstructions or occlusions in the glands may also be greatly reduced when RF energy is selectively applied to the obstructions or occlusions to place them in a melted, softened, or loosened state.

The application of force can also stimulate the movement of fluids or suspensions of occlusions or obstructions from the glands. Embodiments disclosed herein can be used with devices which generally apply a regulated force or milking action to the eyelid to express the fluids or suspensions or to otherwise mechanically stimulate the movement of fluids from the glands. In some instances, a small, gentle, continuous force applied to the eyelid will assist in expression of the fluids and suspensions. Vibration can also be used when applying force simultaneously or immediately after the heating to further assist in the expression.

Thereafter, either during the application of RF energy and/or the application of force or after either, obstructions or occlusions in the meibomian glands may be expressed so that sebum flow is restored from the glands to establish a sufficient lipid layer (step 124).

Just as discussed above in the flowchart of FIG. 18 where only RF energy is applied, the application of RF energy may be regulated. Regulated RF energy can include controlling the application of RF energy according to a temperature profile. The temperature profile may be a constant temperature, include ramp-ups, ramp-downs, peaks and valleys. Further, the temperature profile may include RF energy pulses or be modulated with various characteristics, including the use of on/off switching or pulse width modulation (PWM) techniques for example. The use of modulated RF energy may allow the temperature to be raised even higher at the eyelid without damages to the patient's eyelid since the increased temperatures are applied for shorter periods of time. Obstructions or occlusions in the meibomian glands may have melting, loosening, or softening points that are beyond temperatures that may be applied without the use of modulated heat. The temperature needed to melt, loosen, or soften obstructions or occlusions may depend on how keratinized the obstruction or occlusion is. Not all obstructions or occlusions have the same melting, loosening, or softening points.

By example only, elevated temperatures between 45 and 55 degrees Celsius may be possible when directing regulated RF energy, especially if the eyelid has been anesthetized. However, RF energy must always be applied to the eyelid at temperatures that take into consideration the pain response of the patient as well as whether damage will occur to the patient's eyelid and/or surrounding tissues. Depending on the severity of the patient's MGD or the patient's pain tolerance, elevated temperatures may be used with patient's on an individualized basis when directing RF energy. It has been found that lighter skinned patients can generally tolerate lower temperatures than darker skinned patients, and darker skinned patients tend to exhibit less inflammation as a result of exposure to the RF energy. Other factors, including humidity, may contribute to a patient's tolerance of greater temperatures. For example, humans can generally tolerate temperatures up to 70 to 80 degrees Celsius in dry saunas where humidity is low. Application of heat in higher humidity environments may cause pain and/or burns to occur at lower temperatures.

Severe cases of MGD that cause substantial irritation or risk to the patient may even call for temperatures that would produce category one or two burns to the patient's eyelid, since these burns generally heal. Temperatures that cause category three burns should be avoided. In summary, treatment times and/or temperature can be adjusted to account for these differences. The embodiments described herein are not limited to any particular temperature or time ranges as long as therapeutic temperature is being applied.

The regulated RF energy can be maintained at a therapeutic temperature for a treatment period. The treatment period can be approximately 1 to 10 minutes for example. The RF energy could also be repeatedly applied and maintained for a desired period of time to keep the occlusion or obstruction in a melted, loosened, or softened state. Either during or after such treatment by regulated RF energy, mechanical expression of lipids and other fluids from the meibomian glands has been found to clear obstructions which have essentially melted or been placed in a suspension state (by virtue of melting materials binding solids together).

Optionally, after expression of the occlusions or obstructions is performed (step 124), an optional pharmacological agent may be applied to the meibomian gland to promote the free flow of sebum and/or reduce or prevent inflammation or infections of the eye or eyelids (step 126). The discussion regarding use of pharmacological agents above for the flowchart in FIG. 18 is equally applicable for this embodiment and thus will not be repeated here. Those compounds are illustrative examples of appropriate pharmacological agents, but those skilled in the art will appreciate that other pharmacological compounds may be utilized.

As shown above, heating an inside surface of an eyelid to melt, soften, or loosen obstructions within a meibomian gland provides some advantages. Thus, in one embodiment, a force can be applied to the outside of the eyelid while RF energy is applied via an RF electrode on the inside of the eyelid to treat MGD. The heating of the inner surface of the upper or lower eyelid can be done by any convenient method. The lids can be heated one at a time or both at once, depending on the time available to remove the occlusions once heated. One device for heating the palpebral conjunctiva is illustrated in FIG. 21.

Figure 21:
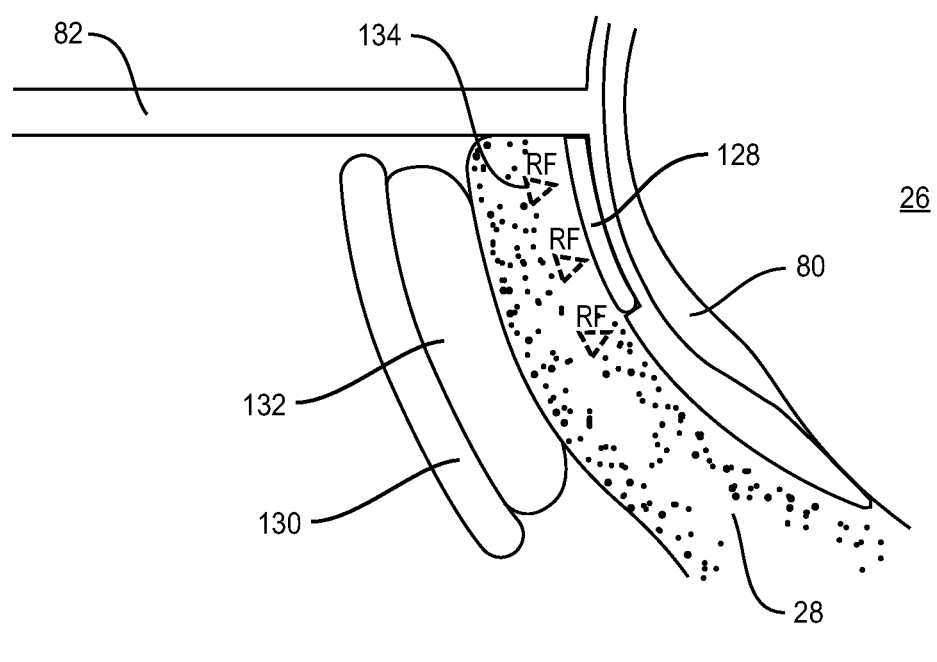
FIG. 21 is a broken side view of an exemplary eyecup comprising an exemplary RF electrode positioned on an inner surface of an eyelid.
Figure 21:

FIG. 21 is a broken side view of an exemplary eyecup 80 comprising an exemplary RF electrode 32 positioned on an outer surface of an eyelid 28. In this manner, FIG. 21 illustrates a system where one RF electrode 32 is placed on an inner surface of the eyelid 28. An eyecup 80 is positioned as described above. An RF electrode 32 is positioned proximate the outer surface of eyelid 28. The eyecup 80 also comprises a support structure 98 and an expression means 100, which may be used as a backplate to apply pressure to express melted or softened obstructions from the meibomian glands.

This embodiment would selectively treat via RF/microwave energy within the tissue by creating a thermal energy at a pre-determined distance from the RF electrode 32. The interior location of the RF electrode 32 in this embodiment puts the energy source closest to the meibomian gland and openings without requiring energy transfer throughout the entire eyelid and tarsal plate. Thereby the energy requirements for therapy and temperature control theoretically would be less.

In addition, the treatment zone could more easily include the entire gland length from the orifice to the gland channel and acini. Thereby the entire duct could be heated and lipid contents expressed as seen in the thermal gradient depicted by the triangles 134 in FIG. 21. The focus of energy would be throughout the entire length of the duct while minimizing thermal treatment of unintended tissues. It is important to note that the thermal gradient in this instance would occur at the interior of the meibomian gland and not from the exterior or orifice of the gland and then throughout the length of the duct.

Figure 22:
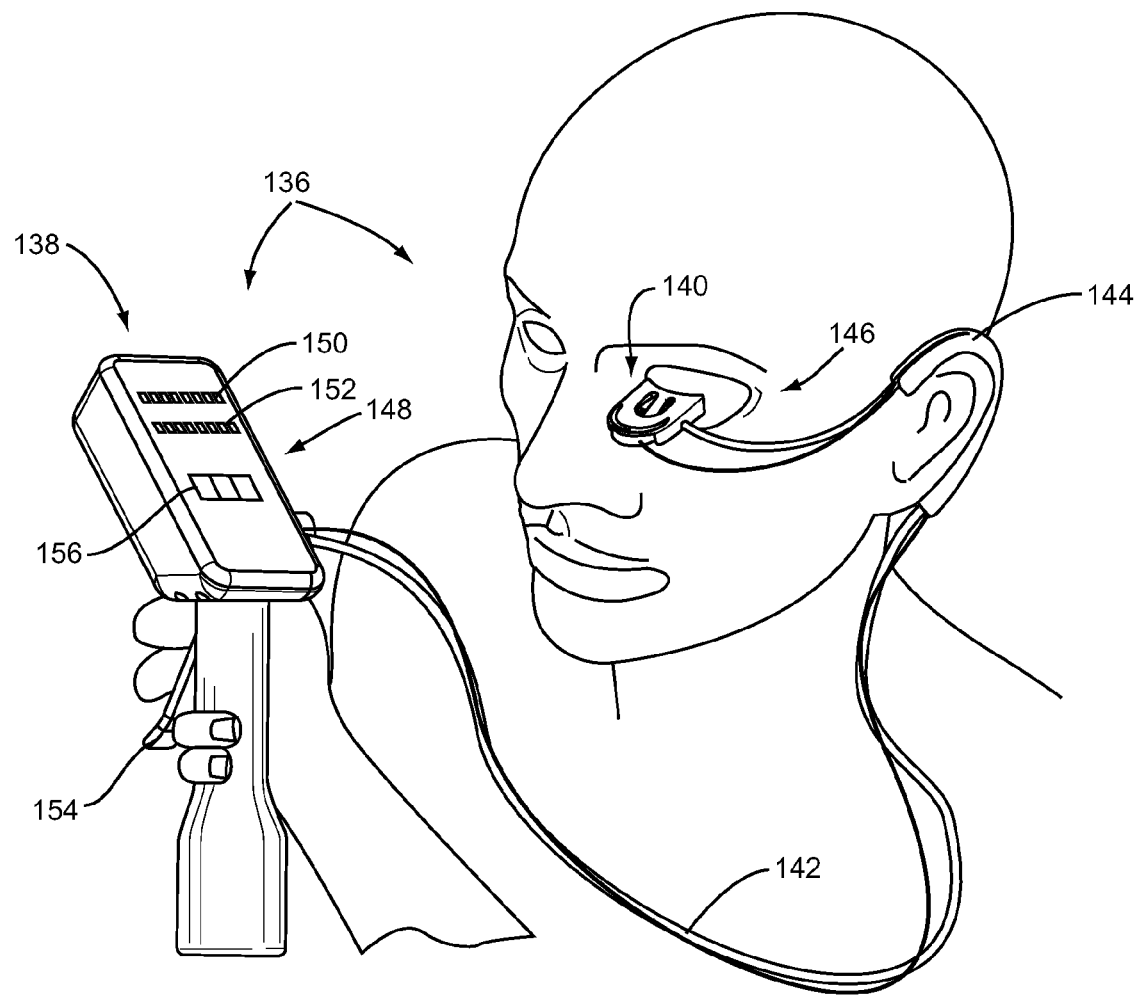
FIG. 22 illustrates a heat and force application device according to one embodiment to facilitate the application of heat to the inside and force to the outside of a patient's eyelid relating to treating meibomian glands.

FIG. 22 illustrates an alternate apparatus for directing RF energy or heat to the meibomian glands. In FIG. 22, the overall device is referred to as a heat and force application device 136. The heat may be applied via convective heat, or via the application of RF energy as disclosed above. In this embodiment, the heat and force application device 136 consists of a hand-held, battery-operated controller 138 that contains heat and pressure generating and regulation components. The controller 138 can also be a non hand-held device that is either mounted or rests on a table top, for example. The controller 138 as described herein is intended to describe and encompass any-device, including but not limited to electronic and pneumatic controls and supporting components, that is adapted to allow and control the application of heat and/or force to the patient's eyelid. The controller 138 is connected to a disposable component 140, via a controller interface 142, to generate heat and force at an eyelid 146, as illustrated in FIG. 22. The disposable component 140 applies heat to the inside of the patent's eyelid and interfaces with an eye cup to apply force to the outside of the patient's eyelid (illustrated in FIGS. 23-26). Both can be used in concert to treat MGD for a single eye. The interface 142 tubing can be wrapped around the patient's ear 144 with any excess clipped to the patient's clothing. The heat and force application device 136 is intended for use by physicians to apply localized heat and pressure therapy for treating MGD.

The controller 138 contains a user interface 148 to allow a physician or other technician to control the heat and force application device 136. Temperature and pressure being applied to the patient's eyelid 146 can be seen on a temperature display 150 and a pressure display 152. By observing temperature and pressure displays 150, 152, the physician can determine when a therapeutic temperature and pressure have been reached. For example, the temperature and pressure displays 150, 152 may be segment bar graphs so that both the temperature and pressure levels and the increasing or decreasing nature of the temperature and pressure levels can be seen. The temperature level to be reached at the patient's eyelid can either be set to a static level within the controller 138, or controllable by a physician or technician. The force and thus the pressure applied to the patient's eyelid is controllable by squeezing a force lever 154. When a physician or technician desires to apply force, the force lever 154 can be squeezed. To release force and thus reduce pressure, the force lever 154 is disengaged. The pressure created by the force applied to the patient's eyelid is displayed on the pressure display 152.

A timer display 156 can be provided on the controller 138 to display the amount of time that heat and/or force has been applied to the patient's eyelid 146. The timer display 156 can display a cumulative amount of time passed or provide a countdown timer if an initial duration is set. For example, the timer display 156 may be comprised of a number of seven segment displays. In one embodiment, the timer display 156 will count down from one hundred eighty (180) seconds and will flash at one hundred twenty (120) seconds and sixty (60) seconds, which is an indicator to the physician to release the force lever 154 and then reapply force and pressure by squeezing the lever 154 again.

Figure 23:
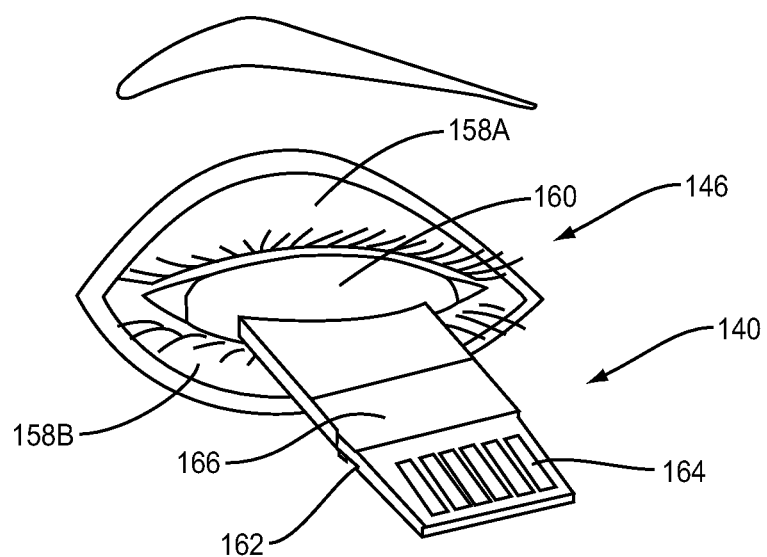
FIG. 23 illustrates the process of placing a lid warmer onto a patient's eye inside the eyelid to install a heat application device onto a patient's eye for treating the meibomian glands, according to one embodiment.

As illustrated in FIG. 23, the disposable element 140 is placed on the patient's eye with the patient's upper and lower eyelids 158A, 158B resting on the outside surface of the lens 160. Before installation, the scleral side of the disposable element 140 may be lubricated with saline, or equivalent lubricating drops. The disposable element 140 is then inserted onto the patient's eye under the eyelids 158A, 158B. A heating element (not shown), which may be an RF electrode in one embodiment, is contained within the disposable element 140 that can direct heat to the inside of the patient's eyelid 146 when installed. In one embodiment, an RF electrode 32 of the type described above may be contained within the disposable element 140 and connected to an RF energy source in order to direct RF energy to the patient's eyelids. The material used to construct the disposable element 140 is not electrically conductive, but is thermally conductive to allow heat from the heating element inside to be transferred to the patient's eyelid. The disposable element 140 can be constructed out of a plastic, including a clear plastic such as LEXAN HPS2 for example. Further, the disposable element 140 can be constructed from a biocompatible material, such as polymethylmethacrylate (PMMA), epoxy, or other materials well known to those skilled in the art. The disposable element 140 may be flexible, but ideally should be only minimally compressible to fit against the patient's eyeball.

The disposable element 140 also contains a lid warmer platform or tab 162. The lid warmer platform 162 may be connected perpendicularly to the disposable element 140 such that it extends away from the patient's eye when installed. The lid warmer platform 162 provides several benefits. First, it provides a handle for insertion and movement or adjustment of the disposable element 140 and its heating element or RF electrode. Second, it provides a guide post for a compression force device to attach to apply a force to the patient's eyelid while the disposable element applies heat or RF energy to the inside of the patient's eyelid. It can also support an electrical interface 164 to allow the disposable element 140 to electrically connect the heating element inside the disposable element 140 to the controller 138 via the interface 142. The controller 138 can then direct electrical or RF energy to the heating element or RF electrode to generate heat to the inside of the patient's eyelid when installed. Second, it provides a support structure for interface circuitry 166. The interface circuitry 166 provides electrical connections for energizing the heating element or RF electrode and communicating temperature measured at the disposable element back to the controller 138 for heat or RF energy regulation. The interface circuitry 166 will discussed later in this application and in regard to FIG. 27.

Figure 24:
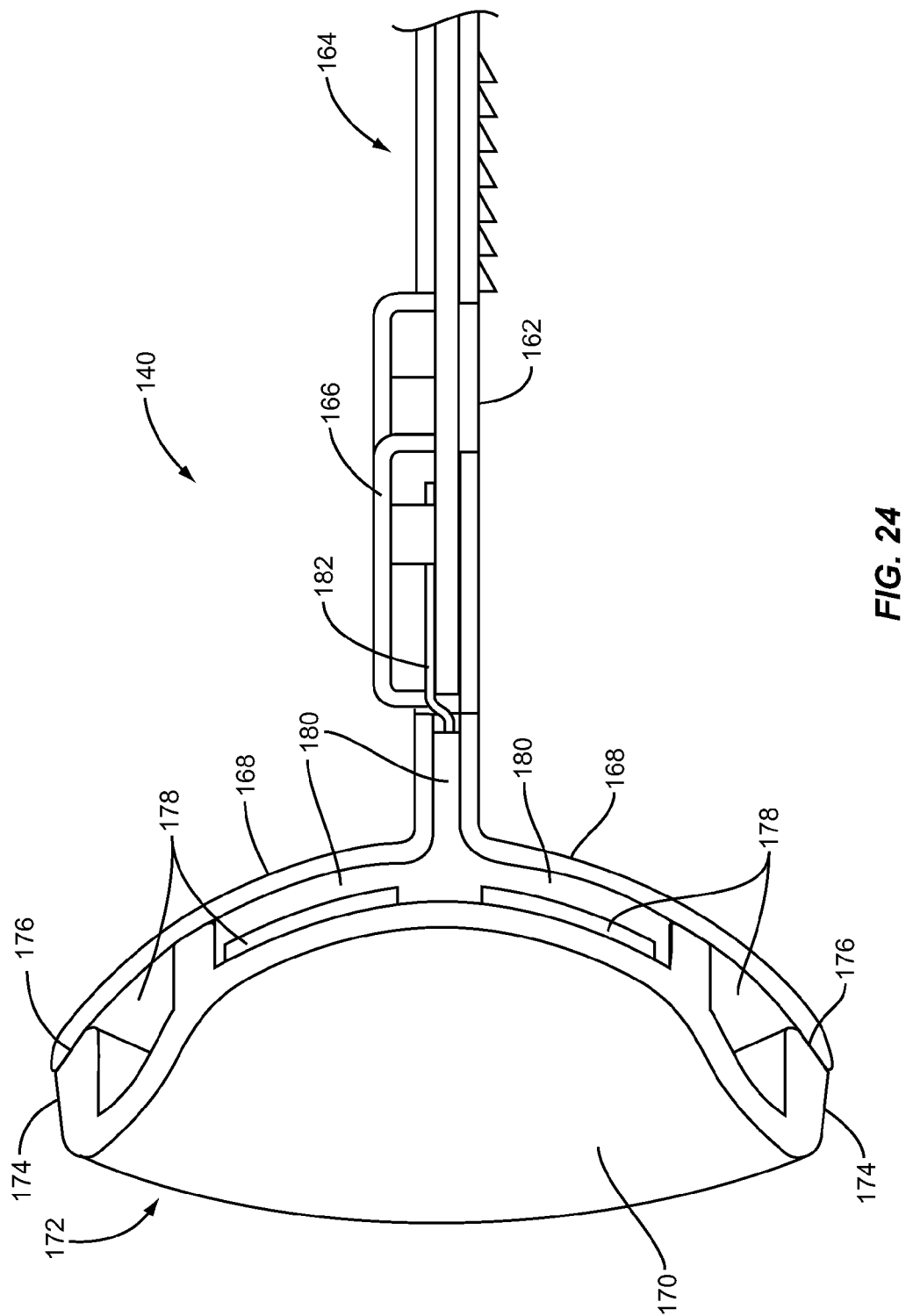
FIG. 24 illustrates a cross-sectional view of the lid warmer illustrated in FIGS. 22 and 23 to further illustrate heat delivery components and features of the lid warmer, according to one embodiment.

FIG. 24 illustrates a cross-sectional view of a lid warmer as part of the disposable element 140 to further illustrate heat or RF energy delivery components and features of the lid warmer, according to one embodiment. An eyelid side 168 is attached to scleral side 170 to form lens 172. The scleral side 170 contains a bend 174 around its circumference edge to provide an attachment edge 176 to support attachment of the eyelid side 168. Because of the bend 174, a hollow chamber 178 is formed. The hollow chamber 178 supports a heating element 180 contained inside the lens 172 to generate heat when energized. In one embodiment, the heating element 180 may be an RF electrode as described herein. In one embodiment, the heating element 180 abuts against the eyelid side 168 so that the heat generated is located adjacent the inner eyelid to apply heat to the meibomian glands. The heating element 180 is attached to the interface circuitry 166 via a fused link 182, which is then attached to the controller 138 via the lid warmer platform 162 being attached to the controller interface 142. In this manner, the controller 138 can cause the heating element 180 to generate heat by applying an electrical signal to the interface circuitry 166 which is connected to the heating element 180. If the temperature exceeds the threshold temperature level of the fused link 182, the link 182 would melt and create an open circuit to disable the heating element 106 for safety reasons. Alternatively, the fused link 182 could be a thermal link provided as an integrated part of the heating element such that the fused link 182 would melt and create an open circuit at a given threshold temperature.

The heating element 180 may be provided in any form or material. In one embodiment, the heating element 180 is an RF electrode of the type described herein. In another embodiment, the heating element 180 may be a resistive type heater, a thick film heater, or any one of a number of other types, such as a "flex circuit" (etched metal on flexible substrate) well known to those skilled in the art. The heating element 180 can be formed to the shape of the disposable element 140. In the illustrated example, the heating element 180 is a material that is both electrically and thermally conductive. This may be important. The electrical conductivity characteristic allows current to be applied to the heating element 180 to generate resistive heat. The thermal conductivity characteristic serves to evenly distribute the resistive heat over the entire heating element 180 to more evenly distribute the heat to the patient's eyelid. Without these characteristics, it may be more difficult to regulate heat generated by the heating element to efficiently and effectively melt, loosen, or soften obstructions or occlusions in the meibomian glands. Examples include the E5101 carbon-loaded polyphenylene sulfide and the E2 liquid crystal polymer, both manufactured by Cool Polymers, Inc.

The size of the disposable element 140 may also play a part in the heating element 180 selection and the amount of heat it must generate to be effective in MGD treatment. The disposable element 140 distributes heat generated by the heating element 180. A larger disposable element 140 may distribute the heat generated by the heating element 180 more uniformly and over a larger surface area. Also note that the application of heat to the patient's eyelid does not necessarily have to include an embedded heating element 180. Heat application may be provided via an RF electrode as described herein. In another embodiment, the heat may be provided as part of the environment, such as air for example. The amount of heat applied, the temperature reached at the meibomian glands as a result, where the heat is applied on the patient's eyelid or surrounding tissue, and the duration of heat applied can control the selection of the heating source.

In addition to the insulation provided by the material used to construct the disposable element 140, the disposable element 140 may also contain an integrated insulator inside the chamber 178 as an additional measure of insulation. Insulation prevents substantial heat from reaching the eyeball and thus protects the cornea and sclera. As employed herein, the term "insulate" or "insulation" is intended to include any component or material and/or specific geometries of components or materials, wherein there is greater resistance to thermal conduction or radiation towards the surface of the eye than towards the eyelid. Stated alternatively, in the insulator thermal energy radiates more easily towards the eyelid 158A, 158B than towards the eyeball surface in order to minimize the possibility of causing injury to the eyeball. In the embodiment of FIG. 24, the integrated insulator is air and is formed by the natural gap that exists by the space left by the heating element 180 not filling up the entire volume of the chamber 178. The heating element 180 is biased according to its location in the disposable element 140, and in particular to be located behind the integrated insulator, to produce more heat on the insides of the patient's eyelid than on their eyeball.

Figure 25A:
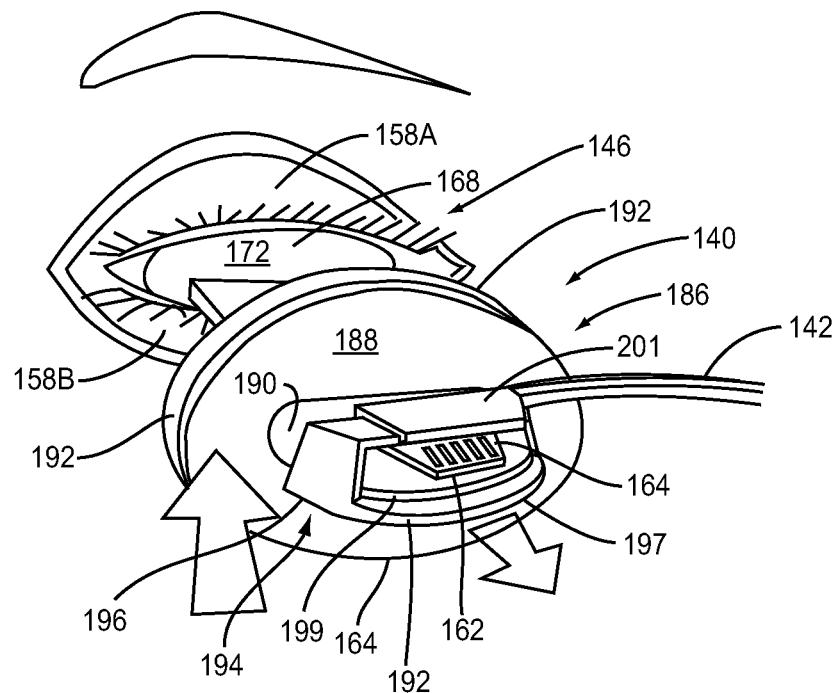
FIGS. 25A and 25B illustrate embodiments of a lid warmer and eyecup heat and force application device for securing the eyecup to the lid warmer as part of installing the force application device onto a patient's eye for treating the meibomian glands.

FIG. 25A illustrates an eyecup 186 that is adapted to allow the controller 138 to apply a force to the patient's eyelids 158A, 158B in addition to heat. The eyecup 186 is a curved carrier 188 having a slot 190 that supports an inflatable bladder 192. The inflatable bladder 192 is attached to the curved carrier 188. The inflatable bladder 192 is then connected to the controller 138 via a tubing 198 in the controller interface 142 (see FIG. 22) such that the controller 138 can pump air into the tubing 198 to inflate the inflatable bladder 192. When inflated, the eyecup 186 applies force to the outside of the eyelid 158A, 158B while heat can be applied via the lens 172 and heating element 180. To apply force to the patient's eyelids 158A, 158B, the bladder 192 is inflated under control of the controller 138. To release the force and thus reduce pressure, the air in the bladder 192 is released by the controller 138.

When desired to be used, the lid warmer platform 162 is inserted into an eyecup orifice or slot 190 in the eyecup 186 between a latching mechanism 194. The latching mechanism 194 provides a means to secure the lid warmer platform 162 to the eyecup 186 when in use as well as provide an interface to electrically connect the lid warmer electrical interface 164 to the controller 138 via the controller interface 142. The latching mechanism 194 is comprised of a carrier 196 having a semi-circular carrier base 197. The carrier base 197 receives an eyecup platform 199 attached to the eyecup 186. The carrier base 197 and eyecup platform 199 can be squeezed together like a clip to control an opening through which the lid warmer platform 162 is inserted into the carrier 196 when inserted into the orifice 190 of the eyecup 186. When the carrier base 197 is not squeezed against the eyecup platform 199, the carrier opening through which the lid warmer platform 162 is inserted closes to secure the lid warmer platform 162 to the carrier 197, and thus the eyecup 186. The eyecup platform 199 is adapted to allow the lid warmer platform 162 to rest on top when inserted into the eyecup orifice 190. When inserted, the electrical interface 164 of the lid warmer contacts a carrier interface 201, which provides an electrical connection between the electrical interface 164 and the controller interface 76.

Figure 25B:
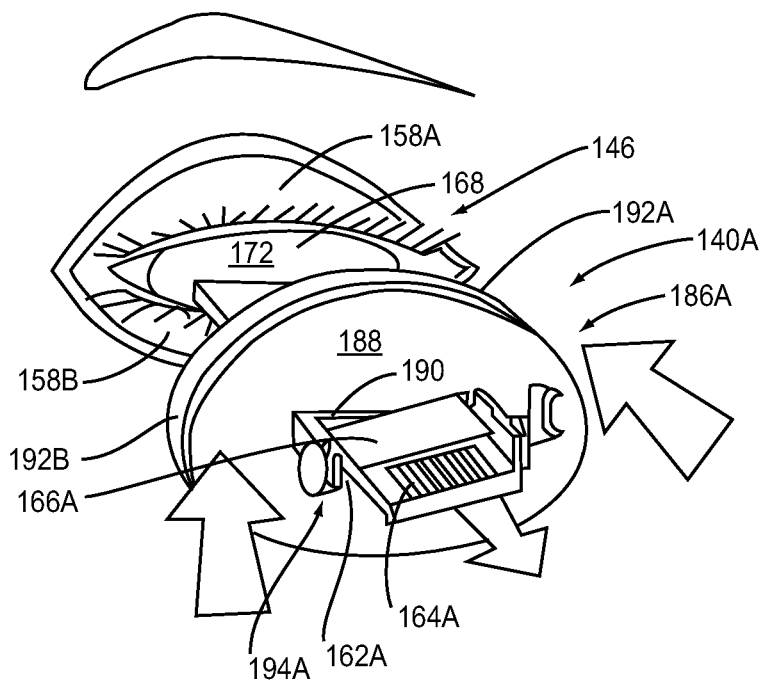

FIG. 25B illustrates an alternative latching mechanism 194A to one illustrated in FIG. 25A. The latching mechanism 194A is compressed in the horizontal plane while the eyecup 186A is moved forward along the lid warmer tab 162A until it rests against the outside of the patient's eyelids 158A, 158B. When the latching mechanism 194A is released, the eyecup 186A is fixed in place in its location along the lid warmer tab 162A. In this manner, the patient's eyelids 158A, 158B are "sandwiched" between the lens 172 and the eyecup 186A.

Figure 26:
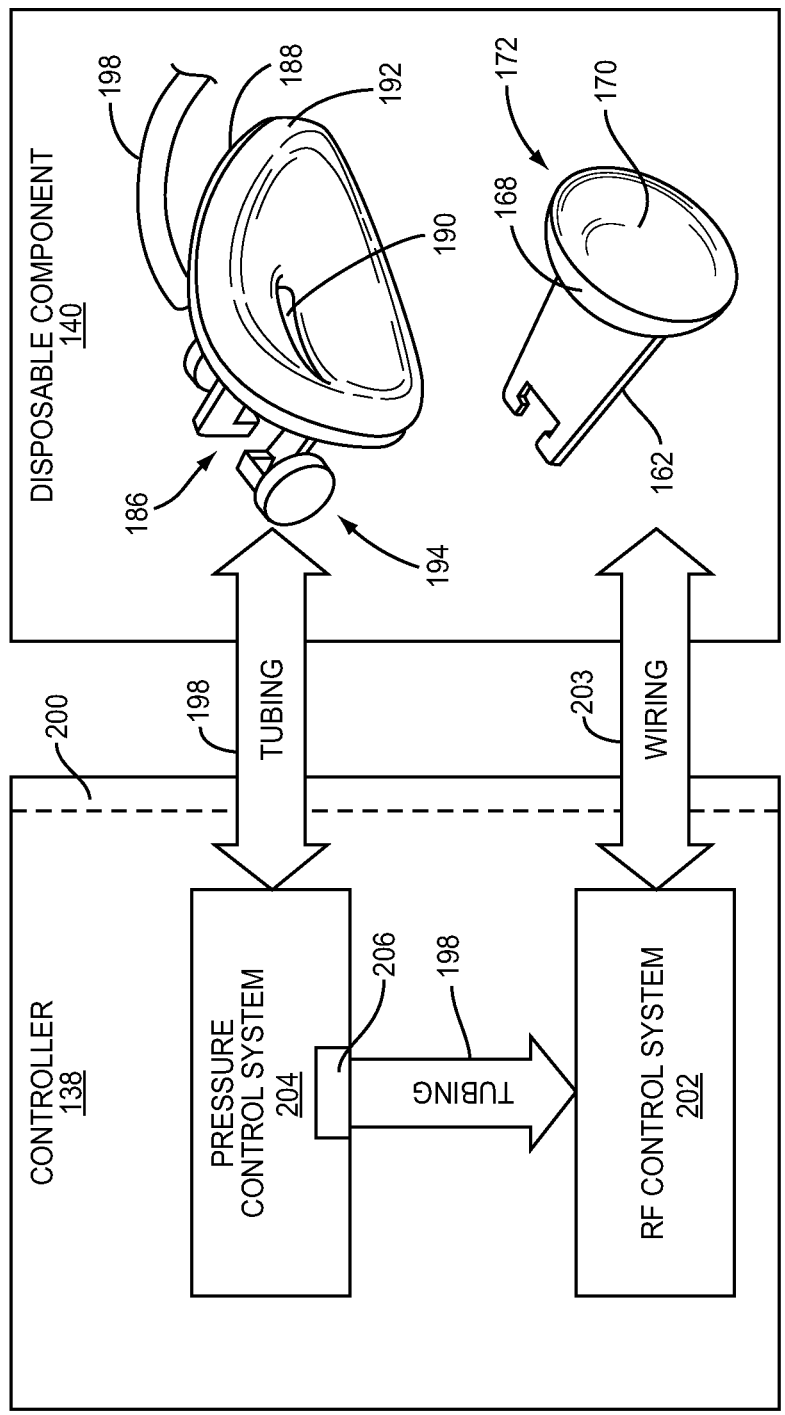
FIG. 26 illustrates a top level system diagram of the temperature and pressure control and communication components of the heat and force application device for selectively and controllably communicating to the lid warmer and eyecup components to apply heat to the inside of a patient's eyelid and/or force to the outside of the patient's eyelid, according to one embodiment.

FIG. 26 illustrates the interface components between the controller 138 and the disposable component 140 and the eyecup 186, at a system level. The controller 138 of the heat and force application device 136 contains a pressure control system 204 and a RF control system 206. The pressure control system 204 is the control component within the controller 138 that controls the pressure from the force applied to the patient's eye via the eyecup 186. The RF control system 202 is the control component within the controller 138 that controls the heat applied to the patient's eye via the lid warmer. The pressure control system 204 also communicates the pressure in the tubing 198 to a pressure sensor 206 within the pressure control system 204. The pressure sensor 206 is used to determine the pressure level in the tubing 198 to display the pressure on the pressure display 152 as well as to provide feedback to the controller 138 to provide the various functions and controls for the system, as will be described in more detail below. The pressure sensor 206 also allows the recordation of pressure data to be recorded by the controller 138, or an external data acquisition device (not shown) coupled to the controller 138, if desired.

FIG. 26 also illustrates more detail regarding the latching mechanism 194 on the eyecup 186. The latching mechanism 194 facilitates providing a connection between the lid warmer 172 and the lid warmer platform 162 and the eyecup 186, and the lid warmer 90 to the electronics wiring 203 when the eyecup orifice 190 is slipped over to the lid warmer platform 162 to secure the eyecup 186 to the patient's eyelid. Two different types of latching mechanism 194, 194A were previously illustrated in FIGS. 25A and 25B, either of which can be used to secure the platform 162 to the eyecup 186, or any other type may be used.

Figure 27:
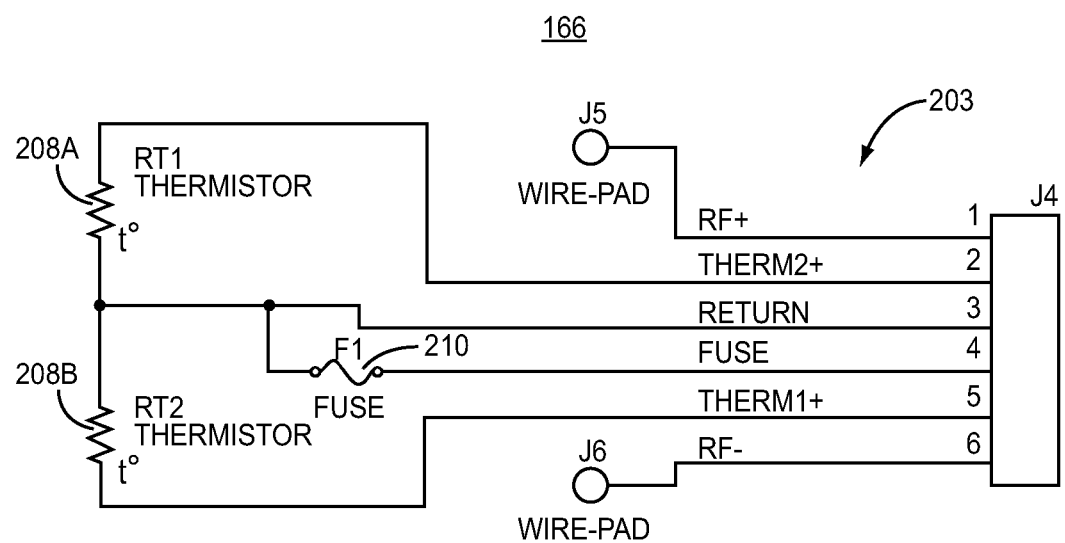
FIG. 27 illustrates an interface circuit diagram for the heating and force application device, according to one embodiment.

FIG. 27 illustrates the specific wiring and supporting circuitry that comprises the electronics wiring 203 to interface the controller 138, and particularly the RF control system 202, to the lid warmer to apply heat to the patient's eye for the disclosed embodiment. Six wires make up the electronics wiring 203. The six interface wires are connected to the interface circuitry 166 that is embedded in the disposable component 140. In one embodiment, the heating element 180 is an RF electrode as described herein for directing RF energy to the meibomian glands in the eyelid. In this embodiment, RF+ and RF− are connected to the heating element 180 (RF electrode) in the lid warmer when the platform 162 is connected to the controller interface 142. THERM1+ and THERM2+ are coupled to two thermistors 208A, 208B. The two thermistors 208A, 208B provide an indication of temperature at the patient's eyelid as part of a temperature feedback mechanism to allow the RF control system 202 to monitor the temperature for control. Because in the preferred embodiment, the temperature drop between the heating element 180 and the inside of the patient's eyelid is minimal, regulating temperature is simpler. This is because the thermistors 208A, 208B record temperatures closer to the actual temperatures at the glands and thus temperature overshooting is minimized. It is important to attempt to minimize temperature overshoot so as to not damage the patient's tissue. Temperature thermostats or other more complicated regulation circuits may be employed to regulate temperature as well if desired, especially if temperature overshooting is an issue. Further, the size of the heating element and power supply could also be selected so that only a known maximum amount of heat could be generated even if the heating element 180 were energized all the time. This would avoid use of a regulation circuit to prevent temperature overshoot.

Two thermistors 208A, 208B are provided for redundancy and error checking in the event one fails. Both thermistors 208A, 208B should provide the same signal indicative of temperature. Both thermistors are coupled to a common RETURN to provide common current return/grounding. Lastly, a FUSE line is provided and linked to a fuse 210, which is also coupled to the RETURN line. The controller 138 can send a current over the FUSE line sufficient to blow fuse 138. The controller 138 can blow the fuse 210 to provide an indication that the lid warmer has been previously used. Thus, if the lid warmer is reused, the controller 138 can detect the open circuit on the FUSE line and know that the fuse 210 has been previously blown.

Figure 28:
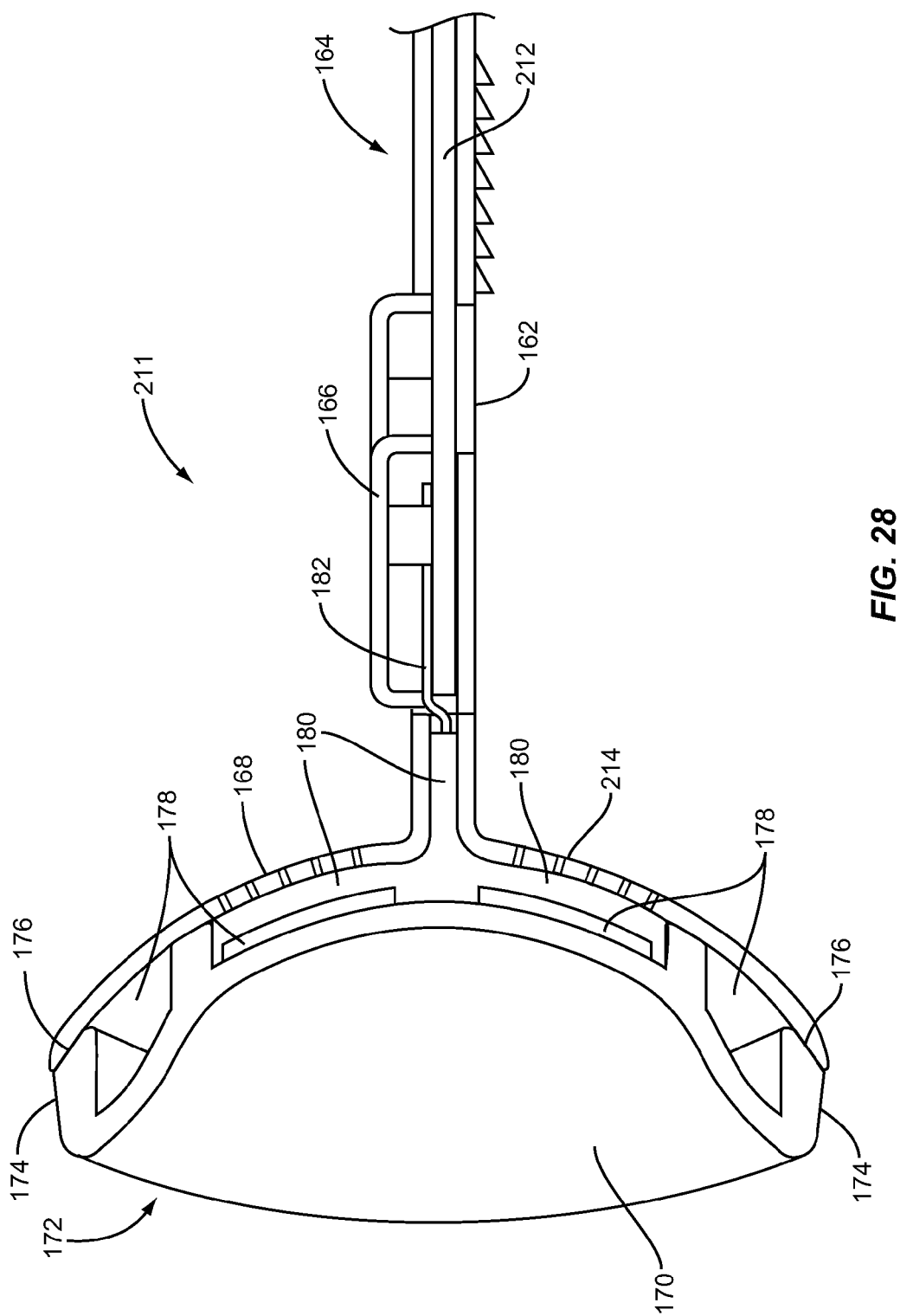
FIG. 28 illustrates a cross-sectional view of an exemplary eyecup comprising an exemplary aspiration channel for collecting materials expressed from the meibomian glands and an exemplary conduit for cooling media.

FIG. 28 illustrates an alternative embodiment of an eyecup 211 that may be employed as part of treating MGD. As illustrated in FIG. 28, an exemplary eye cup 211 provides insulation to the globe of the eye and has localized aspiration at the location of the meibomian glands. An eye cup that maintains a space between the eyelid and cornea has been described previously with reference to FIG. 24. The materials in the eye cup are non-conductive and limit the transference of thermal energy to the globe. An inner sandwich layer of the eye cup limits thermal energy to the globe of the eye. The inner sandwich can be made from Aerogel in one embodiment. The inner sandwich may be a vacuum space. In one embodiment, the inner sandwich is filled with a non-conductive gel.

Figure 29A:
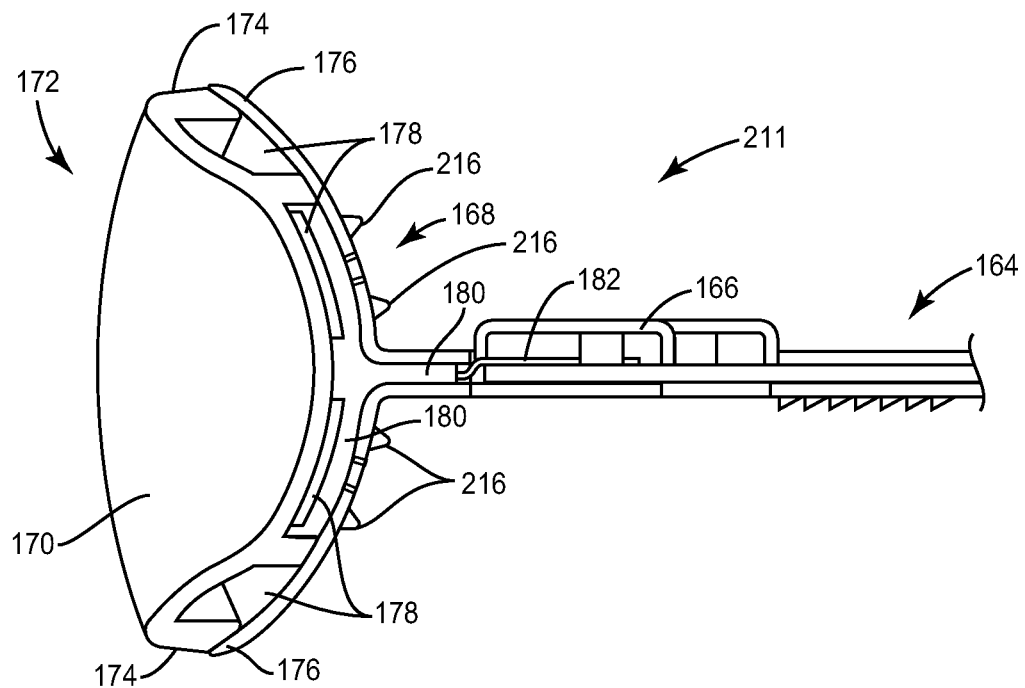
FIG. 29A illustrates an exemplary eyecup comprising exemplary gutter structures configured to assist in aspirating materials expressed from within a duct of the meibomian gland through the orifice of the meibomian gland and to facilitate drugs or other topical agents to an eye.

As described previously, the eyecup 211 is configured to maintain a spacing from the cornea. In one embodiment, the eyecup 211 has an aspiration conduit 212 for aspiration means at the meibomian gland location. The aspiration conduit 212 is connected to external aspiration or vacuum source that is used to withdraw material from the glands (as opposed to mechanical pressures directed on the outside of the eyelid), as seen in FIG. 28. The aspiration source pulls vacuum through a mesh screen 214 which is positioned at the meibomian gland openings. Separate gutters or projections 216 focus aspiration forces or vacuum at the meibomian glands as seen in FIG. 29A. The gutters 216 also facilitate drug delivery as described below.

Figure 29B:
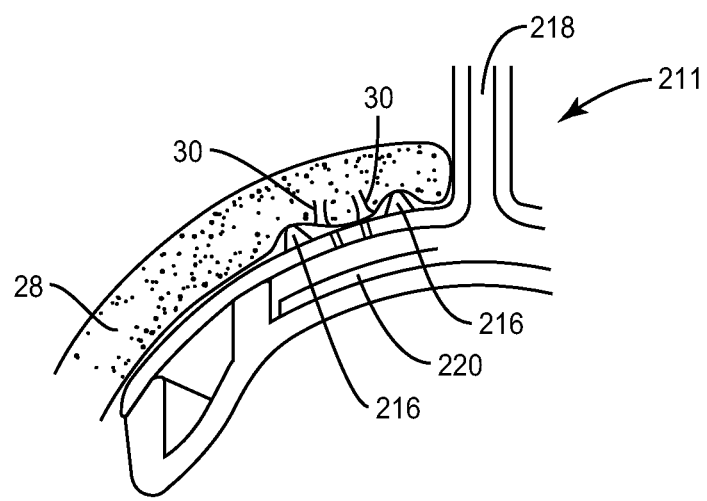
FIG. 29B is a close up view of the exemplary gutter structures of FIG. 29 illustrating how the exemplary gutter structures assist in pulling open the meibomian gland to assist in expressing and collecting materials from within a duct of the meibomian gland through the orifice of the meibomian gland.

The gutters 216 may also be configured to protrude gland openings towards the mesh screen and aspiration forces as seen in FIG. 29B. By applying aspiration forces at the openings of the glands, obstructions at the orifices of the glands can be removed once heated and loosened via aspiration means. The application of localized aspiration reduces blood flow to the treatment area due to mechanical force on the gutters 216, minimizing heat sink issues of the vasculature. The aspiration source may be applied at a low level to help maintain eyelid stability at the beginning of the procedure in one embodiment.

Upon the application of RF/microwave energy and as the gland duct materials begin to melt, the aspiration source may preferentially increase to help draw materials out of the glands. Since melted gland duct materials may be more viscous in nature, the aspiration conduit 212 could also be a mechanism to deliver flush fluid intermittently to help improve the transport of aspirated materials. Thus the aspiration conduit 212 can periodically be used to administer fluids for cleaning the treatment area, or a separate conduit can be built into the eye cup for delivering fluid to the treatment area. In one embodiment, the aspiration may be pulsed in pumping-like fashion to facilitate material removal. The material aspirated will be drawn into a separate collection chamber for removal or analysis. It is the object of the aspiration forces to be gentle and less traumatic to the tissues than mechanical expression forces.

As RF energy is being applied in conjunction with aspiration, the tissues being treated may become dried out which would tend to diminish the capability of the RF energy to heat the nearby tissue. It may be beneficial during the energy delivering steps to periodically stop aspiration to lightly administer saline or other conductive fluids to the treatment area so that a more effective administration of RF energy can continue to be employed. This administration of fluids can be accomplished through the conduit for aspiration.

The aspiration conduit 212 can also be used for the administration of topical agents and therapeutic drugs to the glands post treatment. In one embodiment, a separate conduit from the aspiration conduit 212 could be employed to deliver drugs to topical agents. This administration of agents could be very useful for patient comfort post treatment since the aspiration means coupled with RF energy may have dried out the inner portion of the patients' eye lid in a localized region.

In one embodiment, the gutters 216 on the eyecup 211 provide for a more efficient administration of drug or topical agents.

The eyecup 211 acts as an insulator for the globe and it can also be used to preferentially cool eye lid tissues that are not populated with meibomian glands. In one embodiment, a conduit (either conduit 212 or a separate conduit) supplies coolant media to areas of the eyelid where heating is not desired. The coolant media can be cryogenic materials in one embodiment. The coolant media may also comprise continuously flowing cooled saline. In another embodiment, coolant media can comprise flowing air, which may also be cooled.

In another embodiment, an RF electrode or microwave antenna is placed on both the outer and inner surfaces of the eyelid to direct thermal energy rapidly within the meibomian glands and selectively target gland duct contents. The microwave/RF energy is passed through the outer or inner surfaces of the eyelid or orifices of the meibomian glands to create a thermal energy increase directly at the location of the gland duct contents. Two RF electrodes or microwave antennae configured to provide microwave or RF energy are placed on both the inner and outer eyelid(s) of a patient. Through a direct connection with a RF or microwave generator, or electrical surgical unit (ESU), thermal energy is selectively delivered beneath the outer tissue layer of a patient and to a location within tissue between two the energy delivering RF electrodes or microwave antennae.

Figure 30:
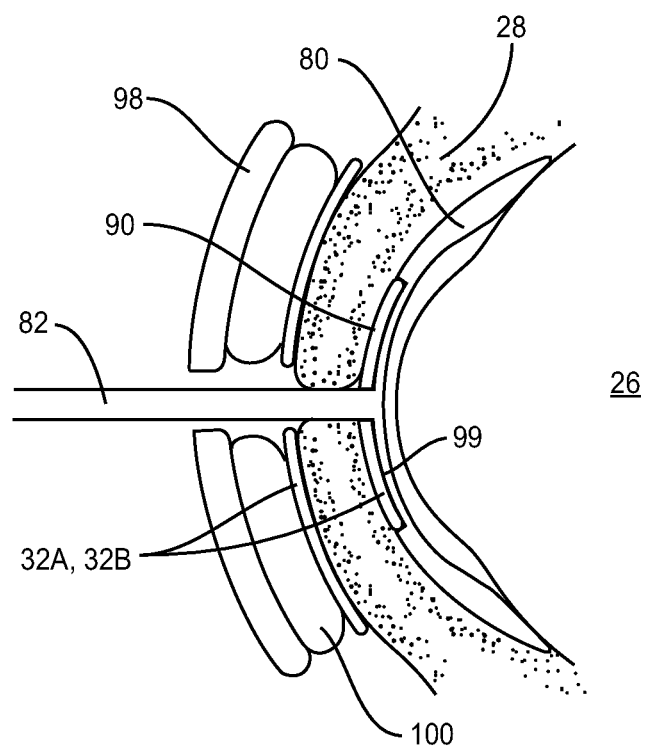
FIG. 30 is a broken side view of an exemplary eyecup comprising exemplary RF electrodes positioned on both an outer surface and an inner surface of an eyelid.

FIG. 30 illustrates an eyecup 80 where two RF electrodes 32A and 32B are used. FIG. 21 is a broken side view of an exemplary eyecup 80 comprising a pair of exemplary RF electrodes 32A, 32B. The eyecup 80 is positioned as described above. One RF electrode 32A is placed on the outer surface of the eyelid and one RF electrode 32B is placed on the inner surface of the eyelid. The eyecup 80 also comprises a support structure 98 and an expression means 100, which may be used as a backplate to apply pressure to express melted or softened obstructions from the meibomian glands. The expression means 100 provides a back plate against which force may be applied. In limited circumstances when the obstruction in the meibomian gland channel is minimal, the meibomian gland may be cleared merely through the application of force externally applied to the eyelid, such as gentle finger press. More specifically, with the expression means 100 in place and the eyecup 80 behind the eyelid, pressure may be applied to the external surface of the eyelid, the eyelid being "sandwiched" between the expression means 100 and the eyecup 80.

In other instances, the meibomian gland obstruction may be blocked to a degree greater than can be treated with simple pressure alone. In such cases it is necessary to apply thermal energy to the eyelid in order to loosen, break up, fracture, soften or liquefy at least a portion of the occlusion. Thermal energy may be applied by any one of the well known means for applying thermal energy such as modalities such as resistive, IR (infrared), ultrasonic heating, microwave, any one of the numerous "hot pads" that chemically produce an exothermic reaction or in the simplest form a hot compress. Experimentation has revealed that in order to be clinically effective the eyelid should be heated to a temperature of between about 35 degrees Celsius and 47 degrees Celsius. The length of time for which thermal energy (i.e. heat) is applied to the eyelid depends upon the extent that the obstruction blocks the meibomian gland channel as well as the composition of the obstruction. In very minor cases, heat may be applied to the eyelid for less than three minutes or even as little as five to fifteen seconds. On the other hand, extreme blockage may require as much as thirty minutes of heating to melt, loosen, or soften the obstruction prior to the application of force to the eyelid to express the softened obstruction. Experimentation has further revealed that the eyelids are efficient heat exchangers with circulating blood acting as the cooling mechanism and that the eyelid temperature returns to normal in less than two minutes at which time the obstruction re-hardens making extraction difficult. It is therefore necessary to apply the aforesaid expressive force to the eyelid within that time frame in order for the treatment to be successful. Thus, pressure, preferably in a milking type action, to urge the obstruction upward and out of the meibomian gland orifice should be employed. Again, depending on the nature and location of the obstruction, mere compressive force may be effective in some instances.

In FIG. 30, the desired amount of thermal energy to deliver to contents within the meibomian glands is an amount sufficient to heat the contents to between 37 and 45 degrees C. The RF energy or microwave energy can be controlled by a controller, such as controller 68 in FIG. 11, or by the RF generator 64 in FIG. 10, to selectively heat the contents of the ducts and channel of the meibomian glands to a known temperature within the tissues and/or to selectively heat lipid containing materials. This may be done by adjusting the power and duration of the applied RF energy, or by changing the waveform shape (stepped or curved). The waveforms may be pulsed or continuous waveforms. In another embodiment, the shape of the RF electrode or microwave antenna that delivers or emits the RF or microwave energy may be changed to selectively heat the contents of the ducts and channel of the meibomian glands to a known temperature within the tissues and/or to selectively heat lipid containing materials. In this manner, the RF energy will be applied to selectively target any obstructions within the duct, channel, or acini of the meibomian glands to melt, soften, or loosen such obstructions. Once melted, softened, or loosened, the obstructions may be more easily expressed from within the channel of the meibomian gland through an orifice of the meibomian gland.

In the two electrode system shown in FIG. 30, the RF or microwave energy can also be controlled by the fixed distance between the two RF electrodes 32A, 32B. Since this distance is fixed, the RF energy source pinpoints the wave forms within a desired depth of the eyelid and away from the surface layer or outermost tissue layer.

In another embodiment, the system at the inner eyelid could contain fluid sensors which react to the presence of fluid being expressed by the gland. As a control feedback mechanism, the energy application can be reduced as expressed material is sensed or collected. As part of the feedback mechanism, additional pulses of energy could be reduced in power or stopped when no additional fluid is collected thereby terminating the procedure.

Regardless of whether an RF electrode is placed on an outer surface of the eyelid, an RF electrode is placed on the inner surface of the eyelid, or an RF electrode is placed on both an outer surface and an inner surface of the eyelid, the RF energy may be applied to selectively target obstructions within ducts, channels, or acini of meibomian glands in order to melt, soften, or loosen the obstructions. Once melted, softened, or loosened, the obstructions need to be expressed from within the channel of the meibomian gland through an orifice of the meibomian gland.

Various mechanics of expressing the heated contents of the meibomian gland have been described previously with the use of an eyecup and inflation bladders, such as described in U.S. application Ser. No. 11/434,033 entitled "Method and Apparatus for Treating Gland Dysfunction Employing Heated Medium," filed on May 15, 2006, which claims priority to U.S. Provisional Patent Application No. 60/700,233, filed Jul. 18, 2005, entitled "Method and Apparatus for Treating Gland Dysfunction"; U.S. application Ser. No. 11/434,446 entitled "Method and Apparatus for Treating Gland Dysfunction," filed on May 15, 2006, U.S. application Ser. No. 11/434,054 entitled "Method and Apparatus for Treating Meibomian Gland Dysfunction," filed on May 15, 2006; U.S. application Ser. No. 11/541,291 entitled "Method and Apparatus for Treating Meibomian Gland Dysfunction Employing Fluid Jet," filed on Sep. 29, 2006; U.S. application Ser. No. 11/541,418 entitled "Treatment of Meibomian Glands," filed on Sep. 29, 2006; and U.S. application Ser. No. 11/541,308 entitled "Melting Meibomian Gland Obstructions," filed on Sep. 29, 2006; and U.S. application Ser. No. 12/015,558, filed Jan. 17, 2008, entitled "Inner Eyelid Treatment for Treating Meibomian Gland Dysfunction," all of which are incorporated herein by reference in their entireties.

Other mechanisms for expressing melted, softened, or loosened, obstructions from within the channel of the meibomian gland through an orifice of the meibomian gland include compression of the RF electrode itself on the eyelid. In this embodiment, the eyecup becomes the foundation or "back-stop" for compression using the RF electrode. In another embodiment, rollers or other projections separate and independent from the RF electrodes may be used to express the melted, softened, or loosened, obstructions from within the channel of the meibomian gland through an orifice of the meibomian gland. In this embodiment, the RF electrode remains at a fixed distance and other mechanical structures, such as rollers compress the eyelids to express the melted, softened, or loosened, obstructions from within the channel of the meibomian gland through an orifice of the meibomian gland. Any of these mechanisms for expressing obstructions may be referred to as mechanical expressors configured to express the obstruction from the duct of the meibomian gland.

In another embodiment, direct localized aspiration using an aspiration means on the inner eyelid surface may be used to force the melted, softened, or loosened, obstructions from within the channel of the meibomian gland through an orifice of the meibomian glands.

Vibrational or ultrasonic energy may also be used to express melted, softened, or loosened, obstructions from within the channel of the meibomian gland through an orifice of the meibomian glands.

In any of the RF delivery systems described herein, temperature monitoring is useful to avoid damage to the eyelids and surrounding tissues. Temperature monitoring could be achieved by thermocouples at the outer surface layer. RF and microwave energy has been known to disrupt temperature monitoring systems such as found in thermocouples. Preferably a fiber optic temperature sensor could be employed that advantageously is not affected by RF and electrical energy sources. In addition, these fiber optic temperature monitoring systems can be made very small and inexpensively as described in other temperature sensing applications.

Further, temperature control and feedback systems may also be used. Temperature monitoring could be achieved by thermocouples at the outer surface layer. RF and microwave energy has been known to disrupt temperature monitoring systems such as found in thermocouples. Preferably a fiber optic temperature sensor could be employed that advantageously is not affected by RF and electrical energy sources. In addition, these fiber optic temperature monitoring systems can be made very small and inexpensively as described in other temperature sensing applications.

Another method for controlling energy delivery to the meibomian gland is through impedance monitoring. A sensitive impedance monitoring system would be useful since the tissue itself would not undergo high impedance changes which typically occurs though the process of desiccation. As tissue becomes denatured through desiccation, tissue impedance increases due to a loss of cellular fluid. Once impedance measurements increase, energy delivery would be automatically reduced by the use of an impedance monitoring and feedback control system. In the meibomian gland application, impedance measurements would need to have a high sensitivity since the degree of desiccation would be minimal. However, in combination with an aspiration means that continually withdraws expressed fluid from the treatment zones, an impedance measurement/feedback system could provide sensitive control in the amount of energy applied to the meibomian glands in combination with a temperature sensing mechanism or by itself.

Figure 31:
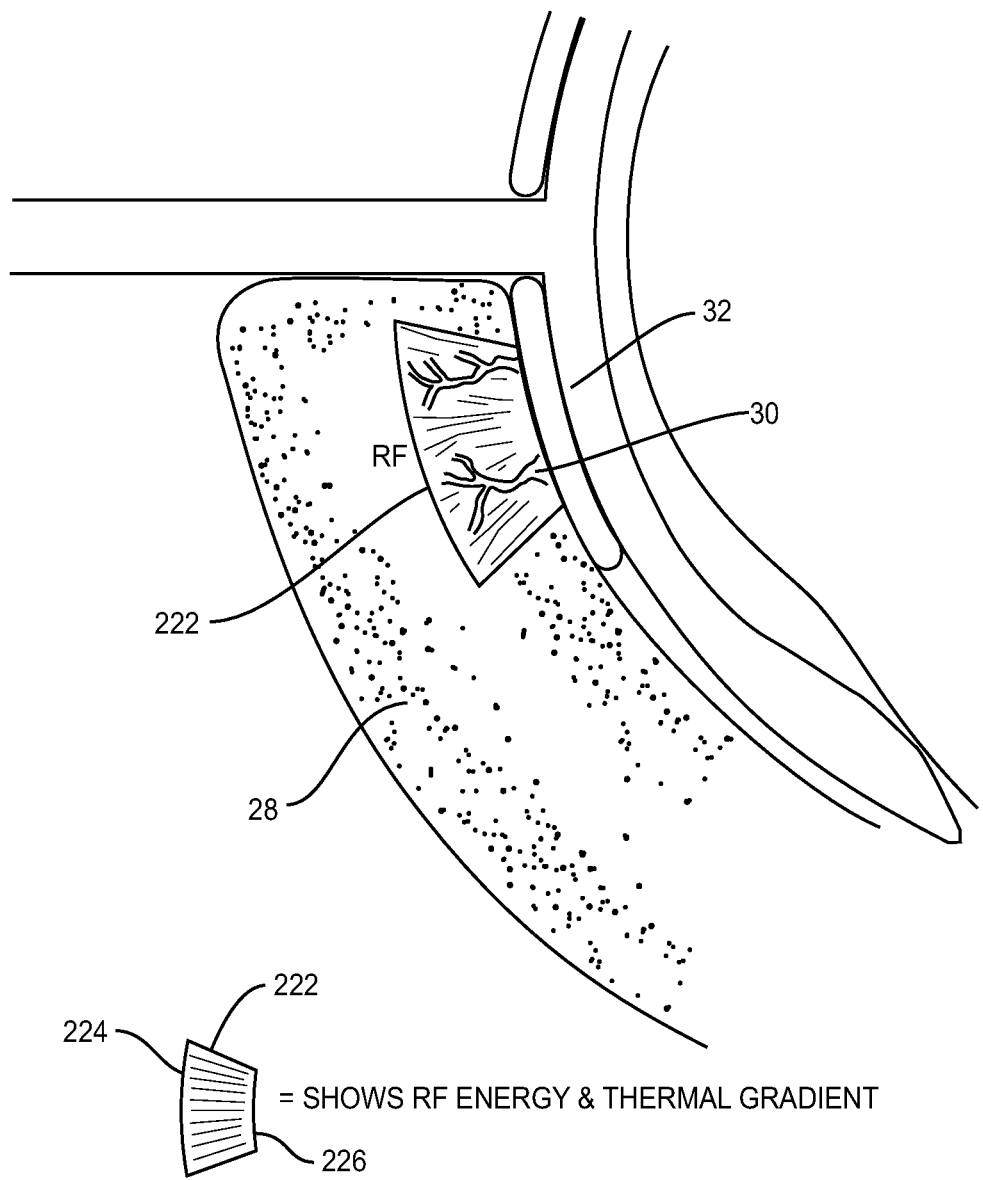
FIG. 31 illustrates a thermal gradient created by the application of RF energy via an exemplary RF electrode positioned on an inner surface of an eyelid.

FIG. 31 shows varying energy densities in tissue. The energy density can be greater within the tissue rather than at the surface of the tissue, which provides an advantage over methods and apparatuses that apply heat to the surface and rely on the heat being conducted through the tissue. An area 222 of thermal gradient is created, wherein an area of greater thermal energy 224 and an area of lesser thermal energy 226 is created by the application of the RF energy to selectively target the internal portions of the meibomian glands within the eyelids. In these systems, in order to heat the contents of the meibomian gland to the desired temperature, often the surface temperature becomes too hot for the patient's safety and comfort. By using the RF energy to direct thermal energy to specific points within the meibomian glands (such as the obstructions) rather than at the surface of the eyelid, the obstructions within the channel of the meibomian gland may be heated to a temperature sufficient to melt, soften, or loosen the obstruction without damaging the tissue at the surface of the eyelid.

Figure 32:
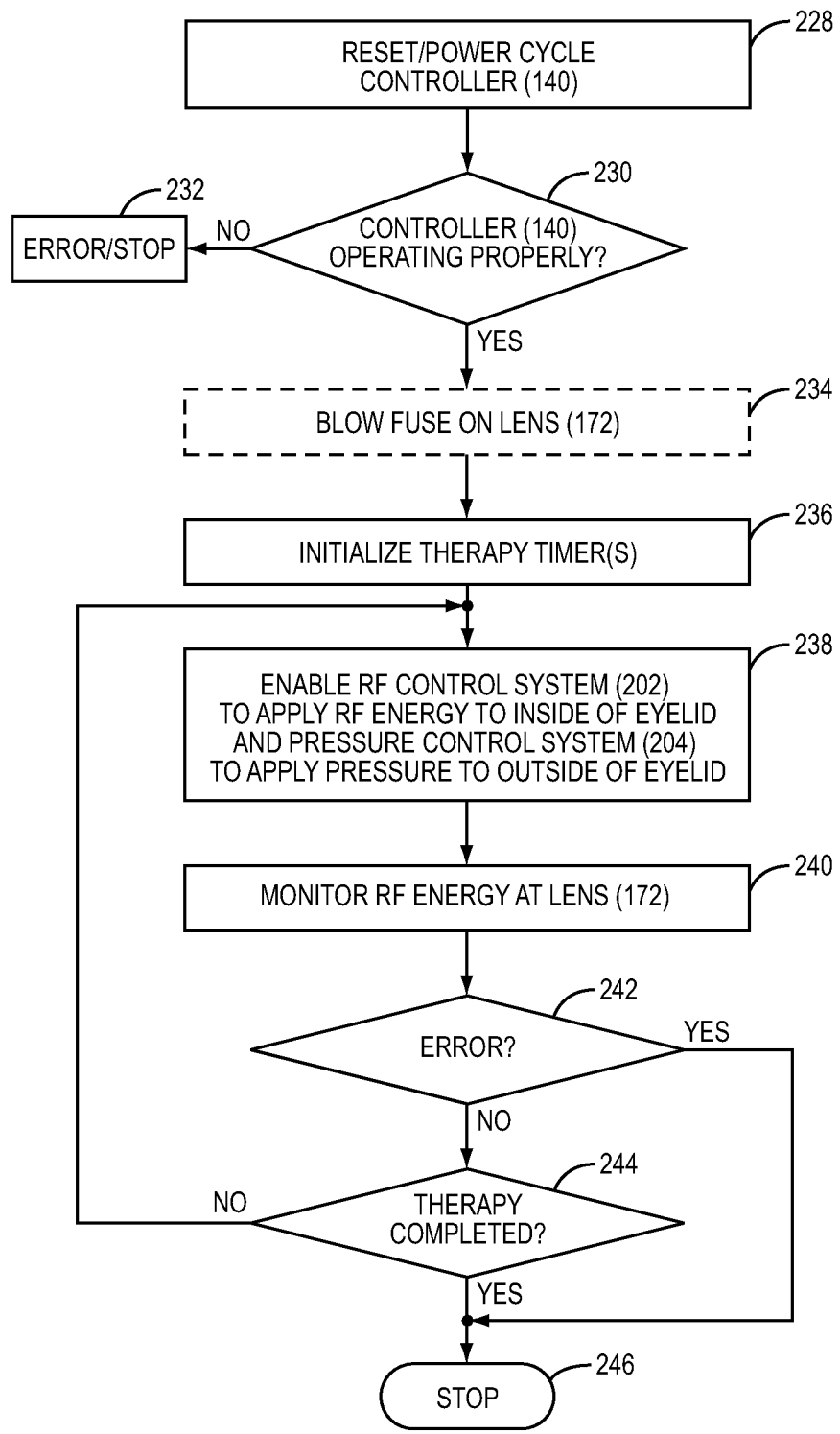
FIG. 32 is a flowchart illustrating the basic process employed by the heat and force application device to selectively and controllably apply heat to the inside of a patient's eyelid and/or force to the outside of the patient's eyelid, according to one embodiment.

FIG. 32 illustrates a flowchart which describes the overall operation and logic of the heat and force application device 136 in FIG. 22 that is carried out by the controller 138 and its systems, including the RF control system 202 and the pressure control system 204. The process starts by the controller 138 resetting in a reset state (step 228 in FIG. 32). The controller 138 always starts in a reset state in the disclosed embodiment. The reset state may occur as a result of a power cycle or if a new disposable component 140 is connected to the controller 138. After resetting, the controller 138 performs a series of tests prior to beginning treatment to determine if the controller 138 and its components are operating properly (decision 230 in FIG. 32). If not, an error is noted and the controller 138 stops operation by entering into the stop state (step 232 in FIG. 32). The stop state disables the RF electrode. If the controller 138 is operating properly (decision 230 in FIG. 32), the controller 138 proceeds with the operations to begin a treatment.

As an option, the controller 138 may first blow a fuse on the lid warmer to create an open circuit in a fuse blow state (step 234 in FIG. 32). This is so a lid warmer cannot be reused for subsequent treatments for safety and contamination reasons. As part of the operation check in decision 230, the controller 138 may determine if the fuse on the lid warmer has been blown. If so, this would be an indication that the lid warmer has already been used, and the controller 138 would enter the stop state (step 232 in FIG. 32). The controller 138 will continue to allow operation with the installed lid warmer after the fuse is blown until the lid warmer is removed. In such case, the controller 138 will enter the reset state (step 228 in FIG. 32).

Next, the controller 138 prepares for a therapy. The controller 138 may first initialize therapy timers in the timer and display controller 150. Timers allow the user of the controller 138 to track the amount of time that therapy has occurred, including heat and force application. Different patients may require different amounts of time for the application of heat and force during treatments. For example, a treatment cycle may include the application of heat for three minutes, but force may need to be applied, disengaged, and reapplied several times during the three minute therapy time period.

Subsequently, the controller 138 enables the RF control system 202 and the pressure control system 204 to apply heat and force to the patient's eyelid as part of a run state (step 238 in FIG. 32). RF energy is applied to heat the internal portions of the meibomian glands and force may also be applied to the outside of the patient's eyelid, as previously discussed. However, note that the controller 138 could also be used to direct RF energy and/or force to any part of the patient's eye or supporting structure, including but not limited to both to the outside of the patient's eyelid, and RF energy to the outside and force to the inside of the patient's eyelid. The controller 138 then monitors the RF energy and force applied to the patient's eyelid as part of the RF energy and pressure regulation in a monitor state (step 240 in FIG. 32). RF energy and force may be constantly applied and temperature and pressure monitored during therapy. If an error is detected (decision 242 in FIG. 32), the controller 138 enters the stop state to discontinue therapy (step 246 in FIG. 32). If an error is not detected, the process continues until either an error is detected (decision 242 in FIG. 32) or the therapy is completed (decision 244 in FIG. 32).

Other methods and apparatuses for heating the meibomian glands to melt, soften, and loosen obstructions within the meibomian glands, and for expressing the melted, softened, or loosened obstructions from within a duct, channel, or acinus of the meibomian gland, may be used. Some non-limiting examples are provided in FIGS. 33-37E described below.

Figure 33:
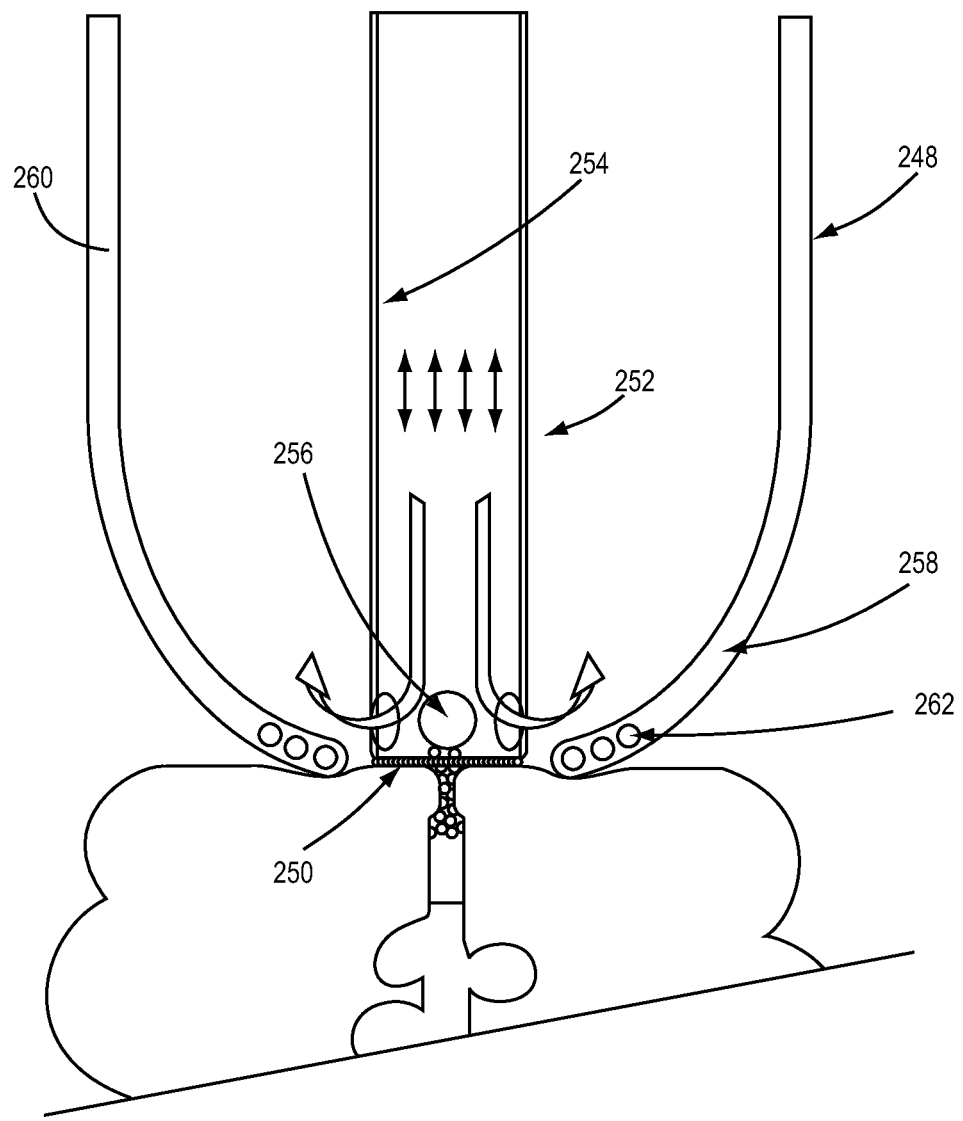
FIG. 33 is a broken away side view of an exemplary apparatus for clearing obstructed meibomian glands.

FIG. 33 employs microdermabraision or exfoliation to remove any cells or cellular material that may have overgrown the gland opening. Microdermabraision is a process that was developed for use in dermatology to remove dead skin cells. As shown in FIG. 33 a probe or tip 248 is equipped with an abrasive surface 250 that is adapted to scrape the skin. The abrasive employed is usually a diamond power or other suitable material, well known to those skilled in the art. An inner tube 252 having a central bore 254 includes holes defining openings 256 through which a fluid such as air is pumped. An outer covering 258 surrounds the inner tube 252 to form an outer tube 260, but at its lower edge extends slightly lower and is spaced from the abrasive surface 250 and a space is defined between the lower ends of the respective inner and outer tubes 252, 260. The outer covering 258 is connected to aspiration, vacuum, and/or suction that operates as described herein below.

In operation, the clinician would place the abrasive tip 250 in contact over the gland orifice creating a seal between the tip and the skin. Movement of the probe 248 would cause the abrasive 250 on the bottom of the tip to separate the cells from the skin and the aspiration, suction or vacuum would extract the cellular material from the vicinity of the gland opening. In addition, depending upon the obstruction, aspiration, suction and/or vacuum alone may be sufficient to extract the obstruction.

Additional features may also be providing to the microdermabraision tip such as a RF heating element 262 which could be placed in the outer covering 258 near the tip. In one embodiment, the RF heating element 262 may be similar to the RF electrode 32 described above. In addition, the inner tube 252 could be equipped such that ultrasonic energy could be delivered to the obstruction as discussed herein above.

Another embodiment may employ a chemical agent to clean the gland margin and to remove or exfoliate cells from the meibomian gland orifice. For example Ophthaine® or a similar pharmacological agent may be employed to assist in removing epithelial cells from over the gland orifice. A probe similar to that shown in FIG. 33 may be employed, except that the inner tube will deliver the chemical agent and the suction applied by the outer covering will be used to evacuate the used chemical agent and cellular material mixture away from the gland margin. Similarly, the heating and vibrational features discussed above may also be included.

Figure 34:
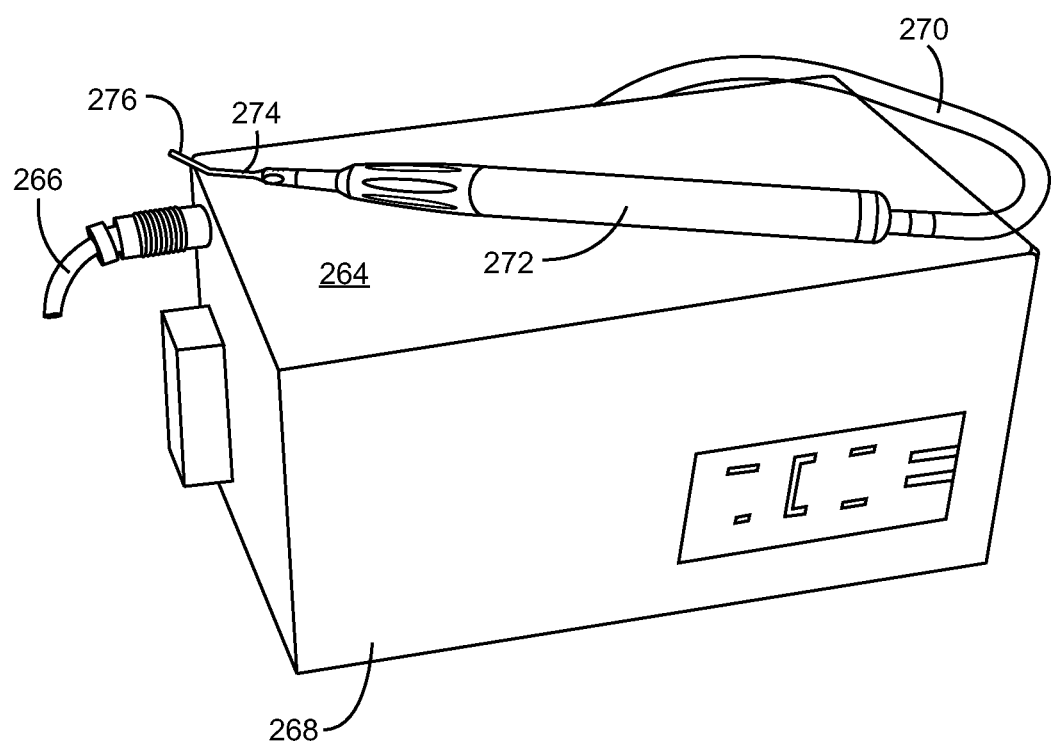
FIG. 34 is a perspective view of a suction device for clearing glands.

FIG. 34 illustrates a prototype hand held suction system generally indicated at 264 that was constructed. The system comprised an AC power supply 266 which powered a suction pump 268 to which tubing 270 was connected. At the opposite end of tubing 270 a probe 272 was connected. A tip 274 having a 1 mm diameter and a 200 micron orifice was attached to the end of the probe 272. The probe end 276 was curved for ergonomic access to the gland orifice. In use, the tip 274 is placed on or proximate the gland orifice and the applied vacuum is used to collect the obstruction as it exits the orifice or may alternatively be employed to assist in expression of the obstruction. In one embodiment, the probe may also include a regulated RF heating element as described herein, such as the RF electrode 32.

Figure 35:
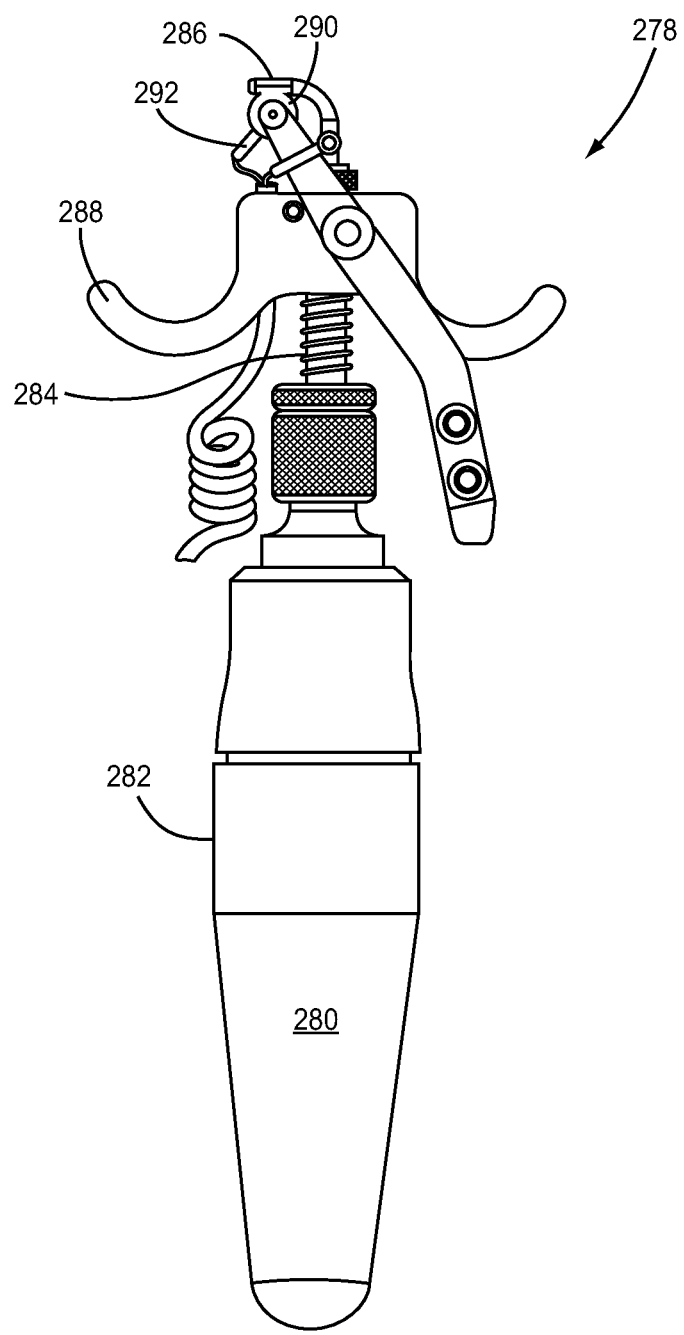
FIG. 35 is a side view of another embodiment of the apparatus for clearing meibomian glands.

FIG. 35 illustrates another prototype of a hand held apparatus generally indicated at 278. The system comprised a power supply 280 which powered an electromagnet (not shown) which was encased in a handle 282 that may be easily held by the clinician in one hand. A rod 284 is mounted for reciprocating motion to the output of the electromagnet. The throw or amount of movement of the rod 284 is 0.5 mm in one embodiment. At the end of rod 284 is mounted a back plate 286 which is substantially perpendicular to the axis of rod 284. Further, a lever 288 is pivotally mounted to rod 284 and operates to actuate a roller 290. A RF heating means or RF heater 292 may be mounted in the back plate 286. The RF heater 292 is also provided with an appropriate power source. In one embodiment, the RF heater may be an RF electrode and connected to an RF generator to generate RF energy that be directed into the eyelid to selectively target obstructions in the meibomian glands in order to soften or melt such obstructions. In operation, the device is positioned such that the back plate 286 is positioned between the cornea and the back surface of the eye lid. The lever 288 is actuated such that the roller 290 comes into contact with the front surface of the eye lid. The arc of the roller 290 is such that the eye lid is squeezed between the foregoing. The clinician may elect to maintain the back plate 286 and the roller under tension for a preselected period of time to soften the obstruction. Once the desired temperature has been reached, further pressure on the lever 288 will cause the roller to move from the bottom of the meibomian gland (the end away from the orifice) to the top of the gland to express the obstruction from the gland in a "milking type" motion. Thus, a repeatable regulated method for opening obstructed meibomian glands is provided.

Figure 36A:
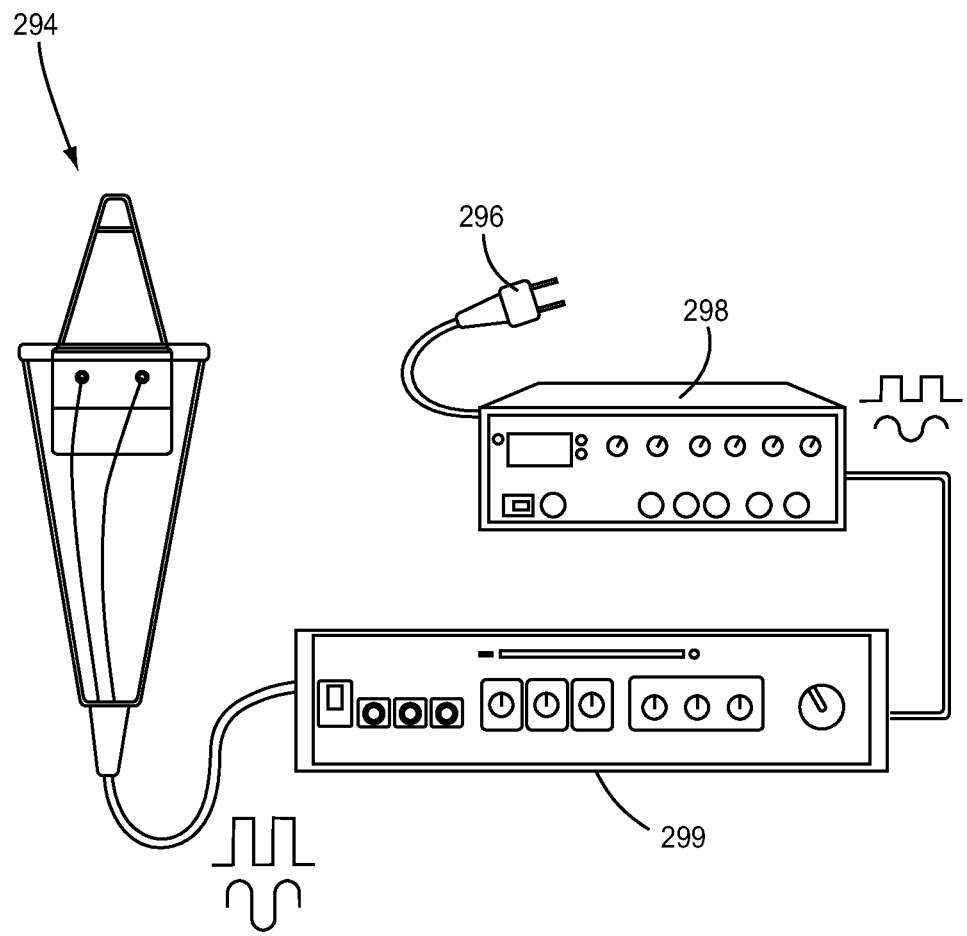
FIG. 36A is a schematic view of another embodiment of the apparatus for clearing meibomian glands.
Figure 36B:
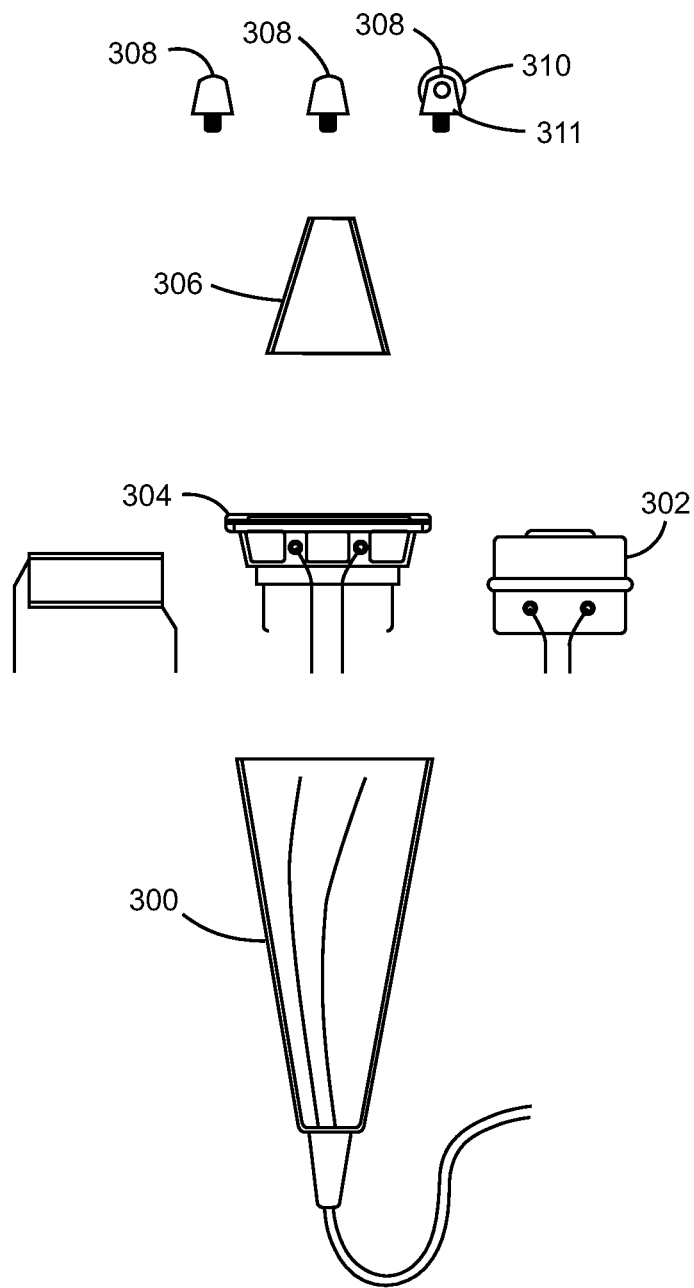
FIG. 36B is an exploded view of the hand-held probe of the embodiment of FIG. 36A.
Figure 36C:
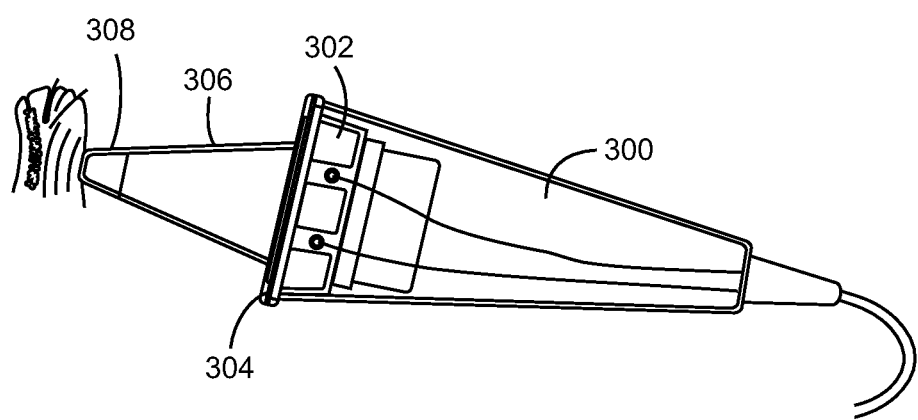
FIG. 36C is a side view of the hand-held probe of FIGS. 36A and 36B applying force to an eyelid.

The embodiment illustrated in FIGS. 36A through 36C illustrates a hand held apparatus generally indicated at 294. The apparatus 294 comprises a power source 296 which may be a DC source such as a battery or an AC source similar to those discussed herein above. The power source 296 resides within a housing 298. The power source 296 provides electrical current to a wave form generator 299 which powers an acoustic amplifier 302 (for example, a small audio speaker) also located within housing 298 and mounted at an ergonomic angle therein. The acoustic amplifier 302 is programmed to vibrate in a wave format at a frequency of 0 to 200 Hz at an amplitude in the range of 0.1 mm to 5 mm, 0.25 mm to 5 mm, or 0.5 mm to 5 mm. Initial experiments indicate that free air amplitude of 3-4 mm at a frequency of 60 Hz to 125 Hz is well tolerated and after 10-30 seconds of application seems to impart a natural numbing effect to the eyelid/gland. Mounted in operative association atop the acoustic amplifier 302 is an annulus 304 that floats thereon and includes a cone shaped housing 300 extending perpendicularly away from the amplifier 302 that encloses the amplifier 302. The end 306 of the housing 300 is adapted to mount a variety of tips 308. For example, the tip 308 may comprise a roller 310 mounted for rotation in a cradle 311. Further, the tip 308 may be modified to include a regulated RF heating element (not shown) that acts to soften the obstruction. In one embodiment, the end 306 or tip 308 may include a regulated RF heating element as described herein, such as the RF electrode 32, the RF heating element configured to generate RF energy that be directed into the eyelid to selectively target obstructions in the meibomian glands in order to soften or melt such obstructions Other tip configurations may include a vacuum for collecting the obstruction after expression thereof from the gland and different tip configurations to apply various contact areas and resulting forces. Thus, it will be seen that the obstruction is actually subjected to a pair of forces, the first being the weight of the device itself on the gland which may be combined with additional pressure by the health care provider pressing on the gland plus the additional intermittent force delivered to the gland by the vibratory or pulsatory force of the tip 308. The first force may be a fixed constantly applied force or one that increases to a preselected maximum. Testing has indicated that use of the foregoing method, i.e., applying a first force to the meibomian gland and a second pulsatile force to the meibomian gland allows delivery of a greater quantity of energy to the obstruction while lowering the perceived pain level to the patient. It is believed that this is the result of an overall lower degree of localized nerve stimulation about the orbit. Heating the gland is also beneficial in the event softening of the obstruction is needed prior to expression thereof Another embodiment is shown in FIGS. 37A through 37E wherein the treatment apparatus is incorporated into a goggle-like device, termed herein as the "hydro-oculator" which is a device worn on the head that locates the treatment mechanism proximate the eyelids, generally indicated at 312. The hydro-oculator 312 comprises a flexible frame 314 having a headband 316 (which may be elastic) connected thereto at each end. Connected to the bottom of the frame 314 is a molded housing 318 which has an angled leg 320 which is adapted to overlie the cheek bone when the apparatus is in use. Further, an expandable fluid or gas impermeable container referred to herein as a bladder 322 is positioned within the cavity defined by the space between the housing and the lower eye lid. A pumping mechanism is provided that facilitates movement of a fluid or gas, collectively referred to herein as a "medium" (not shown) into and out of each of the respective bladders 322. In one embodiment, the patient would position the hydro-oculator 312 on his or her head such that the leg 320 of molded housing 318 rests on the upper cheek bone as best shown in FIGS. 37C through 37E. A regulated heated medium is pumped into the bladders 322 causing partial expansion thereof in order to apply a pressure to the eyelids in the range of from zero to fifty pounds per square inch (50 psi). The bladder 322 containing the heated medium (a water based solution being preferred) is positioned on the eyelids over the meibomian glands for a preselected period of time (up to thirty minutes) to soften the obstruction. It is desirable in one embodiment to include an RF heating element, such as RF electrode 32, in the hydro-oculator 312 in order to generate RF energy to heat the medium. In this embodiment, the RF heating element may or may not be placed in direct contact with the bladder or the eyelids, but may direct RF energy into the bladder 322 to warm the medium, or may direct RF energy directly into the eyelid to selectively target obstructions in the meibomian glands in order to soften or melt such obstructions, or may do both. In another embodiment, the heat source may be placed in direct contact with the eyelids, which thereby transmits thermal energy to the meibomian glands, in contrast to the prior art which heats a confined space in front of the open eye where heat could be transmitted to the ocular bulbi structures such as the crystalline lens which introduces the possibility of cataract formation. Thereafter, the bladder is slowly expanded to a preselected maximum such that the force on the gland increases from the bottom up to the top or orifice end of the gland such that the obstruction is expressed therefrom in a "milking" type of action. Milking may be applied at a preselected frequency between zero and five hertz (0-5 Hz) and for a preselected period of time, usually not more than thirty minutes. In addition, the medium may be "pulsed", i.e., milkingly moved into and out of the bladder to further facilitate expression of the obstruction from the gland. Pulsing may also be achieved by providing an external force to the bladder and transmitting the force through the fluid into the gland. Pulsing may be applied at a preselected frequency between zero and one hundred hertz (0-100 Hz) for a preselected period time, usually not more than thirty (30) minutes. A chemical or pharmacological agent may be inserted into the meibomian gland to assist in softening the obstruction and any of the extraction modalities mentioned above may be further employed to assist in removing the obstruction.

Figure 38:
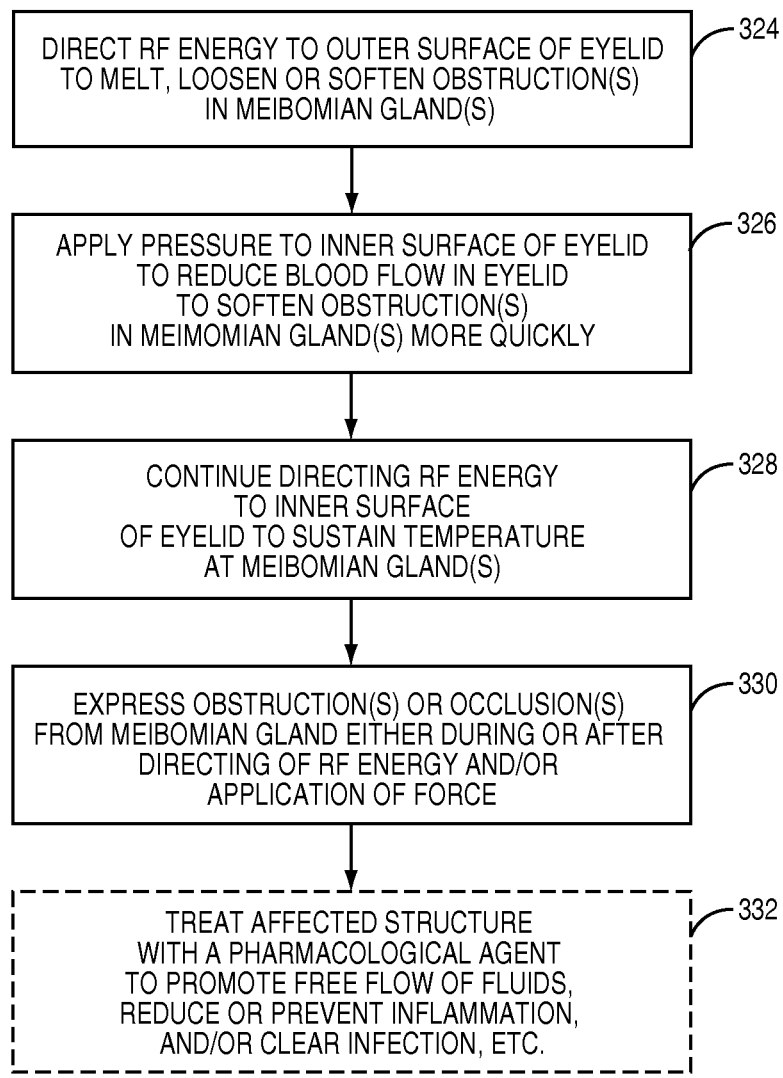
FIG. 38 is a flowchart illustrating an alternate meibomian gland treatment employing applying heat to the outside of a patient's eyelid and force to the inside of the patient's eyelid for treating meibomian glands.

Although the present application discusses and provides devices for directing heat or RF energy and force to the eyelid to treat MGD, many configurations are possible. Heat or RF energy and force may be applied in a number of different combinations and manners to treat MGD. For example, FIG. 38 illustrates an alternative embodiment for directing RF energy and force to tissue proximate a patient's meibomian gland to treat MGD. In this embodiment, RF energy is applied and force is applied. RF energy is applied to selectively target and heat the internal portions of the meibomian glands to the desired temperature level (step 324). For example, RF energy may be applied to raise the temperature at the inside of the eyelid between 43-47 degrees Celsius. The RF energy may also be regulated, meaning that a RF control means or element is controlled to be within the temperatures and means that are safe for the eyelid and at a sufficient temperature for melting, loosening, or softening an occlusion or obstruction in the meibomian gland.

A force or pressure may also be applied to tissue proximate the patient's meibomian gland to increase the efficiency of heat transfer. As previously described, the application of force towards the RF electrode with the patient's eyelid "sandwiched" therebetween provides greater surface contact between the RF electrode and the eyelid for more efficient conductive heat transfer. Further, the application of force reduces blood flow in the eyelids to reduce convective heat loss through the eyelids and allow the temperature at the meibomian glands to not only rise to higher levels, but do so more quickly and efficiently (step 326).

In the process shown in FIG. 38, the RF energy and/or force may be maintained for a period of time sufficient to raise the temperature at the meibomian glands sufficient to melt, loosen, or soften the obstructions or occlusions (step 328). The force may be maintained after the RF energy is removed, or vice versa depending on the treatment technique desired. Maintaining force after the RF energy is removed may reduce convective heat loss at the meibomian glands and thus keep the temperature level at the meibomian glands to the therapeutic levels for more time than if the force was removed. Maintaining the RF energy without maintaining force may be employed to allow blood flow in the eyelids, such as between successive treatments. For example, it may be desirable to maintain the application of RF energy to lessen the total amount of treatment time while applying and removing force between treatments. Also, it may not be necessary to apply significant amounts of force, or for the same duration as application of RF energy, if the obstruction or occlusion is located in close proximity to the lid margin rather than in the deeper portions of the meibomian gland. Thereafter, either during the application of RF energy and/or the application of force or after either, obstructions or occlusions in the meibomian glands may be expressed so that sebum flow is restored from the glands to establish a sufficient lipid layer (step 330).

The force may be regulated, meaning that a force generating means is controlled to be within the pressure ranges that are safe to be applied to tissue proximate the meibomian glands and at sufficient pressure to allow the temperature at the meibomian gland to be raised sufficiently. The force may be applied during the application of the RF energy, after the application of RF energy, or both during and after the application of RF energy. In either case, the force may assist in expressing occlusions or obstructions when in a loosened, softened, or melted state from the meibomian glands. The force may include vibratory type forces, including those generated mechanically or using fluid type devices or mechanisms. The level of force needed to express obstructions or occlusions in the glands may be greatly reduced when RF energy is applied to the obstructions or occlusions to place them in a melted, softened, or loosened state.

The application of force can also stimulate the movement of fluids or suspensions of occlusions or obstructions from the glands. Embodiments described herein can be used with devices which generally apply a regulated force or milking action to the eyelid to express the fluids or suspensions or to otherwise mechanically stimulate the movement of fluids from the glands. In some instances, a small, gentle, continuous force applied to the eyelid will assist in expression of the fluids and suspensions. Vibration can also be used when applying force simultaneously or immediately after the heating to further assist in the expression.

Any device may be employed to generate RF energy or heat on the outside, inside, and/or both the outside and inside of the patient's eyelid, including those described herein. Other devices may be employed, such as the apparatus disclosed in U.S. Patent Application Publication No. 2007/1016254, entitled "Method and apparatus for treating gland dysfunction employing heated medium," and incorporated herein by reference in its entirety. In this application, an apparatus is employed to apply heat to the outside of the patient's eyelid via heated fluid transfer. Further, a gas may be employed as opposed to fluid to apply heat to the patient's eyelid.

Where only heat is applied, regulated heat can include controlling heat according to a temperature profile. The temperature profile may be a constant temperature, include ramp-ups, ramp-downs, peaks and valleys. Further, the temperature profile may include heat pulses or be modulated with various characteristics, including the use of pulse width modulation (PWM) techniques. The use of modulated heat may allow the temperature to be raised even higher at the eyelid without damage to the patient's eyelid since the increased temperatures are applied for shorter periods of time. Obstructions or occlusions in the meibomian glands may have melting, loosening, or softening points that are beyond temperatures that may be applied without the use of modulated heat. The temperature needed to melt, loosen, or soften obstructions or occlusions may depend on how keratinized the obstruction or occlusion is. Not all obstructions or occlusions have the same melting, loosening, or softening points. By example only, elevated temperatures between 47 and 55 degrees Celsius may be possible when applying modulated heat, especially if the eyelid has been anesthetized.

The regulated heat can be maintained at a therapeutic temperature for a treatment period. The treatment period can be approximately 1 to 10 minutes for example, since the application of force may reduce the amount of time it takes for the heat source to raise the temperature at the meibomian glands to the desired level. The heat could also be repeatedly applied and maintained for a desired period of time to keep the occlusion or obstruction in a melted, loosened, or softened state. Either during or after such treatment by regulated heat, mechanical expression of lipids and other fluids from the meibomian glands has been found to clear obstructions which have essentially melted or been placed in a suspension state (by virtue of melting materials binding solids together).

Optionally, after expression of the occlusions or obstructions is performed (step 330), an optional pharmacological agent may be applied to the meibomian gland to promote the free flow of sebum and/or reduce or prevent inflammation or infections of the eye or eyelids (step 332). The previous discussion in the flowcharts of FIGS. 5, 18, and 20 regarding use of pharmacological agents above is equally applicable for this embodiment and thus will not be repeated here. Those compounds are illustrative examples of appropriate pharmacological agents, but those skilled in the art will appreciate that other pharmacological compounds may be utilized.

Any device may be employed to generate heat on the outside of the patient's eyelid, including those described herein. Other devices may be employed, such as the apparatus disclosed in U.S. Patent Application Publication No. 2007/1016254, entitled "Method and apparatus for treating gland dysfunction employing heated medium," and incorporated herein by reference in its entirety. In this application, an apparatus is employed to apply heat to the outside of the patient's eyelid via heated fluid transfer. Further, a gas may be employed as opposed to fluid to apply heat to the patient's eyelid.

In practice, the methods and apparatuses disclosed herein may be used to treat MGD. A doctor or other trained professional may carry out the following method. The patient may be positioned within a restraining apparatus. The patient's eye lids may be prepped with appropriate topical agents (lidocaine, antiseptic, etc.). An eyecup as described herein may be placed on the globe of the patient's eye. The eyelid may be placed on positioning pads or gutters. In one embodiment, aspiration may be applied to stabilize the eyelids once the proper position is established. The RF energy delivering device is then placed onto the eyelid position and locked into place. RF energy is applied to the meibomian glands while monitoring the temperature on eye cup. Aspiration may also be applied, during or after the application of the RF energy. The RF energy may be cycled as determined to achieve heating of the gland ducts and melting of gland obstructions. The doctor or trained professional may then verify that melted materials are being obtained within collection chamber. In one embodiment, rinse cycles may be applied if necessary during the RF energy application and intermittently with aspiration to improve the transport of melted materials from the meibomian glands. In one embodiment, fluid may be delivered into the treatment area to improve the efficiency of RF energy in situations where the treatment and aspiration have dried out the treatment area. At the completion of the RF energy delivery, aspiration may be stopped. In one embodiment, after the RF energy application and/or aspiration is completed, topical agents or drugs may be applied if necessary through the same aspiration conduit or through a separately supplied conduit on the eyecup. Gutters on the eye cup may be used to improve the efficiency of the drug delivery. The eye cup and RF energy apparatus may then be removed from the patient.

Those skilled in the art will recognize improvements and modifications to the preferred embodiments of the present invention. Heat as used in this application can mean the application of thermal energy, including RF or microwave energy. Heat may be applied to the patient's eyelid, related structure, or surrounding tissue using any type of thermal energy. Force may be applied to the patent's eyelid to apply pressure to the patient's eyelid, related structure, and/or surrounding tissue using any type of force or force generating means or device. All such improvements and modifications are considered within the scope of the concepts disclosed herein and the claims that follow.

What is claimed is:

1. A method of treating meibomian gland dysfunction, comprising the steps of:
    directing radio frequency (RF) energy to an internal portion of a meibomian gland;
    selectively targeting an obstruction within a duct of the meibomian gland with the RF energy to melt, loosen, or soften the obstruction;
    expressing the obstruction from the duct of the meibomian gland; and
    sensing a presence of fluid being expressed from the meibomian gland.

2. The method of claim 1 further comprising directing the RF energy until an increase in thermal energy occurs at the obstruction in the duct.

3. The method of claim 1, wherein the selectively targeting the obstruction further comprises directing RF energy waveforms such that the RF energy waveforms are absorbed preferentially by energy absorbing cellular fluids, saline or lipid containing materials found in the duct of the meibomian gland.

4. The method of claim 1, wherein the selectively targeting the obstruction further comprises directing RF energy at a predetermined depth in the meibomian gland.

5. The method of claim 1, wherein the applied RF energy causes contents within the duct of the meibomian gland to be heated to between 37 and 45 degrees Celsius.

6. The method of claim 1 further comprising controlling an amount of the RF energy applied to an internal portion of the meibomian gland.

7. The method of claim 6, wherein the controlling the amount of the RF energy further comprises directing an amount of RF energy sufficient to selectively heat contents within the duct of the meibomian gland to a known temperature.

8. The method of claim 6, wherein the controlling the amount of the RF energy further comprises directing an amount of RF energy sufficient to selectively heat lipid containing materials in the meibomian gland.

9. The method of claim 1 further comprising adjusting a power and/or a duration of the RF energy.

10. The method of claim 1 further comprising adjusting a shape of a waveform of the RF energy.

11. The method of claim 1 further comprising providing pulsed waveforms of the RF energy.

12. The method of claim 1 further comprising adjusting a shape of an RF electrode that applies the RF energy.

13. The method of claim 1 further comprising monitoring a temperature at a surface of an eyelid.

14. The method of claim 1 further comprising controlling delivery of the RF energy to the meibomian gland through impedance monitoring.

15. The method of claim 1 further comprising reducing the application of RF energy based on the sensing the presence of the fluid being expressed from the meibomian gland.

16. The method of claim 1 further comprising reducing power of the applied RF energy based on the sensing the presence of the fluid being expressed from the meibomian gland.

17. The method of claim 1 further comprising stopping application of the RF energy when the sensing the presence of the fluid being expressed from the meibomian gland is indicative of no additional fluid being collected.

18. The method of claim 1, wherein the RF energy comprises energy having different frequencies.

* * * * *